US009573957B2

(12) United States Patent
Abeywardane et al.

(10) Patent No.: US 9,573,957 B2
(45) Date of Patent: *Feb. 21, 2017

(54) INHIBITORS OF LEUKOTRIENE PRODUCTION

(71) Applicants: Asitha Abeywardane, Danbury, CT (US); John Broadwater, Southbury, CT (US); Steven Richard Brunette, New Milford, CT (US); Thomas Martin Kirrane, Jr., Middlebury, CT (US); Hossein Razavi, Danbury, CT (US); Robert Sibley, North Haven, CT (US); Lana Louise Smith Keenan, Poughquag, NY (US); Qiang Zhang, Ridgefield, CT (US)

(72) Inventors: Asitha Abeywardane, Danbury, CT (US); John Broadwater, Southbury, CT (US); Steven Richard Brunette, New Milford, CT (US); Thomas Martin Kirrane, Jr., Middlebury, CT (US); Hossein Razavi, Danbury, CT (US); Robert Sibley, North Haven, CT (US); Lana Louise Smith Keenan, Poughquag, NY (US); Qiang Zhang, Ridgefield, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/330,307

(22) Filed: Jul. 14, 2014

(65) Prior Publication Data

US 2015/0018334 A1    Jan. 15, 2015

Related U.S. Application Data

(60) Provisional application No. 61/846,139, filed on Jul. 15, 2013.

(51) Int. Cl.
| | | |
|---|---|---|
| C07D 487/08 | (2006.01) | |
| C07D 401/14 | (2006.01) | |
| A61K 31/4439 | (2006.01) | |
| A61K 31/496 | (2006.01) | |
| A61K 31/4709 | (2006.01) | |
| C07D 403/14 | (2006.01) | |
| A61K 31/506 | (2006.01) | |
| C07D 413/14 | (2006.01) | |
| A61K 31/4995 | (2006.01) | |
| A61K 31/551 | (2006.01) | |
| C07D 405/14 | (2006.01) | |
| C07D 471/04 | (2006.01) | |

(52) U.S. Cl.
CPC ......... *C07D 487/08* (2013.01); *A61K 31/4439* (2013.01); *A61K 31/4709* (2013.01); *A61K 31/496* (2013.01); *A61K 31/4995* (2013.01); *A61K 31/506* (2013.01); *A61K 31/551* (2013.01); *C07D 401/14* (2013.01); *C07D 403/14* (2013.01); *C07D 405/14* (2013.01); *C07D 413/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,918,092 | A | 4/1990 | Frenette et al. |
| 5,120,758 | A | 6/1992 | Satoh |
| 6,180,637 | B1 | 1/2001 | Schindler et al. |
| 7,098,222 | B2 | 8/2006 | Altenbach et al. |
| 7,429,665 | B2 | 9/2008 | Verhoest et al. |
| 7,674,802 | B2 | 3/2010 | Sandanayaka et al. |
| 8,551,982 | B2 | 10/2013 | Abeywardane et al. |
| 8,946,203 | B2 | 2/2015 | Abeywardane et al. |
| 2002/0132822 | A1 | 9/2002 | Noe et al. |
| 2006/0019269 | A1 | 1/2006 | Helgadottir et al. |
| 2006/0223792 | A1 | 10/2006 | Butler et al. |
| 2007/0066820 | A1 | 3/2007 | Sandanayaka et al. |
| 2007/0149544 | A1 | 6/2007 | Sandanayaka et al. |
| 2013/0196973 | A1 | 8/2013 | Abeywardane et al. |
| 2013/0236468 | A1 | 9/2013 | Bylock |

(Continued)

FOREIGN PATENT DOCUMENTS

| | | |
|---|---|---|
| CA | 2076573 A1 | 2/1993 |
| CA | 2280727 A1 | 8/1998 |

(Continued)

OTHER PUBLICATIONS

Online "http://practicalfragments.blogspot.com/2010/01/fragments-in-clinic-dg-051.html" accessed Feb. 17, 2016.*
Chaichian "Targeted Therapies in Systemic Lupus Erythematosus: A State-of-the-Art Review" J Clin Cell Immunol 2013, S6, 1-8.*
Skrupy "Advances in the Management of Sepsis and in the Understanding of Key Immunologic Defects of the Disorder" Anesthesiology. Dec. 2011 ; 115(6): 1349-1362.*
Garrido "Experimental models of sepsis and septic shock: an overview" Acta Cirúrgica Brasileira—vol. 19 (2) 2004 82-88.*
Simone, Oncology: Introduction, Cecil Textbook of Medicine, 20th Edition, 1996 vol. 1, pp. 1004-1010.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Johnson, et. al. "Relationships between drug activity in NCI preclinical in vitro and in vivo models and early clinical trials." British Journal of Cancer 2001, 84, 1424-1431.*

(Continued)

*Primary Examiner* — David K O'Dell
(74) *Attorney, Agent, or Firm* — Michael P. Morris; Usha R. Patel

(57) ABSTRACT

The present invention relates to aryl pyrazoles, and pharmaceutically acceptable salts thereof. The aryl pyrazoles of the present invention are useful as inhibitors of leukotriene $A_4$ hydrolase ($LTA_4H$) and treating $LTA_4H$ related disorders. The present invention also relates to pharmaceutical compositions comprising the aryl pyrazoles of the present invention, methods of using these compounds in the treatment of various diseases and disorders, and processes for preparing these compounds.

3 Claims, No Drawings

(56) References Cited

U.S. PATENT DOCUMENTS

| | | | |
|---|---|---|---|
| 2013/0244996 A1 | 9/2013 | Abeywardane et al. | |
| 2014/0031339 A1 | 1/2014 | Abeywardane et al. | |

FOREIGN PATENT DOCUMENTS

| | | | |
|---|---|---|---|
| WO | 9610999 | A2 | 4/1996 |
| WO | 9611192 | A1 | 4/1996 |
| WO | 2004056369 | A1 | 7/2004 |
| WO | 2007040682 | A1 | 4/2007 |
| WO | 2008052086 | A1 | 5/2008 |
| WO | 2011032050 | A2 | 3/2011 |
| WO | 2011114220 | A1 | 9/2011 |
| WO | 2012125598 | A1 | 9/2012 |
| WO | 2013012844 | A1 | 1/2013 |
| WO | 2014014874 | A1 | 1/2014 |

OTHER PUBLICATIONS

Healthline Online "http://www.healthline.com/health/inflammatory-bowel-disease", accessed Sep. 9, 2015.*
Online "http://www.brighamandwomens.org/Departments_and_Services/neurosurgery/Patient/VHLclinicFacts.aspx" accessed Feb. 17, 2016.*
Miller "Atherosclerosis" Journal of the American College of Cardiology vol. 49, No. 15, 2007, 1589-99.*
van der Laan "Variants in ALOX5, ALOX5AP and LTA4H are not associated with atherosclerotic plaque phenotypes: The Athero-Express Genomics Study" Atherosclerosis 239 (2015) 528-538.*
Elborn "Cystic fibrosis" The Lancet, Published online Apr. 29, 2016 Online "http://dx.doi.org/10.1016/S0140-6736(16)00576-6" 1-13.*
Konstan "A randomized double blind, placebo controlled phase 2 trial of BIIL 284 BS (an LTB4 receptor antagonist) for the treatment of lung disease in children and adults with cystic fibrosis" Journal of Cystic Fibrosis 13 (2014) 148-155.*
Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*
Liu "The role of leukotrienes in allergic diseases" Allergology International 2015, 64, 17-26.*
Davies, D. R. et al., "Discovery of Leukotriene A4 Hydrolase Inhibitors Using Metabolomics Biased Fragment Crystallography+", Journal of Medicanal Chemistry, vol. 52, No. 15, Aug. 13, 2009, pp. 4694-4715.
Grice, C.A. et al., "Current Status of Leukotriene A4 Hydrolase Inhibitors". Expert Opinion on Therapeutic Patents, vol. 18, No. 12, Dec. 1, 2008, p. 1333-1350.
International Search Report and Written Opinion for PCT/US2012/028843 mailed May 7, 2012.
International Search Report and Written Opinion for PCT/US2013/029054 mailed May 21, 2013.
International Search Report and Written Opinion for PCT/US2013/050624 mailed Sep. 11, 2013.
International Search Report and Written Opinion for PCT/US2014/046489 mailed Sep. 9, 2014.
International Search Report and Written Opinion for PCT/US2014/046492 mailed Sep. 11, 2014.
International Search Report for PCT/EP2013/054381 mailed May 21, 2013.
International Search Report for PCT/US2012/047024 mailed Sep. 20, 2012.
Minami, M. et al., "Molecular Cloning of a cDNA Coding for Human Leukotriene A4 Hydrolase". The Journal of Biological Chemistry, vol. 262, No. 29, 1987, p. 13873-13876.
Sandanayaka, V. et al., "Discovery of 4-[(2 S)-2-{[4-(4-Chlorophenoxy)phenoxy]methyl}-1-pyrrolidinyl]butanoic Acid (DG-051) as a Novel Leukotriene B4 Biosynthesis". Journal of Medicinal Chemistry, vol. 53, No. 2, Jan. 28, 2010, p. 573-585.
Sandanayaka, V. et al., "Discovery of novel leukotriene A4 hydrolase inhibitors based on piperidine and piperazine scaffolds". Bioorganice and Medicinal Chemistry Letters, Pergamon, Elsevier Science, GB, vol. 20, No. 9, May 1, 2010, pp. 2851-2854.
Thangapandian, Sundarapandian et al., "Molecular Docking and Pharacophore Filtering in the Discovery of Dual-Inhibitors for Human Leukotreine A4 Hydrolase and Leukotriene C4 Synthase", Journal of Chemical Information and Modeling, vol. 51, No. 1, Jan. 24, 2011, pp. 33-44.

* cited by examiner

INHIBITORS OF LEUKOTRIENE PRODUCTION

FIELD OF THE INVENTION

This invention relates to novel compounds that are useful as inhibitors of leukotriene $A_4$ hydrolase ($LTA_4H$) and are thus useful for treating a variety of diseases and disorders that are mediated or sustained through the activity of leukotrienes including asthma, and allergy; cardiovascular diseases including atherosclerosis, myocardial infarction and stroke; and inflammation diseases including atopic dermatitis, allergy, asthma, autoimmune diseases, Crohn's disease, cystic fibrosis, diabetic nephropathy, diabetic retinopathy, ulcerative colitis, and steatohepatitis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LT) are oxidized lipids that are produced by several cell types including neutrophils, mast cells, eosinophils, basophils, monocytes and macrophages. The first committed step in the intracellular synthesis of LTs involves oxidation of arachidonic acid by 5-lipoxygenase (5-LO) to leukotriene $A_4$ ($LTA_4$), a process requiring the 5-lipoxygenase-activating protein (FLAP). Leukotriene $A_4$ hydrolase ($LTA_4H$) catalyzes the hydrolysis of $LTA_4$ to produce leukotriene $B_4$ ($LTB_4$). Through the engagement of the $LTB_4$ receptors (BLT1, BLT2), $LTB_4$ stimulates an array of pro-inflammatory responses (leukocyte chemotaxis, cytokine release, etc.). The leukotriene pathway has been implicated in diseases in which inflammation is a critical component of the pathology; these include cancer, asthma, atherosclerosis, colitis, glomerularnephritis, and pain (for a review, see M. Peters-Golden and W. R. Henderson, Jr., M.D., N. Engl. J. Med., 2007, 357, 1841-1854).

BRIEF SUMMARY OF THE INVENTION

The present invention provides novel compounds which inhibit leukotriene $A_4$ hydrolase ($LTA_4H$) and are thus useful for treating a variety of diseases and disorders that are mediated or sustained through the activity of leukotrienes, including allergic, pulmonary, fibrotic, inflammatory and cardiovascular diseases and cancer.

In its broadest embodiment ("embodiment 1"), the invention relates to a compound of Table 1, and pharmaceutically acceptable salts thereof ("the compounds of the invention").

TABLE 1

Compounds of the invention.

| Ex. | Structure | Compound Name |
|---|---|---|
| 1 | 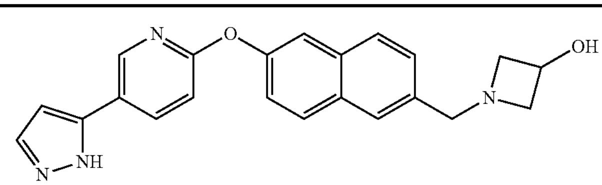 | 1-{6-[5-(2H-Pyrazol-3-yl)-pyridin-2-yloxy]-naphthalen-2-ylmethyl}-azetidin-3-ol |
| 2 | 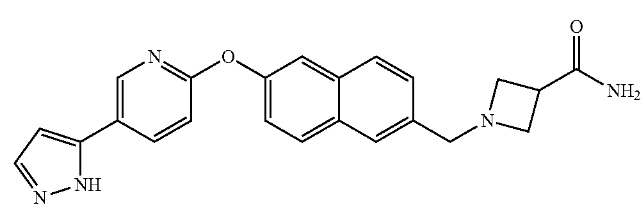 [SMILES: NC(=O)C1CN(Cc2ccc3cc(Oc4ccc(-c5ccn[nH]5)cn4)ccc3c2)C1] | 1-{6-[5-(2H-Pyrazol-3-yl)-pyridin-2-yloxy]-naphthalen-2-ylmethyl}-azetidine-3-carboxylic acid amide |
| 3 | 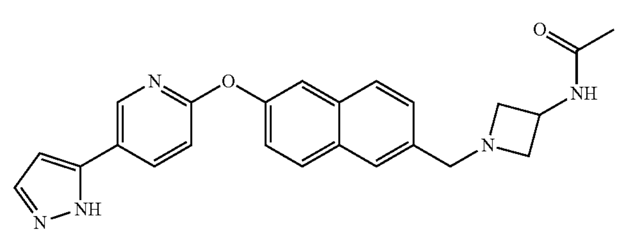 [SMILES: CC(=O)NC1CN(Cc2ccc3cc(Oc4ccc(-c5ccn[nH]5)cn4)ccc3c2)C1] | N-(1-{6-[5-(2H-Pyrazol-3-yl)-pyridin-2-yloxy]-naphthalen-2-ylmethyl}-azetidin-3-yl)-acetamide |
| 4 | 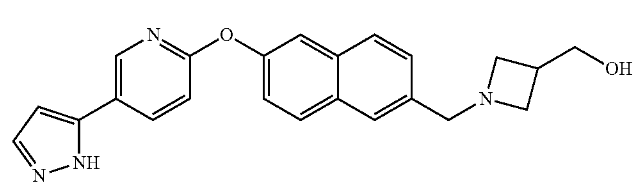 [SMILES: OCC1CN(Cc2ccc3cc(Oc4ccc(-c5ccn[nH]5)cn4)ccc3c2)C1] | (1-{6-[5-(2H-Pyrazol-3-yl)-pyridin-2-yloxy]-naphthalen-2-ylmethyl}-azetidin-3-yl)-methanol |

TABLE 1-continued

Compounds of the invention.

| Ex. | Structure | Compound Name |
|---|---|---|
| 5 | 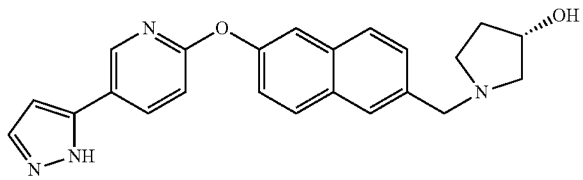 [SMILES: O[C@H]1CCN(Cc2ccc3cc(Oc4ccc(-c5ccn[nH]5)cn4)ccc3c2)C1] | (S)-1-{6-[5-(2H-Pyrazol-3-yl)-pyridin-2-yloxy]-naphthalen-2-ylmethyl}-pyrrolidin-3-ol |
| 6 | 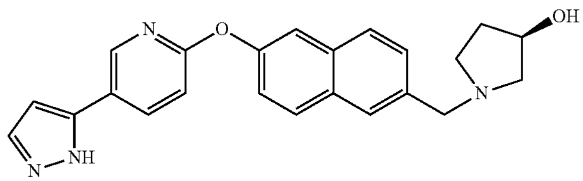 [SMILES: O[C@@H]1CCN(Cc2ccc3cc(Oc4ccc(-c5ccn[nH]5)cn4)ccc3c2)C1] | (R)-1-{6-[5-(2H-Pyrazol-3-yl)-pyridin-2-yloxy]-naphthalen-2-ylmethyl}-pyrrolidin-3-ol |
| 7 | 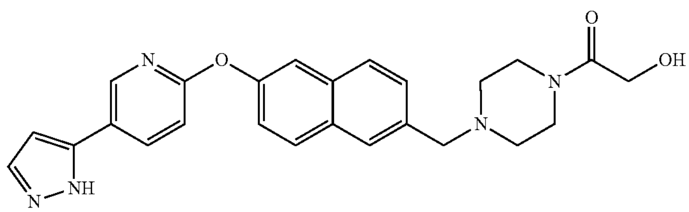 [SMILES: O=C(CO)N1CCN(Cc2ccc3cc(Oc4ccc(-c5ccn[nH]5)cn4)ccc3c2)CC1] | 2-Hydroxy-1-(4-{6-[5-(2H-pyrazol-3-yl)-pyridin-2-yloxy]-naphthalen-2-ylmethyl}-piperazin-1-yl)-ethanone |
| 8 | 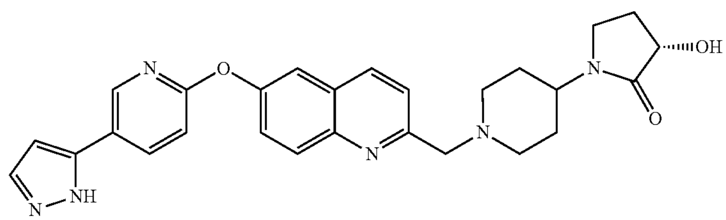 [SMILES: O=C1[C@@H](O)CCN1C1CCN(Cc2ccc3cc(Oc4ccc(-c5ccn[nH]5)cn4)ccc3n2)CC1] | (S)-3-Hydroxy-1-(1-{6-[5-(2H-pyrazol-3-yl)-pyridin-2-yloxy]-quinolin-2-ylmethyl}-piperidin-4-yl)-pyrrolidin-2-one |
| 9 | 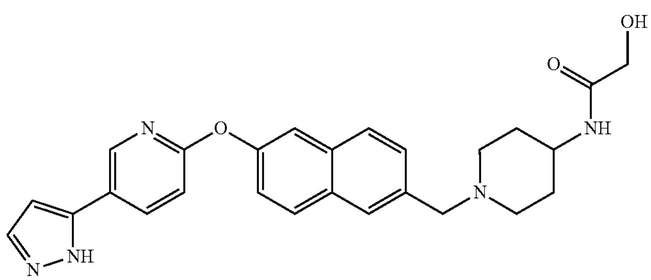 [SMILES: O=C(CO)NC1CCN(Cc2ccc3cc(Oc4ccc(-c5ccn[nH]5)cn4)ccc3c2)CC1] | 2-Hydroxy-N-(1-{6-[5-(2H-pyrazol-3-yl)-pyridin-2-yloxy]-naphthalen-2-ylmethyl}-piperidin-4-yl)-acetamide |
| 10 | 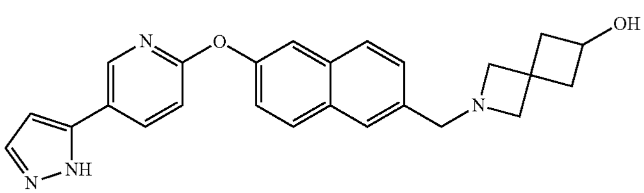 [SMILES: OC1CC2(C1)CN(Cc1ccc3cc(Oc4ccc(-c5ccn[nH]5)cn4)ccc3c1)C2] | 2-{6-[5-(2H-Pyrazol-3-yl)-pyridin-2-yloxy]-naphthalen-2-ylmethyl}-2-aza-spiro[3.3]heptan-6-ol |
| 11 | 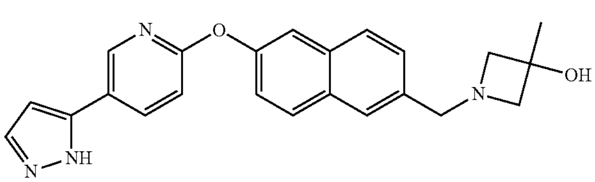 [SMILES: CC1(O)CN(Cc2ccc3cc(Oc4ccc(-c5ccn[nH]5)cn4)ccc3c2)C1] | 3-Methyl-1-{6-[5-(2H-pyrazol-3-yl)-pyridin-2-yloxy]-naphthalen-2-ylmethyl}-azetidin-3-ol |

TABLE 1-continued

Compounds of the invention.

| Ex. | Structure | Compound Name |
|---|---|---|
| 12 | 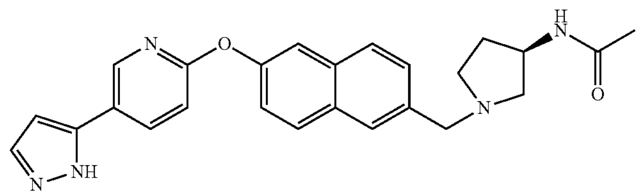 [SMILES: CC(=O)N[C@@H]1CCN(Cc2ccc3cc(Oc4ccc(-c5ccn[nH]5)cn4)ccc3c2)C1] | N-((R)-1-{6-[5-(2H-Pyrazol-3-yl)-pyridin-2-yloxy]-naphthalen-2-ylmethyl}-pyrrolidin-3-yl)-acetamide |
| 13 | 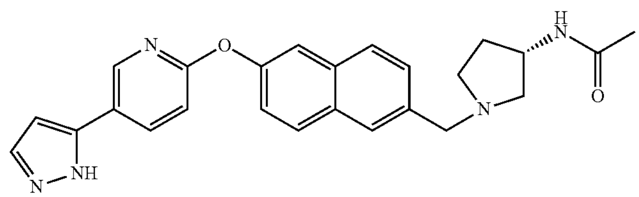 [SMILES: CC(=O)N[C@H]1CCN(Cc2ccc3cc(Oc4ccc(-c5ccn[nH]5)cn4)ccc3c2)C1] | N-((S)-1-{6-[5-(2H-Pyrazol-3-yl)-pyridin-2-yloxy]-naphthalen-2-ylmethyl}-pyrrolidin-3-yl)-acetamide |
| 14 | 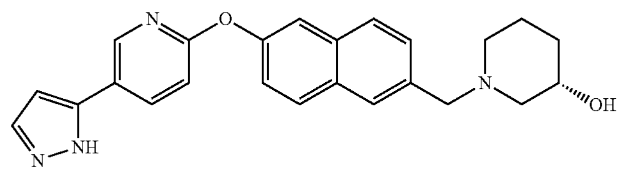 [SMILES: O[C@H]1CCCN(Cc2ccc3cc(Oc4ccc(-c5ccn[nH]5)cn4)ccc3c2)C1] | (S)-1-{6-[5-(2H-Pyrazol-3-yl)-pyridin-2-yloxy]-naphthalen-2-ylmethyl}-piperidin-3-ol |
| 15 | 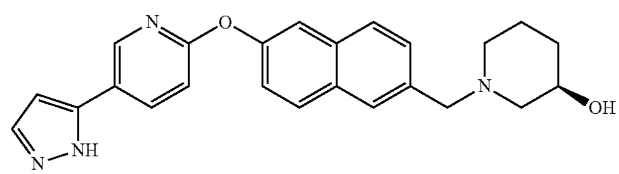 [SMILES: O[C@@H]1CCCN(Cc2ccc3cc(Oc4ccc(-c5ccn[nH]5)cn4)ccc3c2)C1] | (R)-1-{6-[5-(2H-Pyrazol-3-yl)-pyridin-2-yloxy]-naphthalen-2-ylmethyl}-piperidin-3-ol |
| 16 | 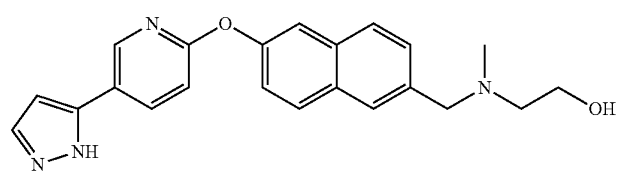 [SMILES: CN(CCO)Cc1ccc2cc(Oc3ccc(-c4ccn[nH]4)cn3)ccc2c1] | 2-(Methyl-{6-[5-(2H-pyrazol-3-yl)-pyridin-2-yloxy]-naphthalen-2-ylmethyl}-amino)-ethanol |
| 17 | 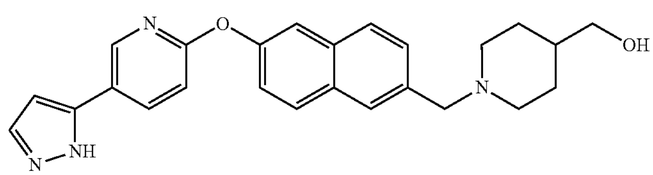 [SMILES: OCC1CCN(Cc2ccc3cc(Oc4ccc(-c5ccn[nH]5)cn4)ccc3c2)CC1] | (1-{6-[5-(2H-Pyrazol-3-yl)-pyridin-2-yloxy]-naphthalen-2-ylmethyl}-piperidin-4-yl)-methanol |
| 18 | 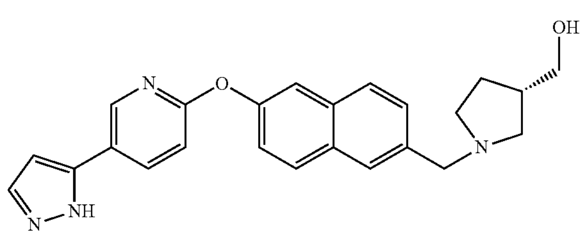 [SMILES: OC[C@H]1CCN(Cc2ccc3cc(Oc4ccc(-c5ccn[nH]5)cn4)ccc3c2)C1] | ((S)-1-{6-[5-(2H-Pyrazol-3-yl)-pyridin-2-yloxy]-naphthalen-2-ylmethyl}-pyrrolidin-3-yl)-methanol |
| 19 | 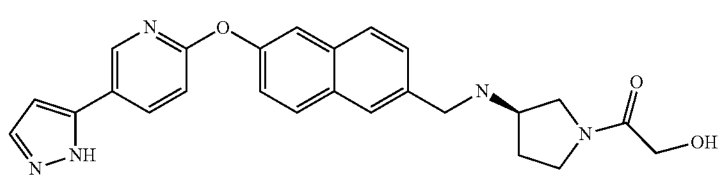 [SMILES: O=C(CO)N1CC[C@@H](NCc2ccc3cc(Oc4ccc(-c5ccn[nH]5)cn4)ccc3c2)C1] | 2-Hydroxy-1-[(R)-3-(methyl-{6-[5-(2H-pyrazol-3-yl)-pyridin-2-yloxy]-naphthalen-2-ylmethyl}-amino)-pyrrolidin-1-yl]-ethanone |

TABLE 1-continued

Compounds of the invention.

| Ex. | Structure | Compound Name |
|---|---|---|
| 20 | 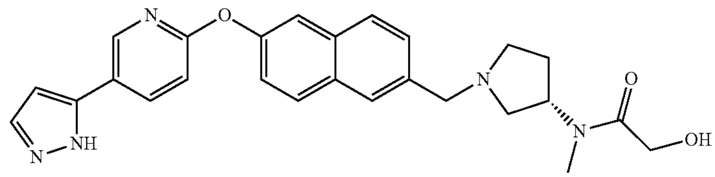 [SMILES: CN(C(=O)CO)[C@H]1CCN(Cc2ccc3cc(Oc4ccc(-c5ccn[nH]5)cn4)ccc3c2)C1] | 2-Hydroxy-N-methyl-N-((S)-1-{6-[5-(2H-pyrazol-3-yl)-pyridin-2-yloxy]-naphthalen-2-ylmethyl}-pyrrolidin-3-yl)-acetamide |
| 21 | 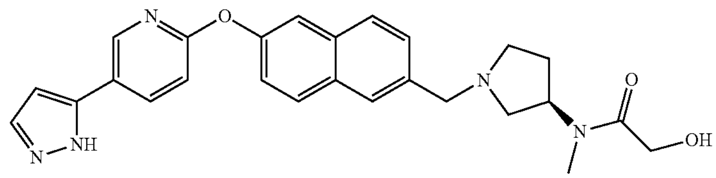 [SMILES: CN(C(=O)CO)[C@@H]1CCN(Cc2ccc3cc(Oc4ccc(-c5ccn[nH]5)cn4)ccc3c2)C1] | 2-Hydroxy-N-methyl-N-((R)-1-{6-[5-(2H-pyrazol-3-yl)-pyridin-2-yloxy]-naphthalen-2-ylmethyl}-pyrrolidin-3-yl)-acetamide |
| 22 | 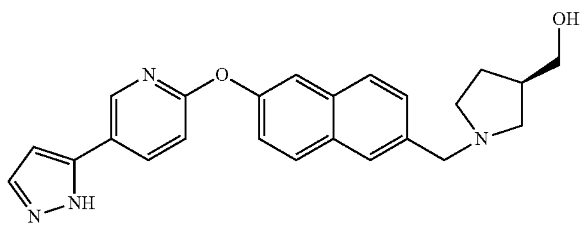 [SMILES: OC[C@@H]1CCN(Cc2ccc3cc(Oc4ccc(-c5ccn[nH]5)cn4)ccc3c2)C1] | ((R)-1-{6-[5-(2H-Pyrazol-3-yl)-pyridin-2-yloxy]-naphthalen-2-ylmethyl}-pyrrolidin-3-yl)-methanol |
| 23 | 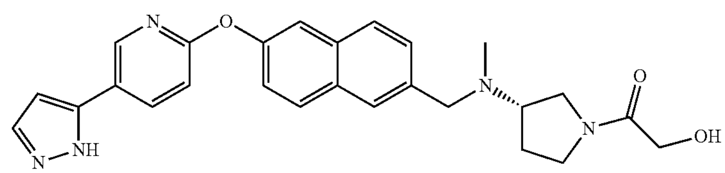 [SMILES: CN(Cc1ccc2cc(Oc3ccc(-c4ccn[nH]4)cn3)ccc2c1)[C@H]1CCN(C(=O)CO)C1] | 2-Hydroxy-1-[(S)-3-(methyl-{6-[5-(2H-pyrazol-3-yl)-pyridin-2-yloxy]-naphthalen-2-ylmethyl}-amino)-pyrrolidin-1-yl]-ethanone |
| 24 | 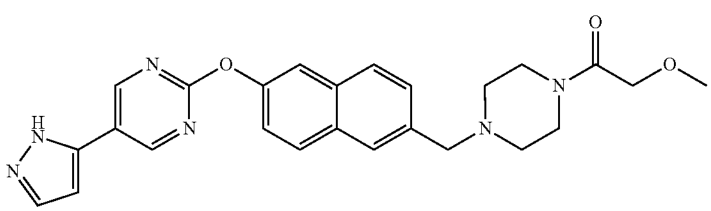 [SMILES: COCC(=O)N1CCN(Cc2ccc3cc(Oc4ncc(-c5ccn[nH]5)cn4)ccc3c2)CC1] | 2-Methoxy-1-(4-{6-[5-(2H-pyrazol-3-yl)-pyrimidin-2-yloxy]-naphthalen-2-ylmethyl}-piperazin-1-yl)-ethanone |
| 25 | 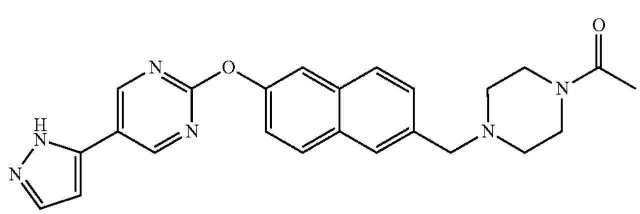 [SMILES: CC(=O)N1CCN(Cc2ccc3cc(Oc4ncc(-c5ccn[nH]5)cn4)ccc3c2)CC1] | 1-(4-{6-[5-(2H-Pyrazol-3-yl)-pyrimidin-2-yloxy]-naphthalen-2-ylmethyl}-piperazin-1-yl)-ethanone |
| 26 | 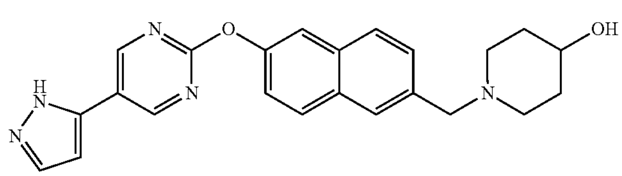 [SMILES: OC1CCN(Cc2ccc3cc(Oc4ncc(-c5ccn[nH]5)cn4)ccc3c2)CC1] | 1-{6-[5-(2H-Pyrazol-3-yl)-pyrimidin-2-yloxy]-naphthalen-2-ylmethyl}-piperidin-4-ol |

TABLE 1-continued

Compounds of the invention.

| Ex. | Structure | Compound Name |
|-----|-----------|---------------|
| 27 | 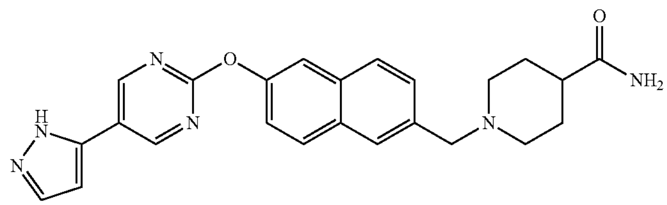 [SMILES: NC(=O)C1CCN(Cc2ccc3cc(Oc4ncc(-c5ccn[nH]5)cn4)ccc3c2)CC1] | 1-{6-[5-(2H-Pyrazol-3-yl)-pyrimidin-2-yloxy]-naphthalen-2-ylmethyl}-piperidine-4-carboxylic acid amide |
| 28 | 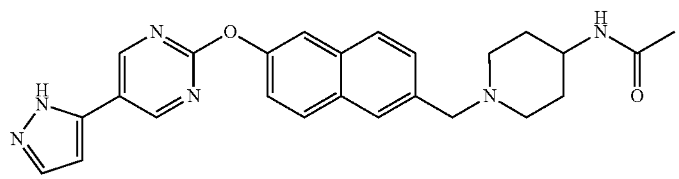 [SMILES: CC(=O)NC1CCN(Cc2ccc3cc(Oc4ncc(-c5ccn[nH]5)cn4)ccc3c2)CC1] | N-(1-{6-[5-(2H-Pyrazol-3-yl)-pyrimidin-2-yloxy]-naphthalen-2-ylmethyl}-piperidin-4-yl)-acetamide |
| 29 | 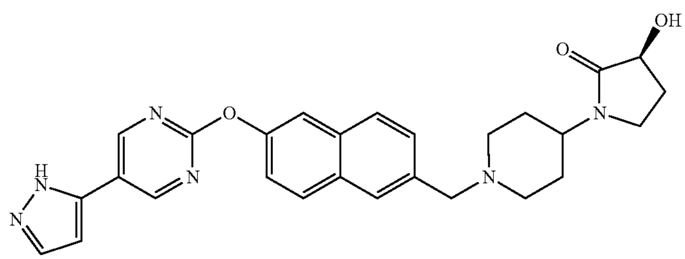 [SMILES: O=C1[C@@H](O)CCN1C1CCN(Cc2ccc3cc(Oc4ncc(-c5ccn[nH]5)cn4)ccc3c2)CC1] | (S)-3-Hydroxy-1-(1-{6-[5-(2H-pyrazol-3-yl)-pyrimidin-2-yloxy]-naphthalen-2-ylmethyl}-piperidin-4-yl)-pyrrolidin-2-one |
| 30 | 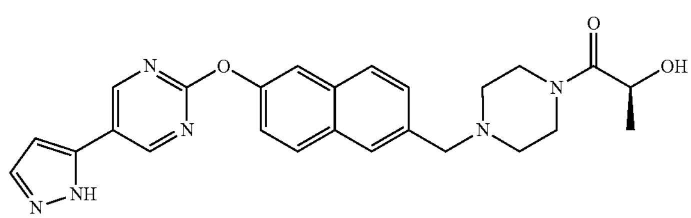 [SMILES: C[C@H](O)C(=O)N1CCN(Cc2ccc3cc(Oc4ncc(-c5ccn[nH]5)cn4)ccc3c2)CC1] | (S)-2-Hydroxy-1-(4-{6-[5-(2H-pyrazol-3-yl)-pyrimidin-2-yloxy]-naphthalen-2-ylmethyl}-piperazin-1-yl)-propan-1-one |
| 31 | 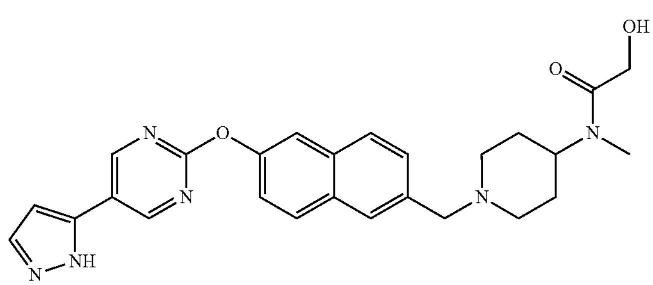 [SMILES: CN(C(=O)CO)C1CCN(Cc2ccc3cc(Oc4ncc(-c5ccn[nH]5)cn4)ccc3c2)CC1] | 2-Hydroxy-N-methyl-N-(1-{6-[5-(2H-pyrazol-3-yl)-pyrimidin-2-yloxy]-naphthalen-2-ylmethyl}-piperidin-4-yl)-acetamide |
| 32 | 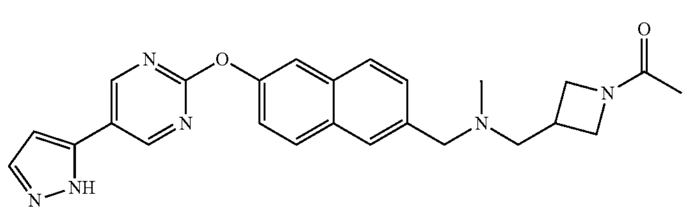 [SMILES: CC(=O)N1CC(CN(C)Cc2ccc3cc(Oc4ncc(-c5ccn[nH]5)cn4)ccc3c2)C1] | 1-{3-[(Methyl-{6-[5-(2H-pyrazol-3-yl)-pyrimidin-2-yloxy]-naphthalen-2-ylmethyl}-amino)-methyl]-azetidin-1-yl}-ethanone |

TABLE 1-continued

Compounds of the invention.

| Ex. | Structure | Compound Name |
|---|---|---|
| 33 | 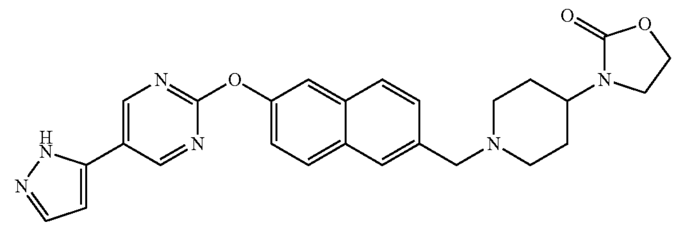 [SMILES: O=C1OCCN1C1CCN(Cc2ccc3cc(Oc4ncc(-c5ccn[nH]5)cn4)ccc3c2)CC1] | 3-(1-{6-[5-(2H-Pyrazol-3-yl)-pyrimidin-2-yloxy]-naphthalen-2-ylmethyl}-piperidin-4-yl)-oxazolidin-2-one |
| 34 | 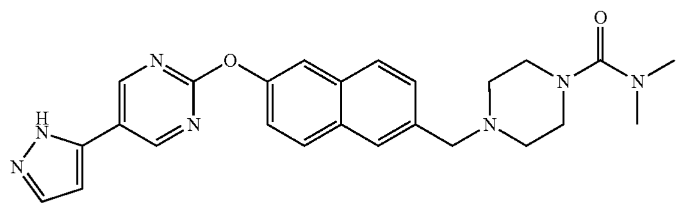 [SMILES: CN(C)C(=O)N1CCN(Cc2ccc3cc(Oc4ncc(-c5ccn[nH]5)cn4)ccc3c2)CC1] | 4-{6-[5-(2H-Pyrazol-3-yl)-pyrimidin-2-yloxy]-naphthalen-2-ylmethyl}-piperazine-1-carboxylic acid dimethylamide |
| 35 | 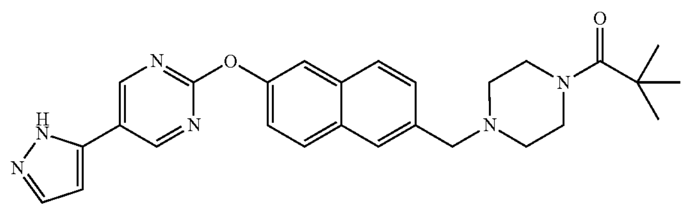 [SMILES: CC(C)(C)C(=O)N1CCN(Cc2ccc3cc(Oc4ncc(-c5ccn[nH]5)cn4)ccc3c2)CC1] | 2,2-Dimethyl-1-(4-{6-[5-(2H-pyrazol-3-yl)-pyrimidin-2-yloxy]-naphthalen-2-ylmethyl}-piperazin-1-yl)-propan-1-one |
| 36 | 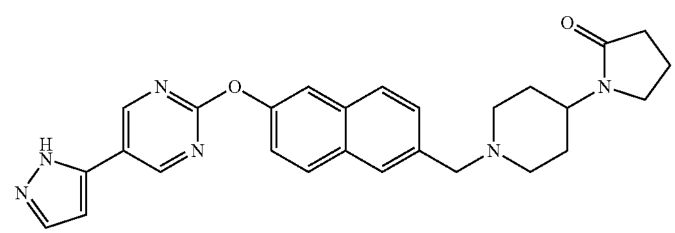 [SMILES: O=C1CCCN1C1CCN(Cc2ccc3cc(Oc4ncc(-c5ccn[nH]5)cn4)ccc3c2)CC1] | 1-(1-{6-[5-(2H-Pyrazol-3-yl)-pyrimidin-2-yloxy]-naphthalen-2-ylmethyl}-piperidin-4-yl)-pyrrolidin-2-one |
| 37 | 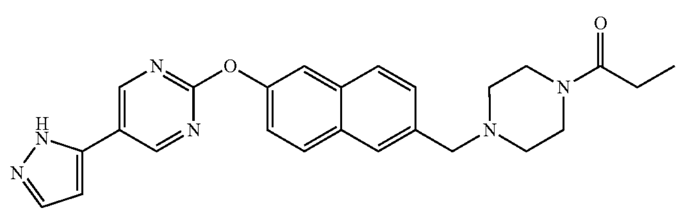 [SMILES: CCC(=O)N1CCN(Cc2ccc3cc(Oc4ncc(-c5ccn[nH]5)cn4)ccc3c2)CC1] | 1-(4-{6-[5-(2H-Pyrazol-3-yl)-pyrimidin-2-yloxy]-naphthalen-2-ylmethyl}-piperazin-1-yl)-propan-1-one |
| 38 | 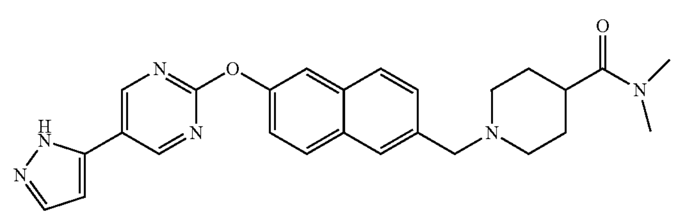 [SMILES: CN(C)C(=O)C1CCN(Cc2ccc3cc(Oc4ncc(-c5ccn[nH]5)cn4)ccc3c2)CC1] | 1-{6-[5-(2H-Pyrazol-3-yl)-pyrimidin-2-yloxy]-naphthalen-2-ylmethyl}-piperidine-4-carboxylic acid dimethylamide |
| 39 | 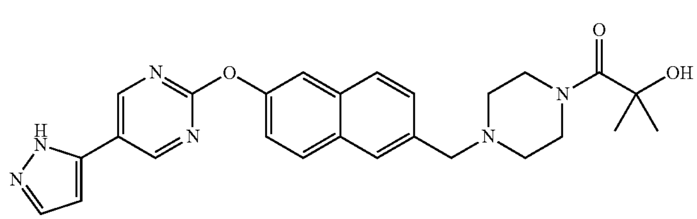 [SMILES: CC(C)(O)C(=O)N1CCN(Cc2ccc3cc(Oc4ncc(-c5ccn[nH]5)cn4)ccc3c2)CC1] | 2-Hydroxy-2-methyl-1-(4-{6-[5-(2H-pyrazol-3-yl)-pyrimidin-2-yloxy]-naphthalen-2-ylmethyl}-piperazin-1-yl)-propan-1-one |

TABLE 1-continued

Compounds of the invention.

| Ex. | Structure | Compound Name |
|---|---|---|
| 40 | 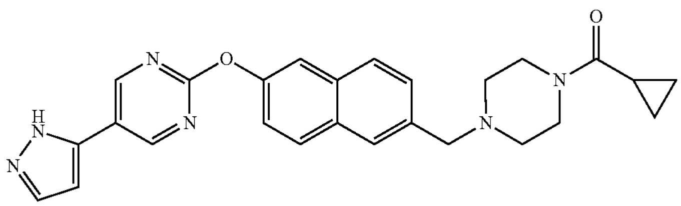 [SMILES: O=C(C1CC1)N1CCN(Cc2ccc3cc(Oc4ncc(-c5ccn[nH]5)cn4)ccc3c2)CC1] | Cyclopropyl-(4-{6-[5-(2H-pyrazol-3-yl)-pyrimidin-2-yloxy]-naphthalen-2-ylmethyl}-piperazin-1-yl)-methanone |
| 41 | 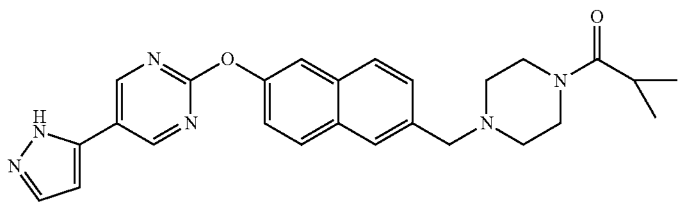 [SMILES: CC(C)C(=O)N1CCN(Cc2ccc3cc(Oc4ncc(-c5ccn[nH]5)cn4)ccc3c2)CC1] | 2-Methyl-1-(4-{6-[5-(2H-pyrazol-3-yl)-pyrimidin-2-yloxy]-naphthalen-2-ylmethyl}-piperazin-1-yl)-propan-1-one |
| 42 | 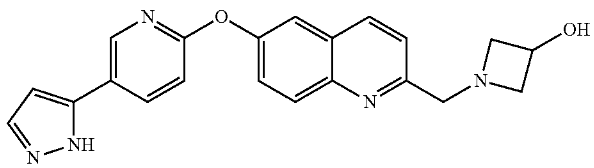 [SMILES: OC1CN(Cc2ccc3cc(Oc4ccc(-c5ccn[nH]5)cn4)ccc3n2)C1] | 1-{6-[5-(2H-Pyrazol-3-yl)-pyridin-2-yloxy]-quinolin-2-ylmethyl}-azetidin-3-ol |
| 43 | 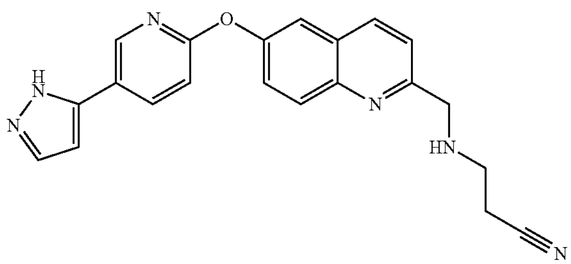 [SMILES: N#CCCNCc1ccc2cc(Oc3ccc(-c4ccn[nH]4)cn3)ccc2n1] | 3-({6-[5-(2H-Pyrazol-3-yl)-pyridin-2-yloxy]-quinolin-2-ylmethyl}-amino)-propionitrile |
| 44 | 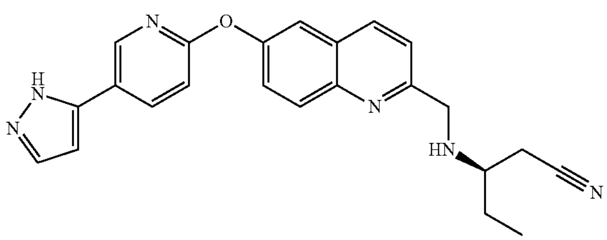 [SMILES: CC[C@H](CC#N)NCc1ccc2cc(Oc3ccc(-c4ccn[nH]4)cn3)ccc2n1] | (R)-3-({6-[5-(2H-Pyrazol-3-yl)-pyridin-2-yloxy]-quinolin-2-ylmethyl}-amino)-pentanenitrile |
| 45 | 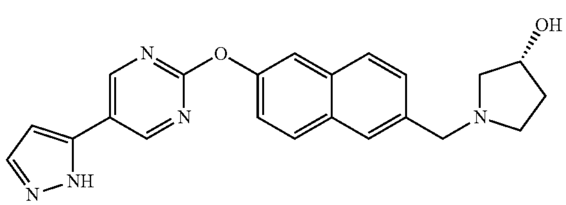 [SMILES: O[C@@H]1CCN(Cc2ccc3cc(Oc4ncc(-c5ccn[nH]5)cn4)ccc3c2)C1] | (R)-1-{6-[5-(2H-Pyrazol-3-yl)-pyrimidin-2-yloxy]-naphthalen-2-ylmethyl}-pyrrolidin-3-ol |
| 46 | 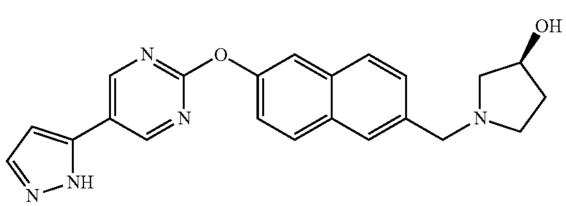 [SMILES: O[C@H]1CCN(Cc2ccc3cc(Oc4ncc(-c5ccn[nH]5)cn4)ccc3c2)C1] | (S)-1-{6-[5-(2H-Pyrazol-3-yl)-pyrimidin-2-yloxy]-naphthalen-2-ylmethyl}-pyrrolidin-3-ol |

TABLE 1-continued

Compounds of the invention.

| Ex. | Structure | Compound Name |
|---|---|---|
| 47 | 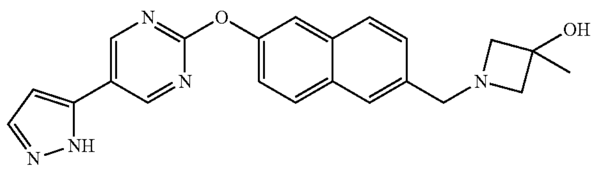 [SMILES: CC1(O)CN(Cc2ccc3cc(Oc4ncc(-c5ccn[nH]5)cn4)ccc3c2)C1] | 3-Methyl-1-{6-[5-(2H-pyrazol-3-yl)-pyrimidin-2-yloxy]-naphthalen-2-ylmethyl}-azetidin-3-ol |
| 48 | 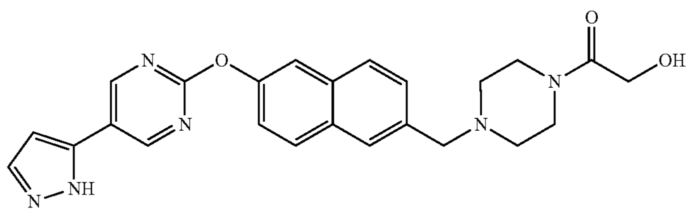 [SMILES: O=C(CO)N1CCN(Cc2ccc3cc(Oc4ncc(-c5ccn[nH]5)cn4)ccc3c2)CC1] | 2-Hydroxy-1-(4-{6-[5-(2H-pyrazol-3-yl)-pyrimidin-2-yloxy]-naphthalen-2-ylmethyl}-piperazin-1-yl)-ethanone |
| 49 | 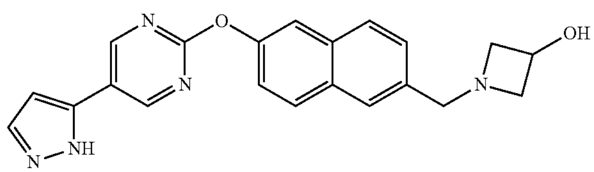 [SMILES: OC1CN(Cc2ccc3cc(Oc4ncc(-c5ccn[nH]5)cn4)ccc3c2)C1] | 1-{6-[5-(2H-Pyrazol-3-yl)-pyrimidin-2-yloxy]-naphthalen-2-ylmethyl}-azetidin-3-ol |
| 50 | 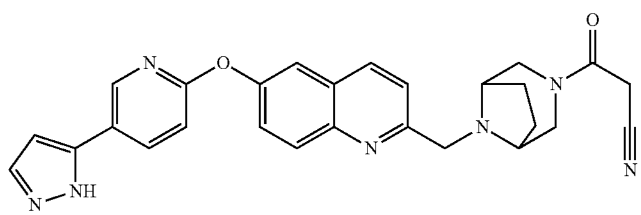 [SMILES: N#CCC(=O)N1CC2CCC(C1)N2Cc1ccc2cc(Oc3ccc(-c4ccn[nH]4)cn3)ccc2n1] | 3-Oxo-3-(8-{6-[5-(2H-pyrazol-3-yl)-pyridin-2-yloxy]-quinolin-2-ylmethyl}-3,8-diaza-bicyclo[3.2.1]oct-3-yl)-propionitrile |
| 51 | 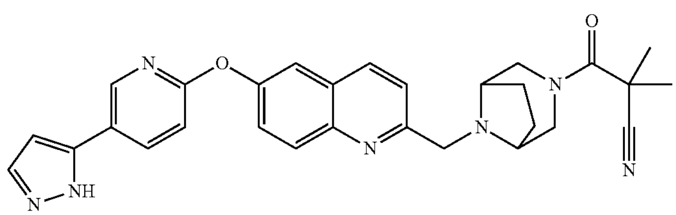 [SMILES: CC(C)(C#N)C(=O)N1CC2CCC(C1)N2Cc1ccc2cc(Oc3ccc(-c4ccn[nH]4)cn3)ccc2n1] | 2,2-Dimethyl-3-oxo-3-(8-{6-[5-(2H-pyrazol-3-yl)-pyridin-2-yloxy]-quinolin-2-ylmethyl}-3,8-diaza-bicyclo[3.2.1]oct-3-yl)-propionitrile |
| 52 | 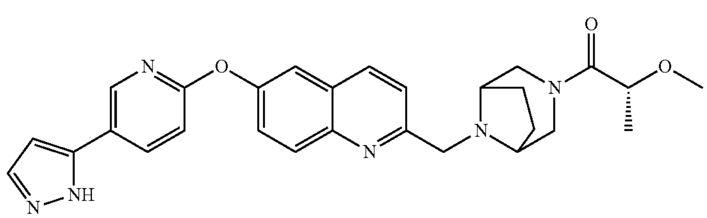 [SMILES: CO[C@H](C)C(=O)N1CC2CCC(C1)N2Cc1ccc2cc(Oc3ccc(-c4ccn[nH]4)cn3)ccc2n1] | (R)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one |
| 53 | 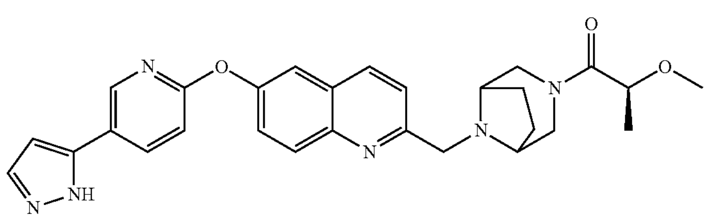 [SMILES: CO[C@@H](C)C(=O)N1CC2CCC(C1)N2Cc1ccc2cc(Oc3ccc(-c4ccn[nH]4)cn3)ccc2n1] | (S)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one |

TABLE 1-continued

Compounds of the invention.

| Ex. | Structure | Compound Name |
|---|---|---|
| 54 | 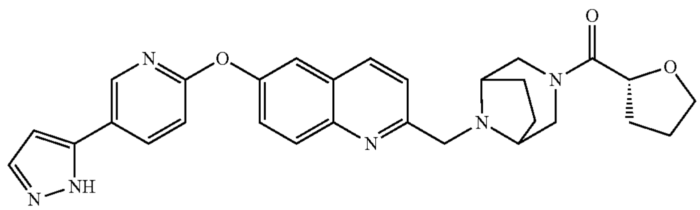 [SMILES: O=C([C@H]1CCCO1)N1CC2CCC(C1)N2Cc1ccc2cc(Oc3ccc(-c4ccn[nH]4)cn3)ccc2n1] | (8-{6-[5-(2H-Pyrazol-3-yl)-pyridin-2-yloxy]-quinolin-2-ylmethyl}-3,8-diaza-bicyclo[3.2.1]oct-3-yl)-(R)-tetrahydro-furan-2-yl-methanone |
| 55 | 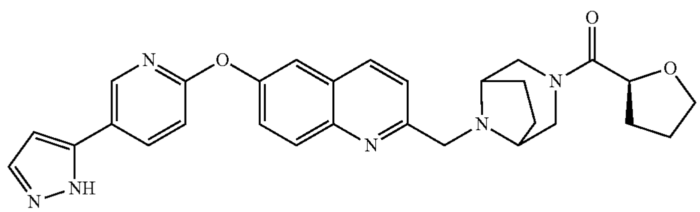 [SMILES: O=C([C@@H]1CCCO1)N1CC2CCC(C1)N2Cc1ccc2cc(Oc3ccc(-c4ccn[nH]4)cn3)ccc2n1] | (8-{6-[5-(2H-Pyrazol-3-yl)-pyridin-2-yloxy]-quinolin-2-ylmethyl}-3,8-diaza-bicyclo[3.2.1]oct-3-yl)-(S)-tetrahydro-furan-2-yl-methanone |
| 56 | 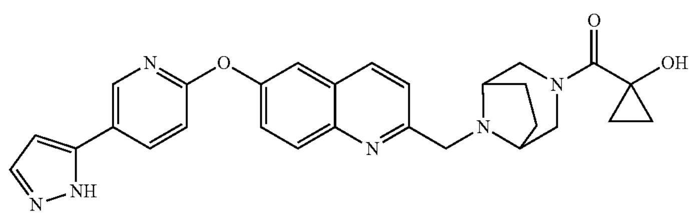 [SMILES: O=C(N1CC2CCC(C1)N2Cc1ccc2cc(Oc3ccc(-c4ccn[nH]4)cn3)ccc2n1)C1(O)CC1] | (1-Hydroxy-cyclopropyl)-(8-{6-[5-(2H-pyrazol-3-yl)-pyridin-2-yloxy]-quinolin-2-ylmethyl}-3,8-diaza-bicyclo[3.2.1]oct-3-yl)-methanone |
| 57 | 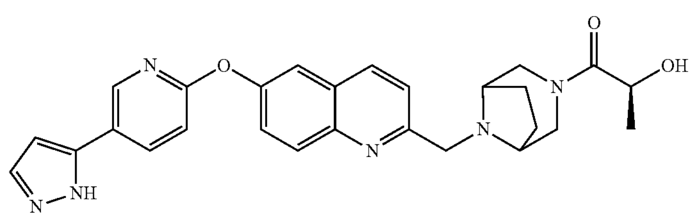 [SMILES: C[C@H](O)C(=O)N1CC2CCC(C1)N2Cc1ccc2cc(Oc3ccc(-c4ccn[nH]4)cn3)ccc2n1] | (S)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one |
| 58 | 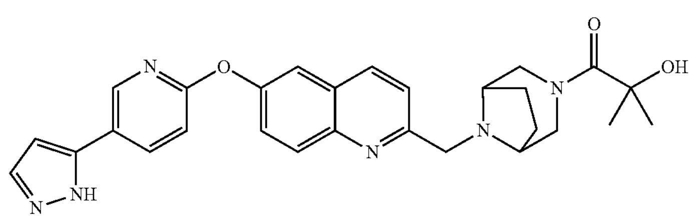 [SMILES: CC(C)(O)C(=O)N1CC2CCC(C1)N2Cc1ccc2cc(Oc3ccc(-c4ccn[nH]4)cn3)ccc2n1] | 2-Hydroxy-2-methyl-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one |
| 59 | 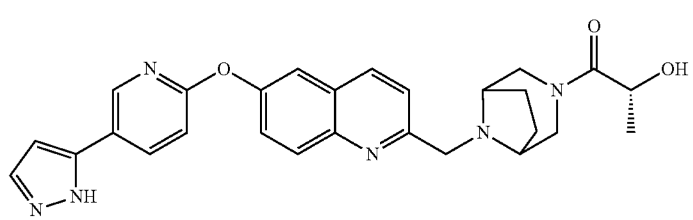 [SMILES: C[C@@H](O)C(=O)N1CC2CCC(C1)N2Cc1ccc2cc(Oc3ccc(-c4ccn[nH]4)cn3)ccc2n1] | (R)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one |
| 60 | 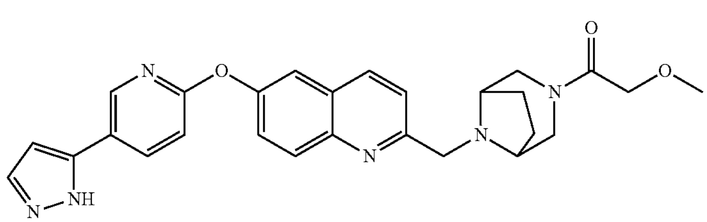 | 2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone |

TABLE 1-continued

Compounds of the invention.

| Ex. | Structure | Compound Name |
|---|---|---|
| 61 | 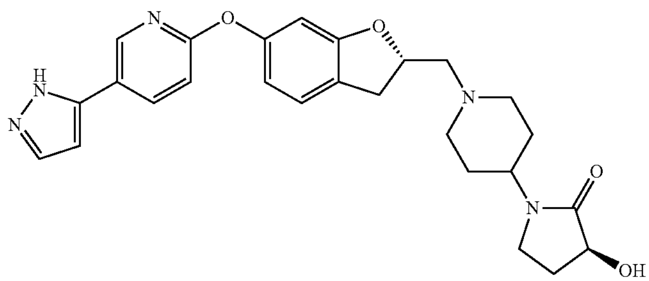 [SMILES: O=C1[C@@H](O)CCN1C1CCN(C[C@@H]2Cc3ccc(Oc4ccc(-c5ccn[nH]5)cn4)cc3O2)CC1] | (S)-3-Hydroxy-1-(1-{(S)-6-[5-(2H-pyrazol-3-yl)-pyridin-2-yloxy]-2,3-dihydro-benzofuran-2-ylmethyl}-piperidin-4-yl)-pyrrolidin-2-one |
| 62 | 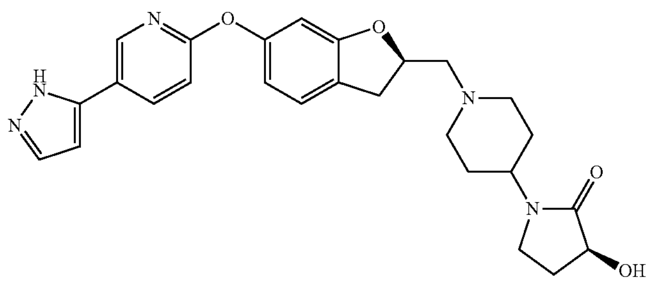 [SMILES: O=C1[C@@H](O)CCN1C1CCN(C[C@H]2Cc3ccc(Oc4ccc(-c5ccn[nH]5)cn4)cc3O2)CC1] | (S)-3-Hydroxy-1-(1-{(R)-6-[5-(2H-pyrazol-3-yl)-pyridin-2-yloxy]-2,3-dihydro-benzofuran-2-ylmethyl}-piperidin-4-yl)-pyrrolidin-2-one |
| 63 | 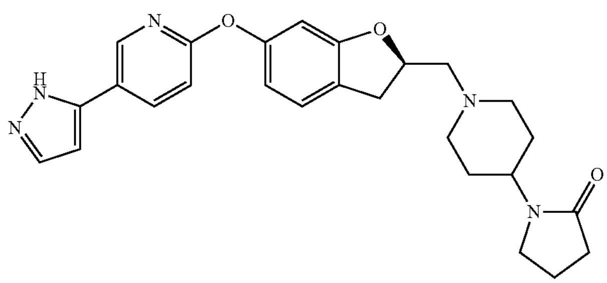 [SMILES: O=C1CCCN1C1CCN(C[C@H]2Cc3ccc(Oc4ccc(-c5ccn[nH]5)cn4)cc3O2)CC1] | 1-(1-{(R)-6-[5-(2H-Pyrazol-3-yl)-pyridin-2-yloxy]-2,3-dihydro-benzofuran-2-ylmethyl}-piperidin-4-yl)-pyrrolidin-2-one |
| 64 | 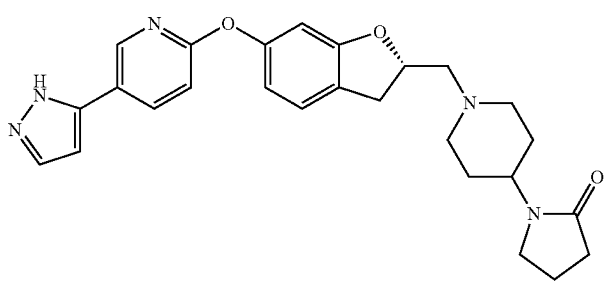 [SMILES: O=C1CCCN1C1CCN(C[C@@H]2Cc3ccc(Oc4ccc(-c5ccn[nH]5)cn4)cc3O2)CC1] | 1-(1-{(S)-6-[5-(2H-Pyrazol-3-yl)-pyridin-2-yloxy]-2,3-dihydro-benzofuran-2-ylmethyl}-piperidin-4-yl)-pyrrolidin-2-one |
| 65 | 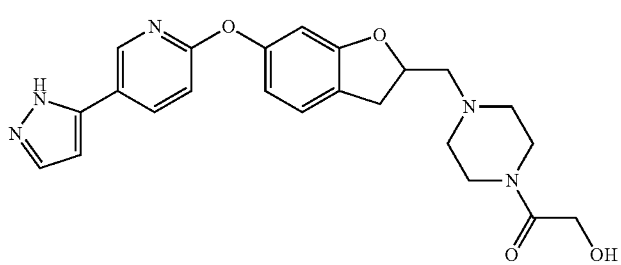 [SMILES: O=C(CO)N1CCN(CC2Cc3ccc(Oc4ccc(-c5ccn[nH]5)cn4)cc3O2)CC1] | 2-Hydroxy-1-(4-{6-[5-(2H-pyrazol-3-yl)-pyridin-2-yloxy]-2,3-dihydro-benzofuran-2-ylmethyl}-piperazin-1-yl)-ethanone |

TABLE 1-continued

Compounds of the invention.

| Ex. | Structure | Compound Name |
|---|---|---|
| 66 | 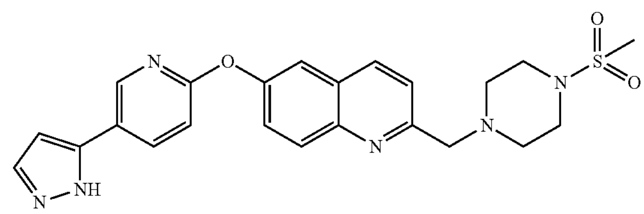 [SMILES: CS(=O)(=O)N1CCN(Cc2ccc3cc(Oc4ccc(-c5ccn[nH]5)cn4)ccc3n2)CC1] | 2-(4-Methanesulfonyl-piperazin-1-ylmethyl)-6-[5-(2H-pyrazol-3-yl)-pyridin-2-yloxy]-quinoline |
| 67 | 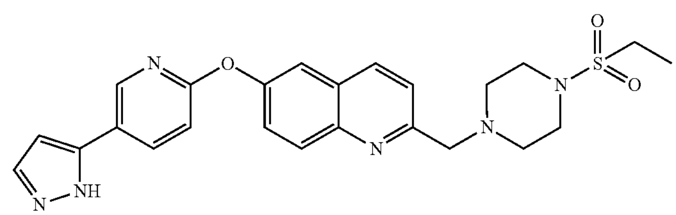 [SMILES: CCS(=O)(=O)N1CCN(Cc2ccc3cc(Oc4ccc(-c5ccn[nH]5)cn4)ccc3n2)CC1] | 2-(4-Ethanesulfonyl-piperazin-1-ylmethyl)-6-[5-(2H-pyrazol-3-yl)-pyridin-2-yloxy]-quinoline |
| 68 | 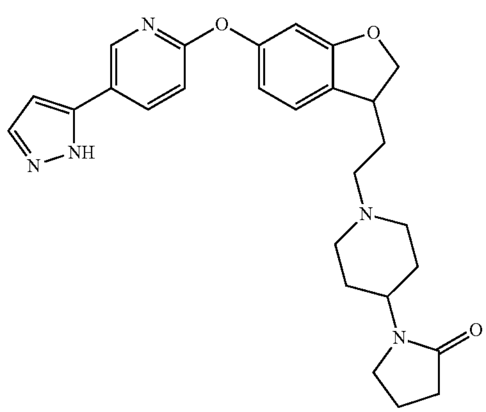 [SMILES: O=C1CCCN1C1CCN(CCC2COc3cc(Oc4ccc(-c5ccn[nH]5)cn4)ccc32)CC1] | 1-[1-(2-{6-[5-(2H-Pyrazol-3-yl)-pyridin-2-yloxy]-2,3-dihydro-benzofuran-3-yl}-ethyl)-piperidin-4-yl]-pyrrolidin-2-one |
| 69 | 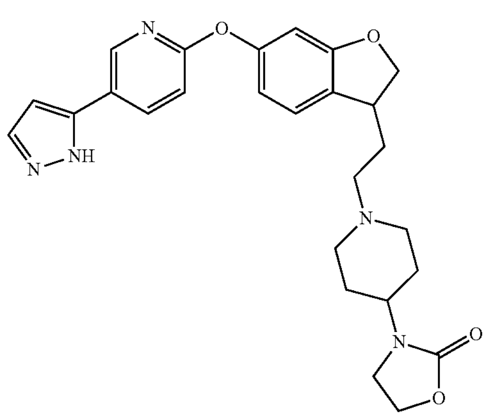 | 3-[1-(2-{6-[5-(2H-Pyrazol-3-yl)-pyridin-2-yloxy]-2,3-dihydro-benzofuran-3-yl}-ethyl)-piperidin-4-yl]-oxazolidin-2-one |

TABLE 1-continued

Compounds of the invention.

| Ex. | Structure | Compound Name |
|---|---|---|
| 70 | 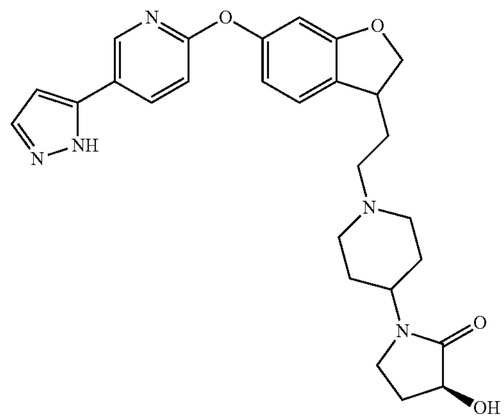 [SMILES: O=C1[C@@H](O)CCN1C1CCN(CCC2COc3cc(Oc4ccc(-c5ccn[nH]5)cn4)ccc32)CC1] | (S)-3-Hydroxy-1-[1-(2-{6-[5-(2H-pyrazol-3-yl)-pyridin-2-yloxy]-2,3-dihydro-benzofuran-3-yl}-ethyl)-piperidin-4-yl]-pyrrolidin-2-one |
| 71 | 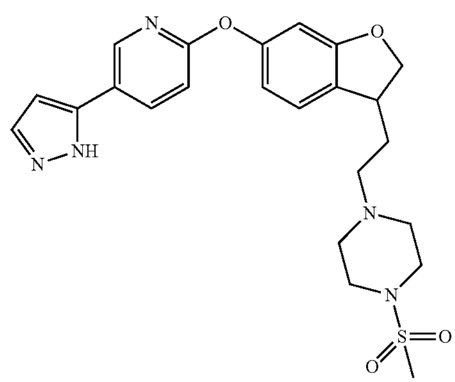 [SMILES: CS(=O)(=O)N1CCN(CCC2COc3cc(Oc4ccc(-c5ccn[nH]5)cn4)ccc32)CC1] | 1-Methanesulfonyl-4-(2-{6-[5-(2H-pyrazol-3-yl)-pyridin-2-yloxy]-2,3-dihydro-benzofuran-3-yl}-ethyl)-piperazine |
| 72 | 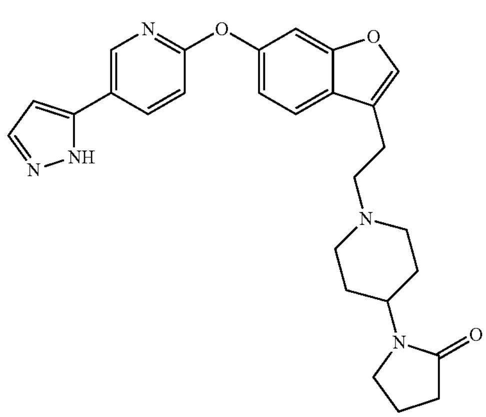 [SMILES: O=C1CCCN1C1CCN(CCc2coc3cc(Oc4ccc(-c5ccn[nH]5)cn4)ccc23)CC1] | 1-[1-(2-{6-[5-(2H-Pyrazol-3-yl)-pyridin-2-yloxy]-benzofuran-3-yl}-ethyl)-piperidin-4-yl]-pyrrolidin-2-one |

TABLE 1-continued
Compounds of the invention.
| Ex. | Structure | Compound Name |
|---|---|---|
| 73 | 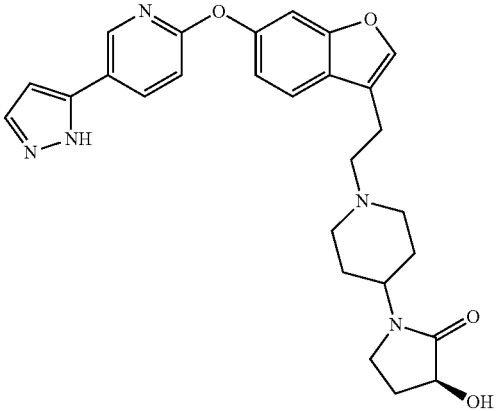 [SMILES: O=C1[C@@H](O)CCN1C1CCN(CCc2coc3cc(Oc4ccc(-c5ccn[nH]5)cn4)ccc23)CC1] | (S)-3-Hydroxy-1-[1-(2-{6-[5-(2H-pyrazol-3-yl)-pyridin-2-yloxy]-benzofuran-3-yl}-ethyl)-piperidin-4-yl]-pyrrolidin-2-one |
| 74 | 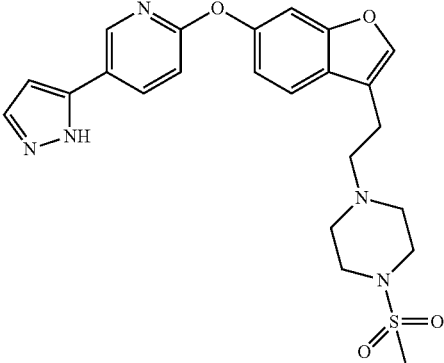 [SMILES: CS(=O)(=O)N1CCN(CCc2coc3cc(Oc4ccc(-c5ccn[nH]5)cn4)ccc23)CC1] | 1-Methanesulfonyl-4-(2-{6-[5-(2H-pyrazol-3-yl)-pyridin-2-yloxy]-benzofuran-3-yl}-ethyl)-piperazine |
| 75 | 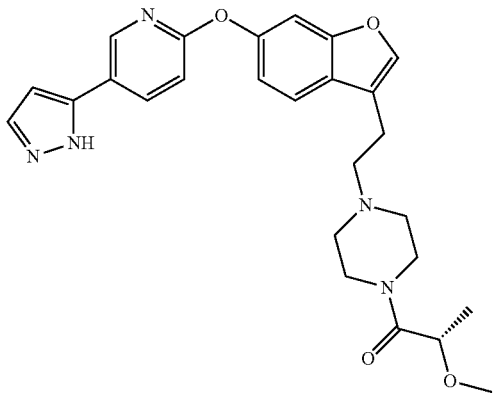 | (S)-2-Methoxy-1-[4-(2-{6-[5-(2H-pyrazol-3-yl)-pyridin-2-yloxy]-benzofuran-3-yl}-ethyl)-piperazin-1-yl]-propan-1-one |

TABLE 1-continued

Compounds of the invention.

| Ex. | Structure | Compound Name |
|---|---|---|
| 76 | 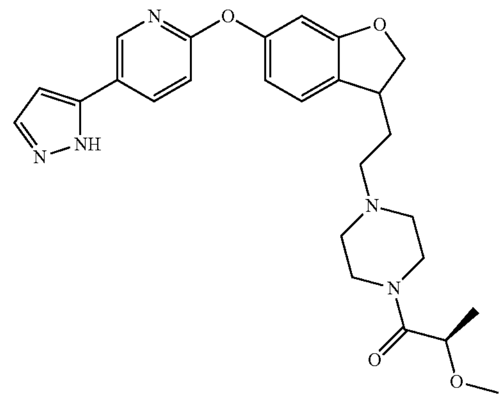 [SMILES: CO[C@H](C)C(=O)N1CCN(CCC2COc3cc(Oc4ccc(-c5ccn[nH]5)cn4)ccc32)CC1] | (R)-2-Methoxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one |
| 77 | 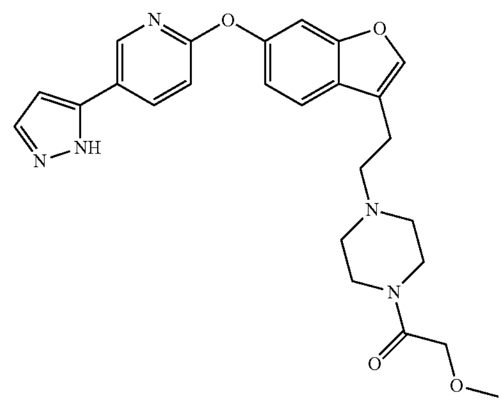 [SMILES: COCC(=O)N1CCN(CCc2coc3cc(Oc4ccc(-c5ccn[nH]5)cn4)ccc23)CC1] | 2-Methoxy-1-[4-(2-{6-[5-(2H-pyrazol-3-yl)-pyridin-2-yloxy]-benzofuran-3-yl}-ethyl)-piperazin-1-yl]-ethanone |
| 78 | 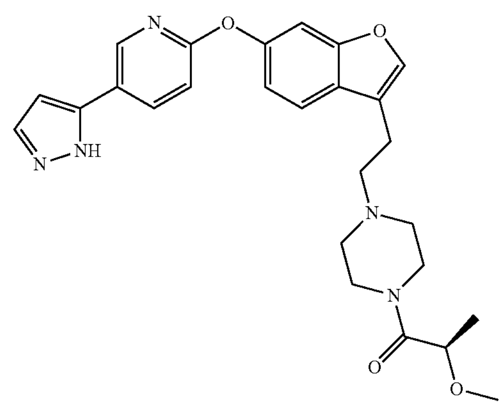 [SMILES: CO[C@H](C)C(=O)N1CCN(CCc2coc3cc(Oc4ccc(-c5ccn[nH]5)cn4)ccc23)CC1] | (R)-2-Methoxy-1-[4-(2-{6-[5-(2H-pyrazol-3-yl)-pyridin-2-yloxy]-benzofuran-3-yl}-ethyl)-piperazin-1-yl]-propan-1-one |
| 79 | 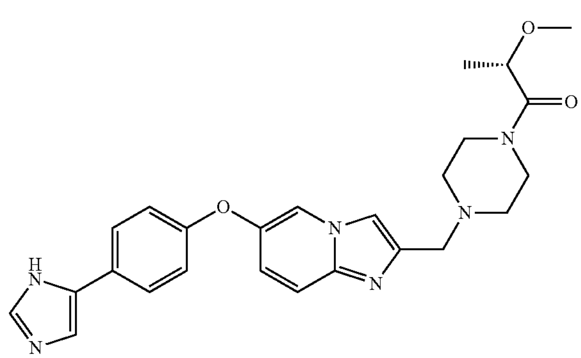 [SMILES: CO[C@@H](C)C(=O)N1CCN(Cc2cn3cc(Oc4ccc(-c5cnc[nH]5)cc4)ccc3n2)CC1] | (S)-2-Methoxy-1-(4-{6-[4-(2H-pyrazol-3-yl)-phenoxy]-imidazo[1,2-a]pyridin-2-ylmethyl}-piperazin-1-yl)-propan-1-one |

TABLE 1-continued

Compounds of the invention.

| Ex. | Structure | Compound Name |
| --- | --- | --- |
| 80 | 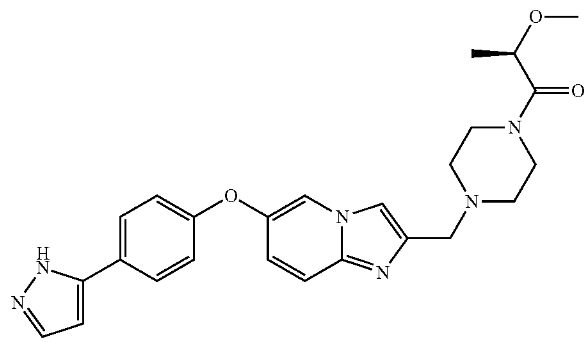 [SMILES: CO[C@H](C)C(=O)N1CCN(Cc2cn3cc(Oc4ccc(-c5ccn[nH]5)cc4)ccc3n2)CC1] | (R)-2-Methoxy-1-(4-{6-[4-(2H-pyrazol-3-yl)-phenoxy]-imidazo[1,2-a]pyridin-2-ylmethyl}-piperazin-1-yl)-propan-1-one |
| 81 | 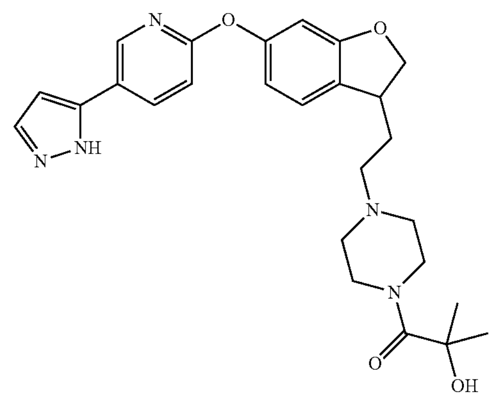 | 2-Hydroxy-2-methyl-1-[4-(2-{6-[5-(2H-pyrazol-3-yl)-pyridin-2-yloxy]-2,3-dihydro-benzofuran-3-yl}-ethyl)-piperazin-1-yl]-propan-1-one |
| 82 | 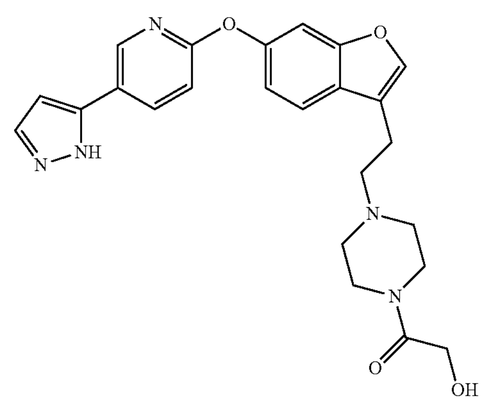 [SMILES: O=C(CO)N1CCN(CCc2coc3cc(Oc4ccc(-c5ccn[nH]5)cn4)ccc23)CC1] | 2-Hydroxy-1-[4-(2-{6-[5-(2H-pyrazol-3-yl)-pyridin-2-yloxy]-benzofuran-3-yl}-ethyl)-piperazin-1-yl]-ethanone |
| 83 | 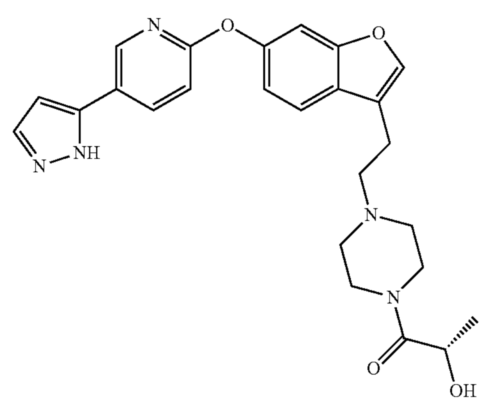 [SMILES: C[C@H](O)C(=O)N1CCN(CCc2coc3cc(Oc4ccc(-c5ccn[nH]5)cn4)ccc23)CC1] | (S)-2-Hydroxy-1-[4-(2-{6-[5-(2H-pyrazol-3-yl)-pyridin-2-yloxy]-benzofuran-3-yl}-ethyl)-piperazin-1-yl]-propan-1-one |

TABLE 1-continued

Compounds of the invention.

| Ex. | Structure | Compound Name |
|---|---|---|
| 84 | 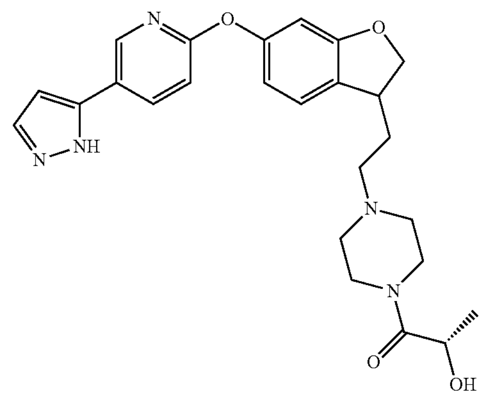 [SMILES: C[C@H](O)C(=O)N1CCN(CCC2COc3cc(Oc4ccc(-c5ccn[nH]5)cn4)ccc32)CC1] | (S)-2-Hydroxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one |
| 85 | 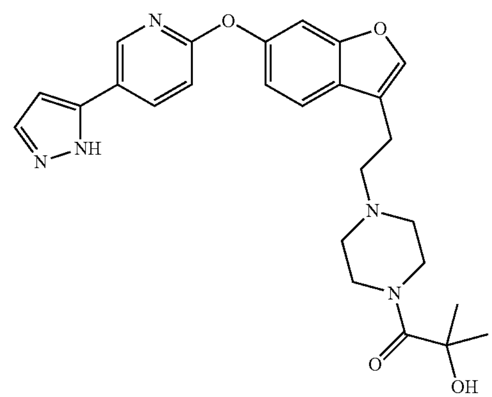 [SMILES: CC(C)(O)C(=O)N1CCN(CCc2coc3cc(Oc4ccc(-c5ccn[nH]5)cn4)ccc23)CC1] | 2-Hydroxy-2-methyl-1-[4-(2-{6-[5-(2H-pyrazol-3-yl)-pyridin-2-yloxy]-benzofuran-3-yl}-ethyl)-piperazin-1-yl]-propan-1-one |
| 86 | 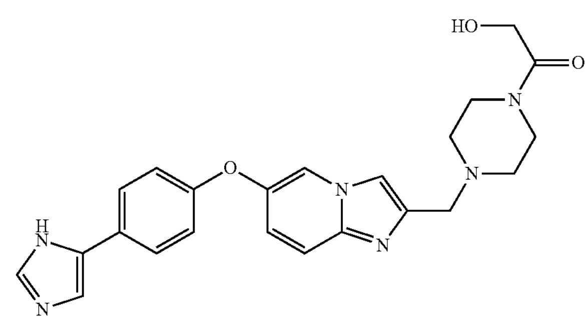 [SMILES: O=C(CO)N1CCN(Cc2cn3cc(Oc4ccc(-c5cnc[nH]5)cc4)ccc3n2)CC1] | 2-Hydroxy-1-(4-{6-[4-(2H-pyrazol-3-yl)-phenoxy]-imidazo[1,2-a]pyridin-2-ylmethyl}-piperazin-1-yl)-ethanone |
| 87 | 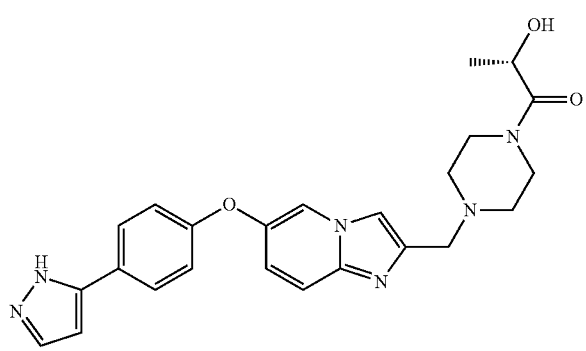 [SMILES: C[C@H](O)C(=O)N1CCN(Cc2cn3cc(Oc4ccc(-c5ccn[nH]5)cc4)ccc3n2)CC1] | (S)-2-Hydroxy-1-(4-{6-[4-(2H-pyrazol-3-yl)-phenoxy]-imidazo[1,2-a]pyridin-2-ylmethyl}-piperazin-1-yl)-propan-1-one |

TABLE 1-continued

Compounds of the invention.

| Ex. | Structure | Compound Name |
|---|---|---|
| 88 | 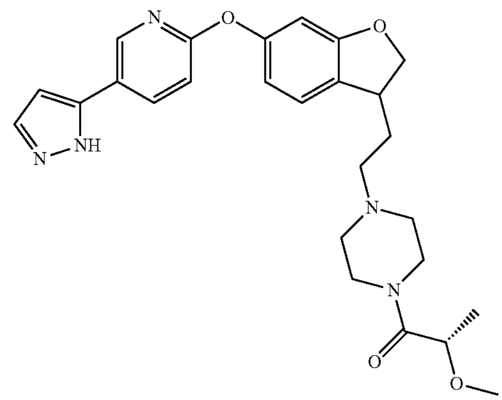 [SMILES: CO[C@@H](C)C(=O)N1CCN(CCC2COc3cc(Oc4ccc(-c5ccn[nH]5)cn4)ccc32)CC1] | (S)-2-Methoxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one |
| 89 | 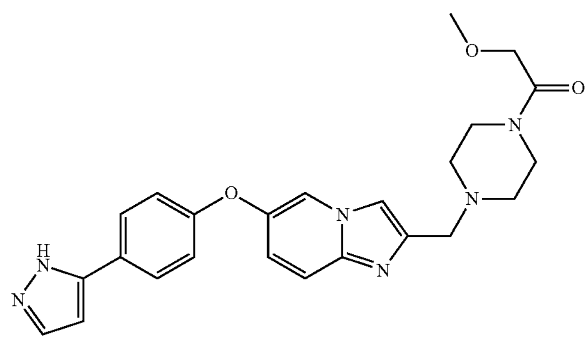 [SMILES: COCC(=O)N1CCN(Cc2cn3cc(Oc4ccc(-c5ccn[nH]5)cc4)ccc3n2)CC1] | 2-Methoxy-1-(4-{6-[4-(2H-pyrazol-3-yl)-phenoxy]-imidazo[1,2-a]pyridin-2-ylmethyl}-piperazin-1-yl)-ethanone |
| 90 | 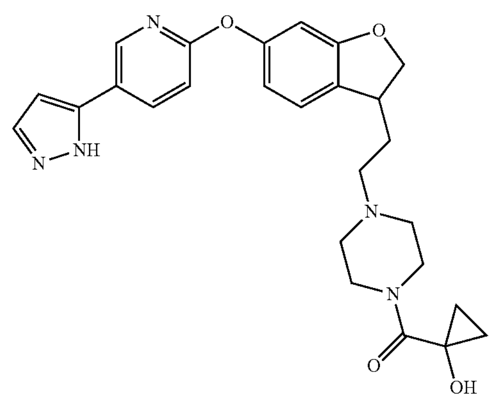 [SMILES: O=C(N1CCN(CCC2COc3cc(Oc4ccc(-c5ccn[nH]5)cn4)ccc32)CC1)C1(O)CC1] | (1-Hydroxy-cyclopropyl)-[4-(2-{6-[5-(2H-pyrazol-3-yl)-pyridin-2-yloxy]-2,3-dihydro-benzofuran-3-yl}-ethyl)-piperazin-1-yl]-methanone |
| 91 | 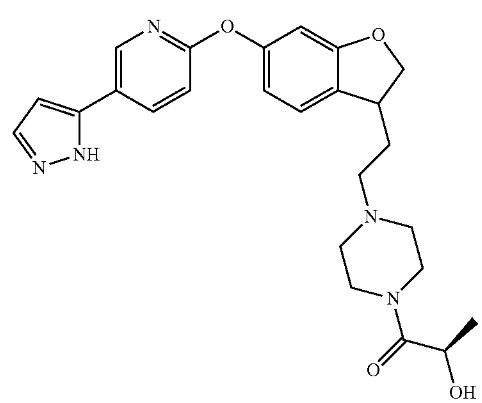 [SMILES: C[C@@H](O)C(=O)N1CCN(CCC2COc3cc(Oc4ccc(-c5ccn[nH]5)cn4)ccc32)CC1] | (R)-2-Hydroxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one |

TABLE 1-continued

Compounds of the invention.

| Ex. | Structure | Compound Name |
| --- | --- | --- |
| 92 | 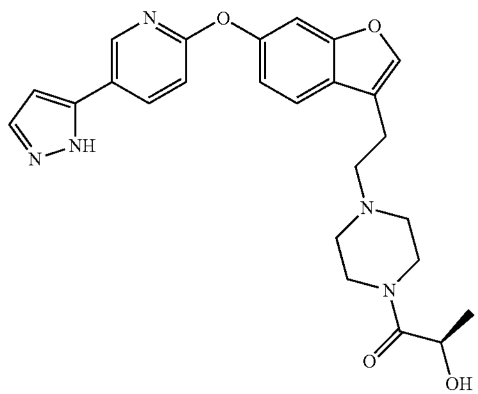 | (R)-2-Hydroxy-1-[4-(2-{6-[5-(2H-pyrazol-3-yl)-pyridin-2-yloxy]-benzofuran-3-yl}-ethyl)-piperazin-1-yl]-propan-1-one |
| 93 | 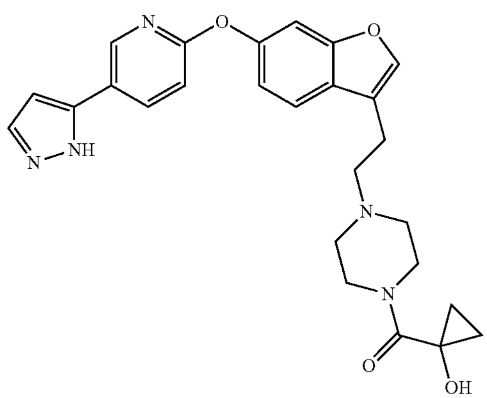 [SMILES: O=C(N1CCN(CCc2coc3cc(Oc4ccc(-c5ccn[nH]5)cn4)ccc23)CC1)C1(O)CC1] | (1-Hydroxy-cyclopropyl)-[4-(2-{6-[5-(2H-pyrazol-3-yl)-pyridin-2-yloxy]-benzofuran-3-yl}-ethyl)-piperazin-1-yl]-methanone |
| 94 | 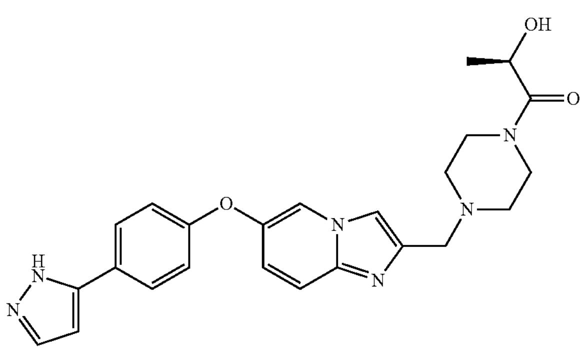 [SMILES: C[C@@H](O)C(=O)N1CCN(Cc2cn3cc(Oc4ccc(-c5ccn[nH]5)cc4)ccc3n2)CC1] | (R)-2-Hydroxy-1-(4-{6-[4-(2H-pyrazol-3-yl)-phenoxy]-imidazo[1,2-a]pyridin-2-ylmethyl}-piperazin-1-yl)-propan-1-one |
| 95 | 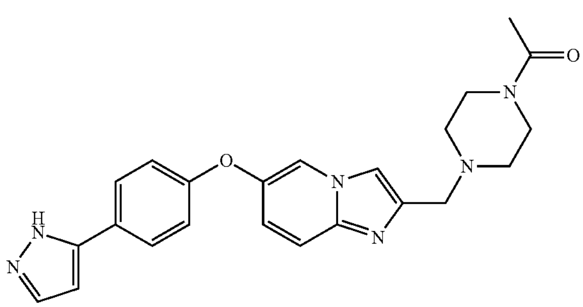 [SMILES: CC(=O)N1CCN(Cc2cn3cc(Oc4ccc(-c5ccn[nH]5)cc4)ccc3n2)CC1] | 1-(4-{6-[4-(2H-Pyrazol-3-yl)-phenoxy]-imidazo[1,2-a]pyridin-2-ylmethyl}-piperazin-1-yl)-ethanone |

TABLE 1-continued

Compounds of the invention.

| Ex. | Structure | Compound Name |
|---|---|---|
| 96 | 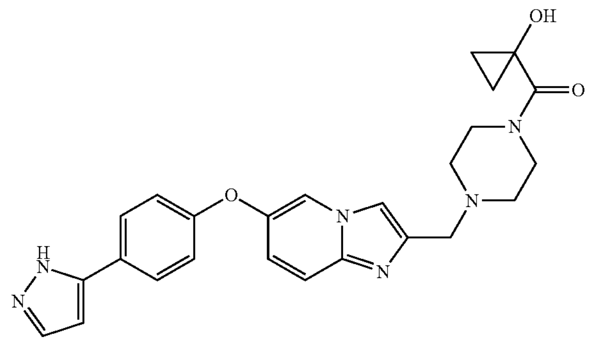 [SMILES: O=C(N1CCN(Cc2cn3cc(Oc4ccc(-c5ccn[nH]5)cc4)ccc3n2)CC1)C1(O)CC1] | (1-Hydroxy-cyclopropyl)-(4-{6-[4-(2H-pyrazol-3-yl)-phenoxy]-imidazo[1,2-a]pyridin-2-ylmethyl}-piperazin-1-yl)-methanone |
| 97 | 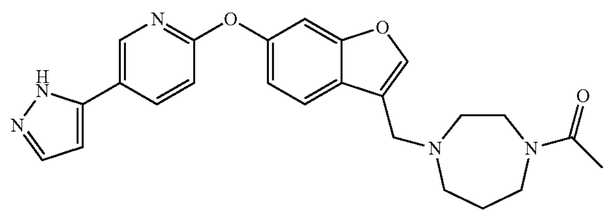 [SMILES: CC(=O)N1CCCN(Cc2coc3cc(Oc4ccc(-c5ccn[nH]5)cn4)ccc23)CC1] | 1-(4-{6-[5-(2H-Pyrazol-3-yl)-pyridin-2-yloxy]-benzofuran-3-ylmethyl}-[1,4]diazepan-1-yl)-ethanone |
| 98 | 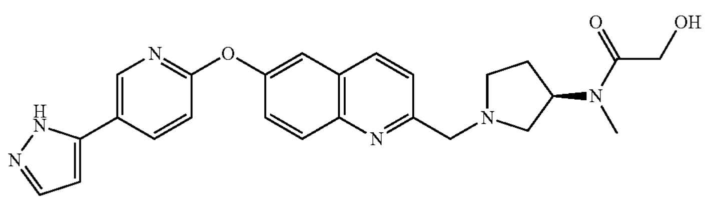 [SMILES: CN(C(=O)CO)[C@@H]1CCN(Cc2ccc3cc(Oc4ccc(-c5ccn[nH]5)cn4)ccc3n2)C1] | 2-Hydroxy-N-methyl-N-((R)-1-{6-[5-(2H-pyrazol-3-yl)-pyridin-2-yloxy]-quinolin-2-ylmethyl}-pyrrolidin-3-yl)-acetamide |
| 99 | 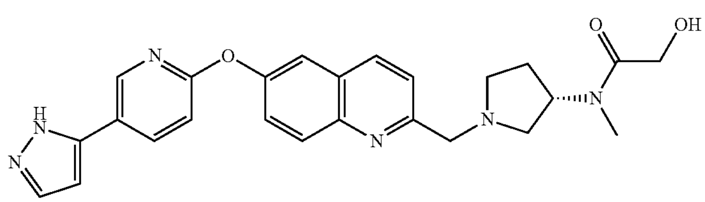 [SMILES: CN(C(=O)CO)[C@H]1CCN(Cc2ccc3cc(Oc4ccc(-c5ccn[nH]5)cn4)ccc3n2)C1] | 2-Hydroxy-N-methyl-N-((S)-1-{6-[5-(2H-pyrazol-3-yl)-pyridin-2-yloxy]-quinolin-2-ylmethyl}-pyrrolidin-3-yl)-acetamide |
| 100 | 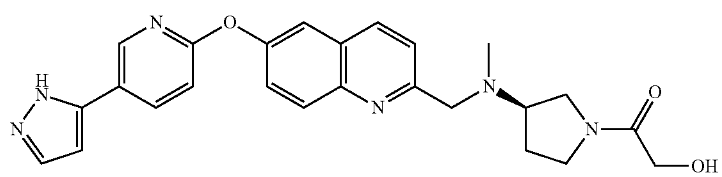 [SMILES: CN(Cc1ccc2cc(Oc3ccc(-c4ccn[nH]4)cn3)ccc2n1)[C@@H]1CCN(C(=O)CO)C1] | 2-Hydroxy-1-[(R)-3-(methyl-{6-[5-(2H-pyrazol-3-yl)-pyridin-2-yloxy]-quinolin-2-ylmethyl}-amino)-pyrrolidin-1-yl]-ethanone |
| 101 | 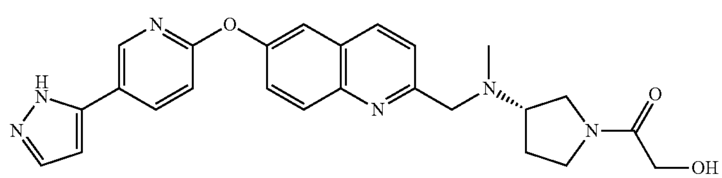 [SMILES: CN(Cc1ccc2cc(Oc3ccc(-c4ccn[nH]4)cn3)ccc2n1)[C@H]1CCN(C(=O)CO)C1] | 2-Hydroxy-1-[(S)-3-(methyl-{6-[5-(2H-pyrazol-3-yl)-pyridin-2-yloxy]-quinolin-2-ylmethyl}-amino)-pyrrolidin-1-yl]-ethanone |
| 102 | 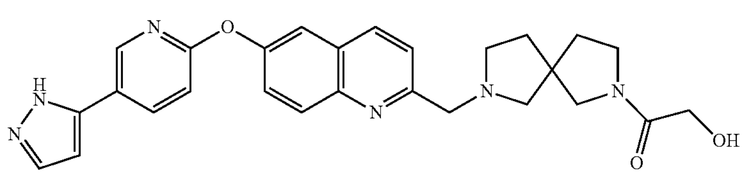 [SMILES: O=C(CO)N1CCC2(CCN(Cc3ccc4cc(Oc5ccc(-c6ccn[nH]6)cn5)ccc4n3)C2)C1] | 2-Hydroxy-1-(7-{6-[5-(2H-pyrazol-3-yl)-pyridin-2-yloxy]-quinolin-2-ylmethyl}-2,7-diaza-spiro[4.4]non-2-yl)-ethanone |

TABLE 1-continued

Compounds of the invention.

| Ex. | Structure | Compound Name |
| --- | --- | --- |
| 103 | 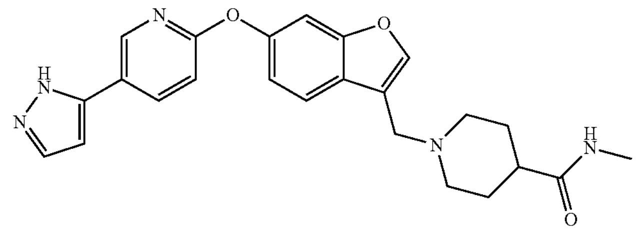 [SMILES: CNC(=O)C1CCN(Cc2coc3cc(Oc4ccc(-c5ccn[nH]5)cn4)ccc23)CC1] | 1-{6-[5-(2H-Pyrazol-3-yl)-pyridin-2-yloxy]-benzofuran-3-ylmethyl}-piperidine-4-carboxylic acid methylamide |
| 104 | 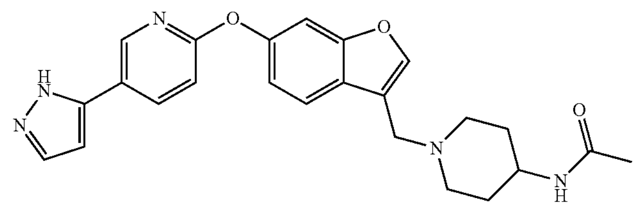 [SMILES: CC(=O)NC1CCN(Cc2coc3cc(Oc4ccc(-c5ccn[nH]5)cn4)ccc23)CC1] | N-(1-{6-[5-(2H-Pyrazol-3-yl)-pyridin-2-yloxy]-benzofuran-3-ylmethyl}-piperidin-4-yl)-acetamide |
| 105 | 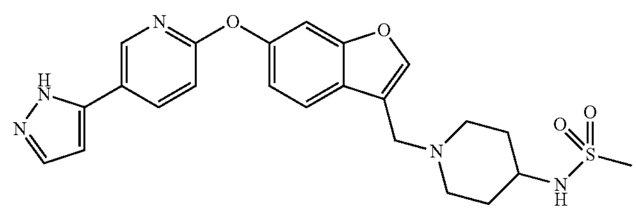 [SMILES: CS(=O)(=O)NC1CCN(Cc2coc3cc(Oc4ccc(-c5ccn[nH]5)cn4)ccc23)CC1] | N-(1-{6-[5-(2H-Pyrazol-3-yl)-pyridin-2-yloxy]-benzofuran-3-ylmethyl}-piperidin-4-yl)-methanesulfonamide |
| 106 | 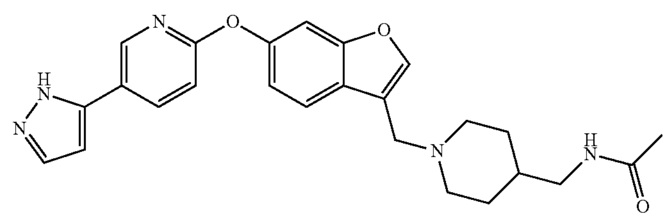 [SMILES: CC(=O)NCC1CCN(Cc2coc3cc(Oc4ccc(-c5ccn[nH]5)cn4)ccc23)CC1] | N-(1-{6-[5-(2H-Pyrazol-3-yl)-pyridin-2-yloxy]-benzofuran-3-ylmethyl}-piperidin-4-ylmethyl)-acetamide |
| 107 | 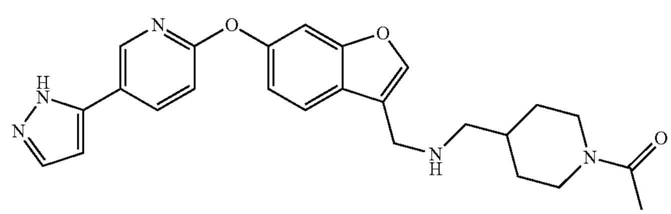 [SMILES: CC(=O)N1CCC(CNCc2coc3cc(Oc4ccc(-c5ccn[nH]5)cn4)ccc23)CC1] | 1-{4-[({6-[5-(2H-Pyrazol-3-yl)-pyridin-2-yloxy]-benzofuran-3-ylmethyl}-amino)-methyl]-piperidin-1-yl}-ethanone |
| 108 | 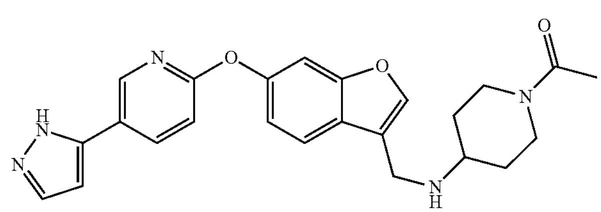 [SMILES: CC(=O)N1CCC(NCc2coc3cc(Oc4ccc(-c5ccn[nH]5)cn4)ccc23)CC1] | 1-[4-({6-[5-(2H-Pyrazol-3-yl)-pyridin-2-yloxy]-benzofuran-3-ylmethyl}-amino)-piperidin-1-yl]-ethanone |
| 109 | 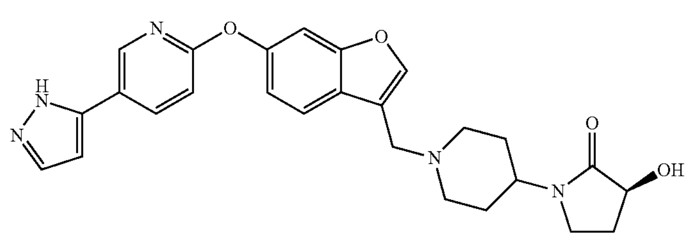 [SMILES: O=C1[C@@H](O)CCN1C1CCN(Cc2coc3cc(Oc4ccc(-c5ccn[nH]5)cn4)ccc23)CC1] | (S)-3-Hydroxy-1-(1-{6-[5-(2H-pyrazol-3-yl)-pyridin-2-yloxy]-benzofuran-3-ylmethyl}-piperidin-4-yl)-pyrrolidin-2-one |

TABLE 1-continued

Compounds of the invention.

| Ex. | Structure | Compound Name |
|---|---|---|
| 110 | 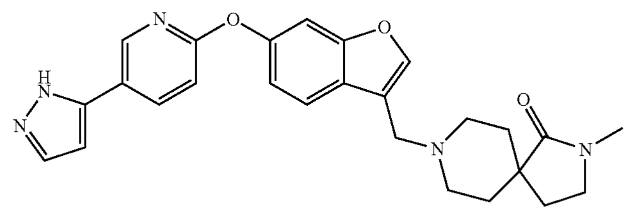 [SMILES: CN1CCC2(CCN(Cc3coc4cc(Oc5ccc(-c6ccn[nH]6)cn5)ccc34)CC2)C1=O] | 2-Methyl-8-{6-[5-(2H-pyrazol-3-yl)-pyridin-2-yloxy]-benzofuran-3-ylmethyl}-2,8-diaza-spiro[4.5]decan-1-one |
| 111 | 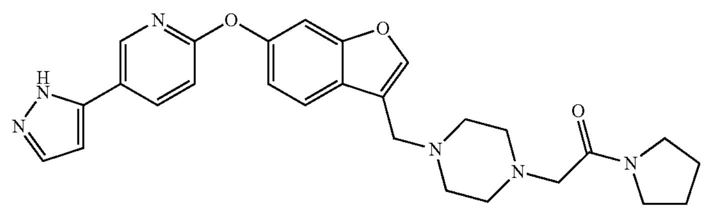 [SMILES: O=C(CN1CCN(Cc2coc3cc(Oc4ccc(-c5ccn[nH]5)cn4)ccc23)CC1)N1CCCC1] | 2-(4-{6-[5-(2H-Pyrazol-3-yl)-pyridin-2-yloxy]-benzofuran-3-ylmethyl}-piperazin-1-yl)-1-pyrrolidin-1-yl-ethanone |
| 112 | 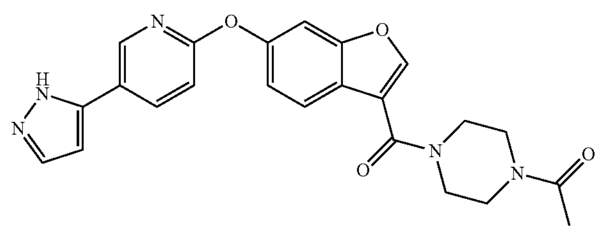 [SMILES: CC(=O)N1CCN(C(=O)c2coc3cc(Oc4ccc(-c5ccn[nH]5)cn4)ccc23)CC1] | 1-(4-{6-[5-(2H-Pyrazol-3-yl)-pyridin-2-yloxy]-benzofuran-3-carbonyl}-piperazin-1-yl)-ethanone |
| 113 | 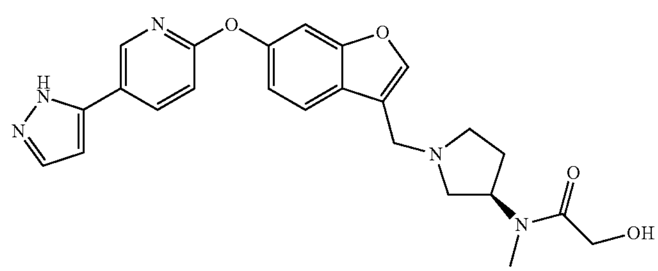 [SMILES: CN(C(=O)CO)[C@@H]1CCN(Cc2coc3cc(Oc4ccc(-c5ccn[nH]5)cn4)ccc23)C1] | 2-Hydroxy-N-methyl-N-((R)-1-{6-[5-(2H-pyrazol-3-yl)-pyridin-2-yloxy]-benzofuran-3-ylmethyl}-pyrrolidin-3-yl)-acetamide |
| 114 | 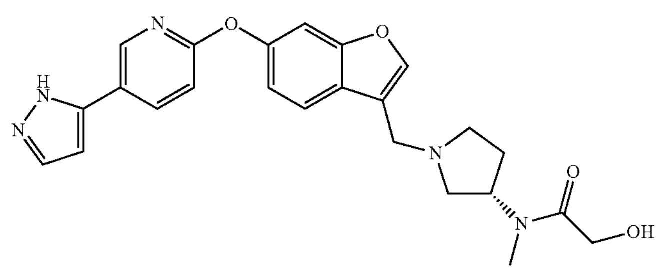 [SMILES: CN(C(=O)CO)[C@H]1CCN(Cc2coc3cc(Oc4ccc(-c5ccn[nH]5)cn4)ccc23)C1] | 2-Hydroxy-N-methyl-N-((S)-1-{6-[5-(2H-pyrazol-3-yl)-pyridin-2-yloxy]-benzofuran-3-ylmethyl}-pyrrolidin-3-yl)-acetamide |
| 115 | 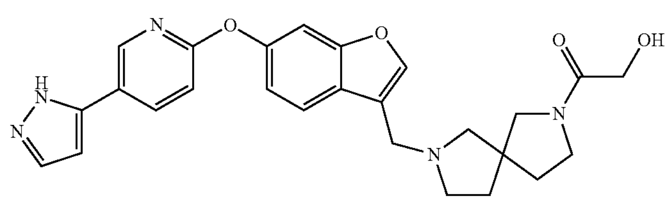 [SMILES: O=C(CO)N1CCC2(CCN(Cc3coc4cc(Oc5ccc(-c6ccn[nH]6)cn5)ccc34)C2)C1] | 2-Hydroxy-1-(7-{6-[5-(2H-pyrazol-3-yl)-pyridin-2-yloxy]-benzofuran-3-ylmethyl}-2,7-diaza-spiro[4.4]non-2-yl)-ethanone |

TABLE 1-continued

Compounds of the invention.

| Ex. | Structure | Compound Name |
|---|---|---|
| 116 | 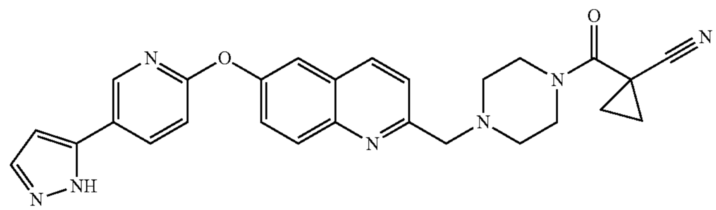 [SMILES: N#CC1(C(=O)N2CCN(Cc3ccc4cc(Oc5ccc(-c6ccn[nH]6)cn5)ccc4n3)CC2)CC1] | 1-(4-{6-[5-(2H-Pyrazol-3-yl)-pyridin-2-yloxy]-quinolin-2-ylmethyl}-piperazine-1-carbonyl)-cyclopropanecarbonitrile |
| 117 | 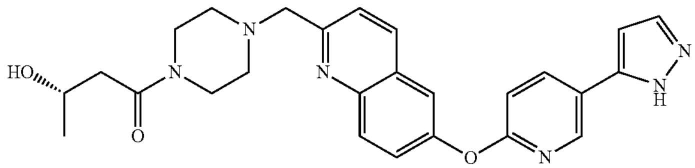 [SMILES: C[C@H](O)CC(=O)N1CCN(Cc2ccc3cc(Oc4ccc(-c5ccn[nH]5)cn4)ccc3n2)CC1] | (S)-3-Hydroxy-1-(4-{6-[5-(2H-pyrazol-3-yl)-pyridin-2-yloxy]-quinolin-2-ylmethyl}-piperazin-1-yl)-butan-1-one |
| 118 | 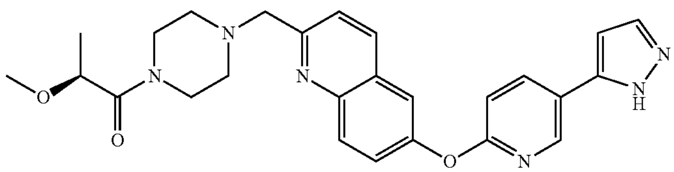 [SMILES: CO[C@@H](C)C(=O)N1CCN(Cc2ccc3cc(Oc4ccc(-c5ccn[nH]5)cn4)ccc3n2)CC1] | (S)-2-Methoxy-1-(4-{6-[5-(2H-pyrazol-3-yl)-pyridin-2-yloxy]-quinolin-2-ylmethyl}-piperazin-1-yl)-propan-1-one |
| 119 | 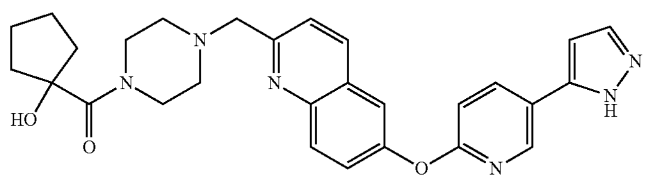 [SMILES: O=C(N1CCN(Cc2ccc3cc(Oc4ccc(-c5ccn[nH]5)cn4)ccc3n2)CC1)C1(O)CCCC1] | (1-Hydroxy-cyclopentyl)-(4-{6-[5-(2H-pyrazol-3-yl)-pyridin-2-yloxy]-quinolin-2-ylmethyl}-piperazin-1-yl)-methanone |
| 120 | 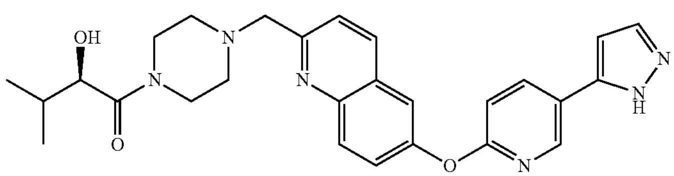 [SMILES: CC(C)[C@@H](O)C(=O)N1CCN(Cc2ccc3cc(Oc4ccc(-c5ccn[nH]5)cn4)ccc3n2)CC1] | (R)-2-Hydroxy-3-methyl-1-(4-{6-[5-(2H-pyrazol-3-yl)-pyridin-2-yloxy]-quinolin-2-ylmethyl}-piperazin-1-yl)-butan-1-one |
| 121 | 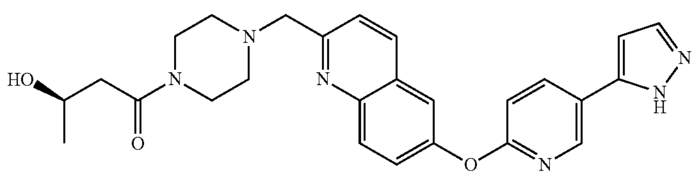 [SMILES: C[C@@H](O)CC(=O)N1CCN(Cc2ccc3cc(Oc4ccc(-c5ccn[nH]5)cn4)ccc3n2)CC1] | (R)-3-Hydroxy-1-(4-{6-[5-(2H-pyrazol-3-yl)-pyridin-2-yloxy]-quinolin-2-ylmethyl}-piperazin-1-yl)-butan-1-one |
| 122 | 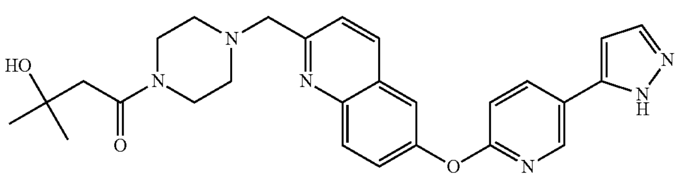 [SMILES: CC(C)(O)CC(=O)N1CCN(Cc2ccc3cc(Oc4ccc(-c5ccn[nH]5)cn4)ccc3n2)CC1] | 3-Hydroxy-3-methyl-1-(4-{6-[5-(2H-pyrazol-3-yl)-pyridin-2-yloxy]-quinolin-2-ylmethyl}-piperazin-1-yl)-butan-1-one |
| 123 | 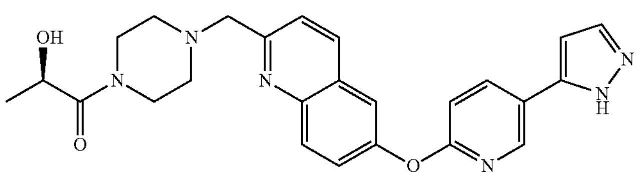 | (R)-2-Hydroxy-1-(4-{6-[5-(2H-pyrazol-3-yl)-pyridin-2-yloxy]-quinolin-2-ylmethyl}-piperazin-1-yl)-propan-1-one |

TABLE 1-continued

Compounds of the invention.

| Ex. | Structure | Compound Name |
|---|---|---|
| 124 | 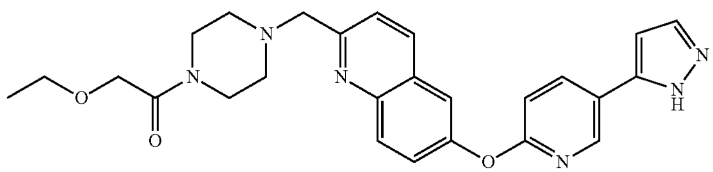 [SMILES: CCOCC(=O)N1CCN(Cc2ccc3cc(Oc4ccc(-c5ccn[nH]5)cn4)ccc3n2)CC1] | 2-Ethoxy-1-(4-{6-[5-(2H-pyrazol-3-yl)-pyridin-2-yloxy]-quinolin-2-ylmethyl}-piperazin-1-yl)-ethanone |
| 125 | 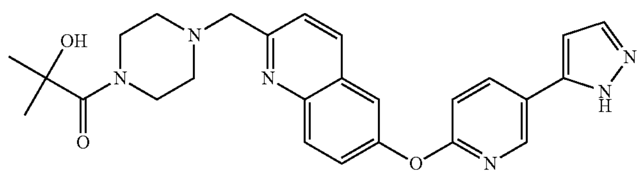 [SMILES: CC(C)(O)C(=O)N1CCN(Cc2ccc3cc(Oc4ccc(-c5ccn[nH]5)cn4)ccc3n2)CC1] | 2-Hydroxy-2-methyl-1-(4-{6-[5-(2H-pyrazol-3-yl)-pyridin-2-yloxy]-quinolin-2-ylmethyl}-piperazin-1-yl)-propan-1-one |
| 126 | 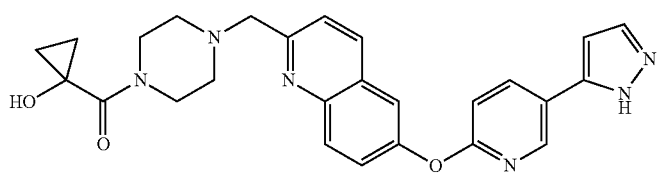 [SMILES: O=C(N1CCN(Cc2ccc3cc(Oc4ccc(-c5ccn[nH]5)cn4)ccc3n2)CC1)C1(O)CC1] | (1-Hydroxy-cyclopropyl)-(4-{6-[5-(2H-pyrazol-3-yl)-pyridin-2-yloxy]-quinolin-2-ylmethyl}-piperazin-1-yl)-methanone |
| 127 | 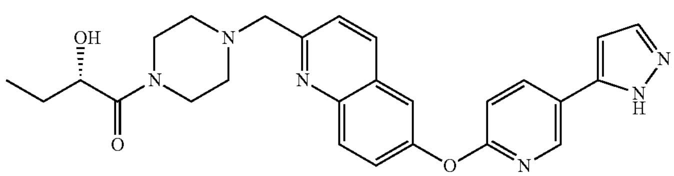 [SMILES: CC[C@H](O)C(=O)N1CCN(Cc2ccc3cc(Oc4ccc(-c5ccn[nH]5)cn4)ccc3n2)CC1] | (S)-2-Hydroxy-1-(4-{6-[5-(2H-pyrazol-3-yl)-pyridin-2-yloxy]-quinolin-2-ylmethyl}-piperazin-1-yl)-butan-1-one |
| 128 | 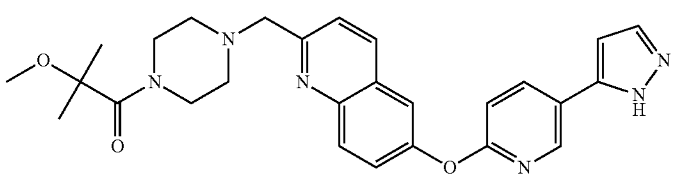 [SMILES: COC(C)(C)C(=O)N1CCN(Cc2ccc3cc(Oc4ccc(-c5ccn[nH]5)cn4)ccc3n2)CC1] | 2-Methoxy-2-methyl-1-(4-{6-[5-(2H-pyrazol-3-yl)-pyridin-2-yloxy]-quinolin-2-ylmethyl}-piperazin-1-yl)-propan-1-one |
| 129 | 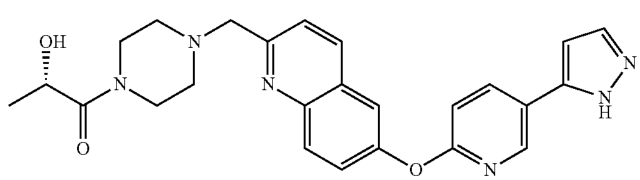 [SMILES: C[C@H](O)C(=O)N1CCN(Cc2ccc3cc(Oc4ccc(-c5ccn[nH]5)cn4)ccc3n2)CC1] | (S)-2-Hydroxy-1-(4-{6-[5-(2H-pyrazol-3-yl)-pyridin-2-yloxy]-quinolin-2-ylmethyl}-piperazin-1-yl)-propan-1-one |
| 130 | 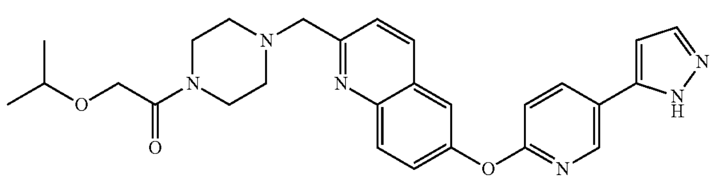 [SMILES: CC(C)OCC(=O)N1CCN(Cc2ccc3cc(Oc4ccc(-c5ccn[nH]5)cn4)ccc3n2)CC1] | 2-Isopropoxy-1-(4-{6-[5-(2H-pyrazol-3-yl)-pyridin-2-yloxy]-quinolin-2-ylmethyl}-piperazin-1-yl)-ethanone |
| 131 | 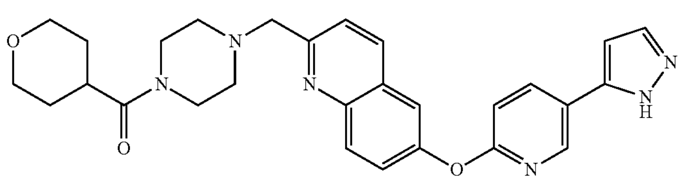 [SMILES: O=C(C1CCOCC1)N1CCN(Cc2ccc3cc(Oc4ccc(-c5ccn[nH]5)cn4)ccc3n2)CC1] | (4-{6-[5-(2H-Pyrazol-3-yl)-pyridin-2-yloxy]-quinolin-2-ylmethyl}-piperazin-1-yl)-(tetrahydro-pyran-4-yl)-methanone |

TABLE 1-continued

Compounds of the invention.

| Ex. | Structure | Compound Name |
| --- | --- | --- |
| 132 | 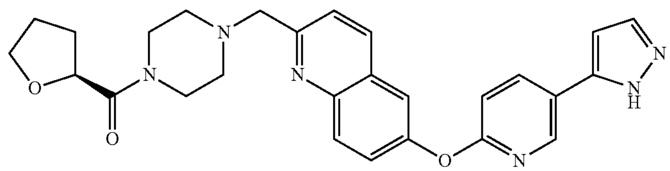 [SMILES: O=C([C@@H]1CCCO1)N1CCN(Cc2ccc3cc(Oc4ccc(-c5ccn[nH]5)cn4)ccc3n2)CC1] | (4-{6-[5-(2H-Pyrazol-3-yl)-pyridin-2-yloxy]-quinolin-2-ylmethyl}-piperazin-1-yl)-(S)-tetrahydro-furan-2-yl-methanone |
| 133 | 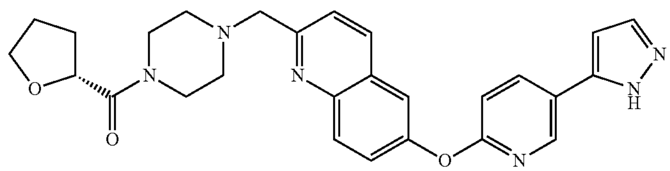 [SMILES: O=C([C@H]1CCCO1)N1CCN(Cc2ccc3cc(Oc4ccc(-c5ccn[nH]5)cn4)ccc3n2)CC1] | (4-{6-[5-(2H-Pyrazol-3-yl)-pyridin-2-yloxy]-quinolin-2-ylmethyl}-piperazin-1-yl)-(R)-tetrahydro-furan-2-yl-methanone |
| 134 | 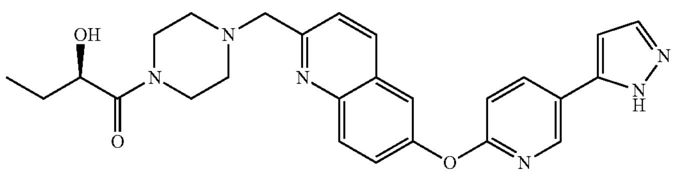 [SMILES: CC[C@@H](O)C(=O)N1CCN(Cc2ccc3cc(Oc4ccc(-c5ccn[nH]5)cn4)ccc3n2)CC1] | (R)-2-Hydroxy-1-(4-{6-[5-(2H-pyrazol-3-yl)-pyridin-2-yloxy]-quinolin-2-ylmethyl}-piperazin-1-yl)-butan-1-one |
| 135 | 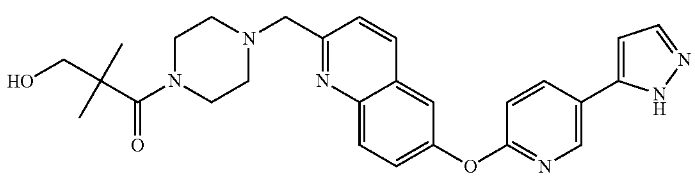 [SMILES: CC(C)(CO)C(=O)N1CCN(Cc2ccc3cc(Oc4ccc(-c5ccn[nH]5)cn4)ccc3n2)CC1] | 3-Hydroxy-2,2-dimethyl-1-(4-{6-[5-(2H-pyrazol-3-yl)-pyridin-2-yloxy]-quinolin-2-ylmethyl}-piperazin-1-yl)-propan-1-one |
| 136 | 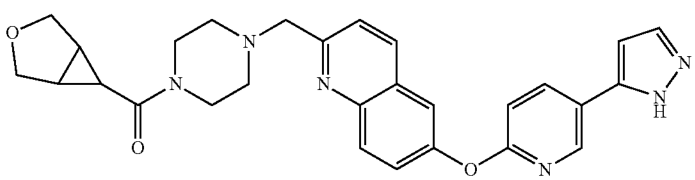 [SMILES: O=C(C1C2COCC21)N1CCN(Cc2ccc3cc(Oc4ccc(-c5ccn[nH]5)cn4)ccc3n2)CC1] | (3-Oxa-bicyclo[3.1.0]hex-6-yl)-(4-{6-[5-(2H-pyrazol-3-yl)-pyridin-2-yloxy]-quinolin-2-ylmethyl}-piperazin-1-yl)-methanone |
| 137 | 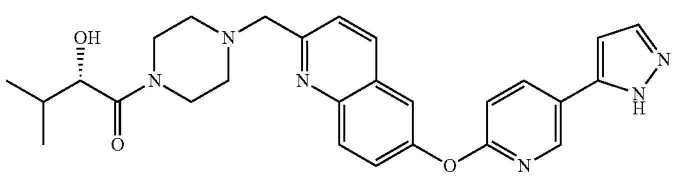 [SMILES: CC(C)[C@H](O)C(=O)N1CCN(Cc2ccc3cc(Oc4ccc(-c5ccn[nH]5)cn4)ccc3n2)CC1] | (S)-2-Hydroxy-3-methyl-1-(4-{6-[5-(2H-pyrazol-3-yl)-pyridin-2-yloxy]-quinolin-2-ylmethyl}-piperazin-1-yl)-butan-1-one |
| 138 | 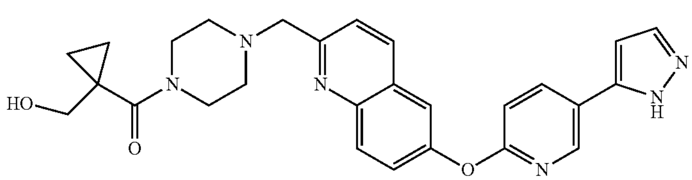 [SMILES: O=C(N1CCN(Cc2ccc3cc(Oc4ccc(-c5ccn[nH]5)cn4)ccc3n2)CC1)C1(CO)CC1] | (1-Hydroxymethyl-cyclopropyl)-(4-{6-[5-(2H-pyrazol-3-yl)-pyridin-2-yloxy]-quinolin-2-ylmethyl}-piperazin-1-yl)-methanone |
| 139 | 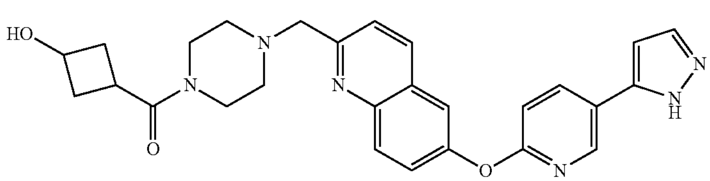 [SMILES: O=C(C1CC(O)C1)N1CCN(Cc2ccc3cc(Oc4ccc(-c5ccn[nH]5)cn4)ccc3n2)CC1] | (3-Hydroxy-cyclobutyl)-(4-{6-[5-(2H-pyrazol-3-yl)-pyridin-2-yloxy]-quinolin-2-ylmethyl}-piperazin-1-yl)-methanone |

TABLE 1-continued

Compounds of the invention.

| Ex. | Structure | Compound Name |
|---|---|---|
| 140 | 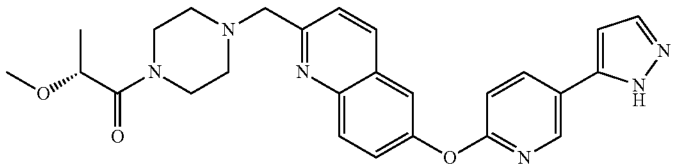 [SMILES: CO[C@H](C)C(=O)N1CCN(Cc2ccc3cc(Oc4ccc(-c5ccn[nH]5)cn4)ccc3n2)CC1] | (R)-2-Methoxy-1-(4-{6-[5-(2H-pyrazol-3-yl)-pyridin-2-yloxy]-quinolin-2-ylmethyl}-piperazin-1-yl)-propan-1-one |
| 141 | 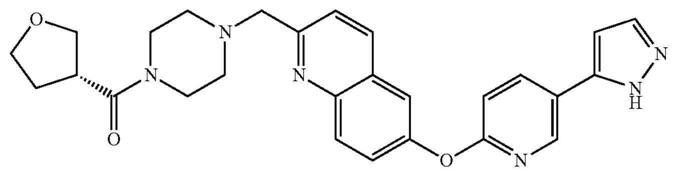 [SMILES: O=C([C@@H]1CCOC1)N1CCN(Cc2ccc3cc(Oc4ccc(-c5ccn[nH]5)cn4)ccc3n2)CC1] | (4-{6-[5-(2H-Pyrazol-3-yl)-pyridin-2-yloxy]-quinolin-2-ylmethyl}-piperazin-1-yl)-(R)-tetrahydro-furan-3-yl-methanone |
| 142 | 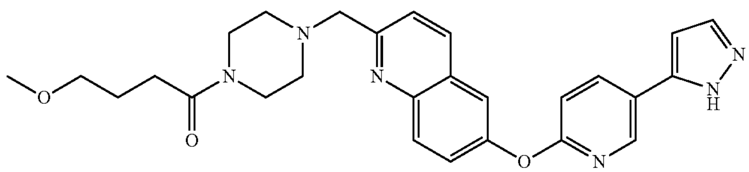 [SMILES: COCCCC(=O)N1CCN(Cc2ccc3cc(Oc4ccc(-c5ccn[nH]5)cn4)ccc3n2)CC1] | 4-Methoxy-1-(4-{6-[5-(2H-pyrazol-3-yl)-pyridin-2-yloxy]-quinolin-2-ylmethyl}-piperazin-1-yl)-butan-1-one |
| 143 | 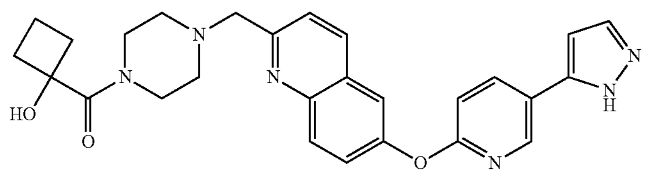 [SMILES: O=C(N1CCN(Cc2ccc3cc(Oc4ccc(-c5ccn[nH]5)cn4)ccc3n2)CC1)C1(O)CCC1] | (1-Hydroxy-cyclobutyl)-(4-{6-[5-(2H-pyrazol-3-yl)-pyridin-2-yloxy]-quinolin-2-ylmethyl}-piperazin-1-yl)-methanone |
| 144 | 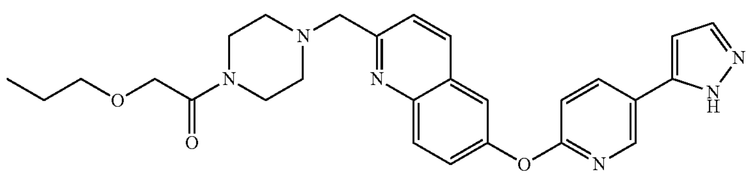 [SMILES: CCCOCC(=O)N1CCN(Cc2ccc3cc(Oc4ccc(-c5ccn[nH]5)cn4)ccc3n2)CC1] | 2-Propoxy-1-(4-{6-[5-(2H-pyrazol-3-yl)-pyridin-2-yloxy]-quinolin-2-ylmethyl}-piperazin-1-yl)-ethanone |
| 145 | 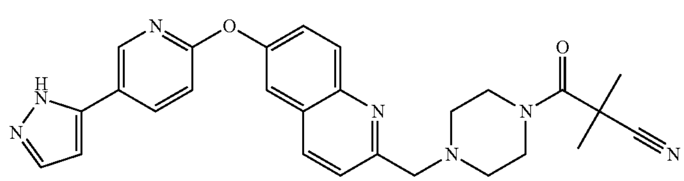 [SMILES: CC(C)(C#N)C(=O)N1CCN(Cc2ccc3cc(Oc4ccc(-c5ccn[nH]5)cn4)ccc3n2)CC1] | 2,2-Dimethyl-3-oxo-3-(4-{6-[5-(2H-pyrazol-3-yl)-pyridin-2-yloxy]-quinolin-2-ylmethyl}-piperazin-1-yl)-propionitrile |
| 146 | 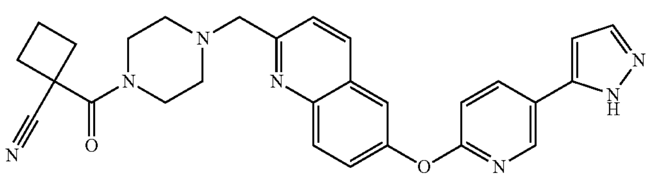 [SMILES: N#CC1(C(=O)N2CCN(Cc3ccc4cc(Oc5ccc(-c6ccn[nH]6)cn5)ccc4n3)CC2)CCC1] | 1-(4-{6-[5-(2H-Pyrazol-3-yl)-pyridin-2-yloxy]-quinolin-2-ylmethyl}-piperazine-1-carbonyl)-cyclobutanecarbonitrile |
| 147 | 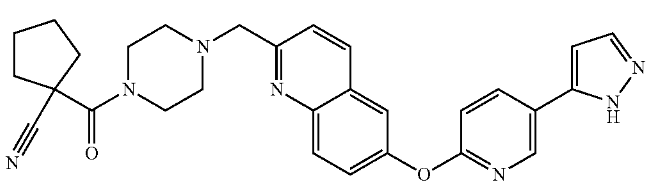 [SMILES: N#CC1(C(=O)N2CCN(Cc3ccc4cc(Oc5ccc(-c6ccn[nH]6)cn5)ccc4n3)CC2)CCCC1] | 1-(4-{6-[5-(2H-Pyrazol-3-yl)-pyridin-2-yloxy]-quinolin-2-ylmethyl}-piperazine-1-carbonyl)-cyclopentanecarbonitrile |

TABLE 1-continued

Compounds of the invention.

| Ex. | Structure | Compound Name |
|---|---|---|
| 148 | 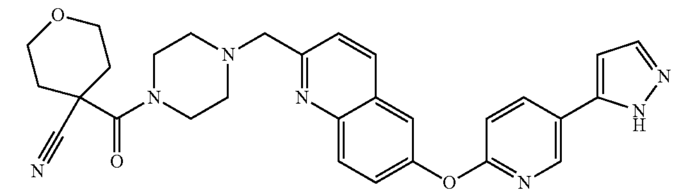 [SMILES: N#CC1(C(=O)N2CCN(Cc3ccc4cc(Oc5ccc(-c6ccn[nH]6)cn5)ccc4n3)CC2)CCOCC1] | 4-(4-{6-[5-(2H-Pyrazol-3-yl)-pyridin-2-yloxy]-quinolin-2-ylmethyl}-piperazine-1-carbonyl)-tetrahydro-pyran-4-carbonitrile |
| 149 | 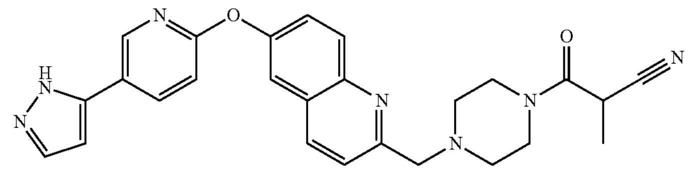 [SMILES: CC(C#N)C(=O)N1CCN(Cc2ccc3cc(Oc4ccc(-c5ccn[nH]5)cn4)ccc3n2)CC1] | 2-Methyl-3-oxo-3-(4-{6-[5-(2H-pyrazol-3-yl)-pyridin-2-yloxy]-quinolin-2-ylmethyl}-piperazin-1-yl)-propionitrile |
| 150 | 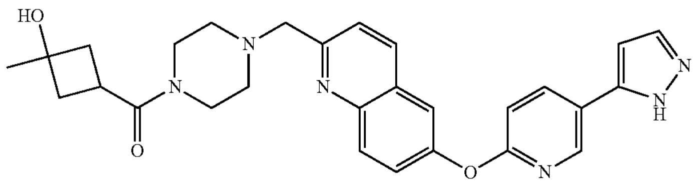 [SMILES: CC1(O)CC(C(=O)N2CCN(Cc3ccc4cc(Oc5ccc(-c6ccn[nH]6)cn5)ccc4n3)CC2)C1] | (3-Hydroxy-3-methyl-cyclobutyl)-(4-{6-[5-(2H-pyrazol-3-yl)-pyridin-2-yloxy]-quinolin-2-ylmethyl}-piperazin-1-yl)-methanone |
| 151 | 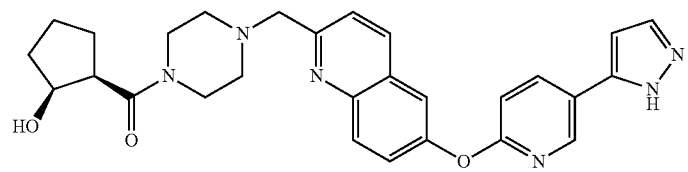 [SMILES: O=C([C@@H]1CCC[C@@H]1O)N1CCN(Cc2ccc3cc(Oc4ccc(-c5ccn[nH]5)cn4)ccc3n2)CC1] | ((1R,2S)-2-Hydroxy-cyclopentyl)-(4-{6-[5-(2H-pyrazol-3-yl)-pyridin-2-yloxy]-quinolin-2-ylmethyl}-piperazin-1-yl)-methanone |

DETAILED DESCRIPTION OF THE INVENTION

Definitions

Ac=acetyl
AcOH=acetic acid
AIBN=azobisisobutyronitrile
BOC=tert-butyloxycarbonyl
BnO=benzyloxide
DCE=1,2-dichloroethane
DCM=dichloromethane
DDQ=2,3-dichloro-5,6-dicyano-1,4-benzoquinone
DEA=diethylamine
DIBAL-H=diisobutylaluminum hydride
DIPEA=diisopropylethylamine
DMA=dimethylacetamide
DMAP=4-dimethylaminopyridine
DME=1,2-dimethoxyethane
DMF=dimethylformamide
DMS=dimethylsulfide
DMSO=dimethylsulfoxide
Et$_2$O=ethylether
EtOAc=ethyl acetate
EtOH=ethanol
HATU=2-(7-aza-1H-benzotriazole-1-yl)-1,1,3,3-tetramethyluronium hexafluorophosphate
IPA=isopropyl alcohol
LAH=lithium aluminum hydride
LDA=lithium diisopropylamide
mCPBA=meta-chloroperoxybenzoic acid
MeCN=acetonitrile
MeOH=methanol
MP-TSOH=polymer-supported toluenesulfonic acid resin
MTBE=methyl tert-butyl ether
NBS=N-bromosuccinimide
NMP=N-methylpyrrolidinone
PyBrop=bromo-tris-pyrrolidino phosphoniumhexafluorophosphate
PL-HCO$_3$=polymer-bound tetraalkylammoniumcarbonate resin
PS-DIEA=polymer-supported N,N-diisopropylethylamine resin
Rochelle salt=potassium sodium tartrate tetrahydrate
RP-HPLC=reverse phase HPLC
SEM=2-(trimethylsilyl)ethoxymethyl
TBAF=tetra-n-butylammonium fluoride
TBDPSCl=t-butyldiphenylsilyl chloride
TBTU=2-(1H-benzotriazole-1-yl)-1,1,3,3-tetramethyluronium tetrafluoroborate
TEA=triethylamine
Tf=trifluoromethanesulfonyl
TFA=trifluoroacetic acid
THF=tetrahydrofuran
TIPSO=triisopropylsiloxy As noted above, the invention relates to any one of the compounds depicted in Table 1, and pharmaceutically acceptable salts thereof.

In another embodiment, the invention relates to a compound selected from the group consisting of:
2-Methoxy-1-(4-{6-[5-(2H-pyrazol-3-yl)-pyrimidin-2-yloxy]-naphthalen-2-ylmethyl}-piperazin-1-yl)-ethanone;

1-(4-{6-[5-(2H-Pyrazol-3-yl)-pyrimidin-2-yloxy]-naphthalen-2-ylmethyl}-piperazin-1-yl)-ethanone;
1-{6-[5-(2H-Pyrazol-3-yl)-pyrimidin-2-yloxy]-naphthalen-2-ylmethyl}-piperidin-4-ol;
1-{6-[5-(2H-Pyrazol-3-yl)-pyrimidin-2-yloxy]-naphthalen-2-ylmethyl}-piperidine-4-carboxylic acid amide;
N-(1-{6-[5-(2H-Pyrazol-3-yl)-pyrimidin-2-yloxy]-naphthalen-2-ylmethyl}-piperidin-4-yl)-acetamide;
(S)-3-Hydroxy-1-(1-{6-[5-(2H-pyrazol-3-yl)-pyrimidin-2-yloxy]-naphthalen-2-ylmethyl}-piperidin-4-yl)-pyrrolidin-2-one;
(S)-2-Hydroxy-1-(4-{6-[5-(2H-pyrazol-3-yl)-pyrimidin-2-yloxy]-naphthalen-2-ylmethyl}-piperazin-1-yl)-propan-1-one;
2-Hydroxy-N-methyl-N-(1-{6-[5-(2H-pyrazol-3-yl)-pyrimidin-2-yloxy]-naphthalen-2-ylmethyl}-piperidin-4-yl)-acetamide;
1-{3-[(Methyl-{6-[5-(2H-pyrazol-3-yl)-pyrimidin-2-yloxy]-naphthalen-2-ylmethyl}-amino)-methyl]-azetidin-1-yl}-ethanone;
3-(1-{6-[5-(2H-Pyrazol-3-yl)-pyrimidin-2-yloxy]-naphthalen-2-ylmethyl}-piperidin-4-yl)-oxazolidin-2-one;
4-{6-[5-(2H-Pyrazol-3-yl)-pyrimidin-2-yloxy]-naphthalen-2-ylmethyl}-piperazine-1-carboxylic acid dimethylamide;
2,2-Dimethyl-1-(4-{6-[5-(2H-pyrazol-3-yl)-pyrimidin-2-yloxy]-naphthalen-2-ylmethyl}-piperazin-1-yl)-propan-1-one;
1-(1-{6-[5-(2H-Pyrazol-3-yl)-pyrimidin-2-yloxy]-naphthalen-2-ylmethyl}-piperidin-4-yl)-pyrrolidin-2-one;
1-(4-{6-[5-(2H-Pyrazol-3-yl)-pyrimidin-2-yloxy]-naphthalen-2-ylmethyl}-piperazin-1-yl)-propan-1-one;
1-{6-[5-(2H-Pyrazol-3-yl)-pyrimidin-2-yloxy]-naphthalen-2-ylmethyl}-piperidine-4-carboxylic acid dimethylamide;
2-Hydroxy-2-methyl-1-(4-{6-[5-(2H-pyrazol-3-yl)-pyrimidin-2-yloxy]-naphthalen-2-ylmethyl}-piperazin-1-yl)-propan-1-one;
Cyclopropyl-(4-{6-[5-(2H-pyrazol-3-yl)-pyrimidin-2-yloxy]-naphthalen-2-ylmethyl}-piperazin-1-yl)-methanone;
2-Methyl-1-(4-{6-[5-(2H-pyrazol-3-yl)-pyrimidin-2-yloxy]-naphthalen-2-ylmethyl}-piperazin-1-yl)-propan-1-one;
(R)-1-{6-[5-(2H-Pyrazol-3-yl)-pyrimidin-2-yloxy]-naphthalen-2-ylmethyl}-pyrrolidin-3-ol;
(S)-1-{6-[5-(2H-Pyrazol-3-yl)-pyrimidin-2-yloxy]-naphthalen-2-ylmethyl}-pyrrolidin-3-ol;
3-Methyl-1-{6-[5-(2H-pyrazol-3-yl)-pyrimidin-2-yloxy]-naphthalen-2-ylmethyl}-azetidin-3-ol;
2-Hydroxy-1-(4-{6-[5-(2H-pyrazol-3-yl)-pyrimidin-2-yloxy]-naphthalen-2-ylmethyl}-piperazin-1-yl)-ethanone; and
1-{6-[5-(2H-Pyrazol-3-yl)-pyrimidin-2-yloxy]-naphthalen-2-ylmethyl}-azetidin-3-ol;
and pharmaceutically acceptable salts thereof.

In another embodiment, the invention relates to a compound selected from the group consisting of:
(S)-3-Hydroxy-1-(1-{6-[5-(2H-pyrazol-3-yl)-pyridin-2-yloxy]-quinolin-2-ylmethyl}-piperidin-4-yl)-pyrrolidin-2-one;
(R)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(S)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(S)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
2-Hydroxy-2-methyl-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(R)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone;
2-Hydroxy-N-methyl-N-((R)-1-{6-[5-(2H-pyrazol-3-yl)-pyridin-2-yloxy]-quinolin-2-ylmethyl}-pyrrolidin-3-yl)-acetamide;
2-Hydroxy-N-methyl-N-((S)-1-{6-[5-(2H-pyrazol-3-yl)-pyridin-2-yloxy]-quinolin-2-ylmethyl}-pyrrolidin-3-yl)-acetamide;
2-Hydroxy-1-[(R)-3-(methyl-{6-[5-(2H-pyrazol-3-yl)-pyridin-2-yloxy]-quinolin-2-ylmethyl}-amino)-pyrrolidin-1-yl]-ethanone;
2-Hydroxy-1-[(S)-3-(methyl-{6-[5-(2H-pyrazol-3-yl)-pyridin-2-yloxy]-quinolin-2-ylmethyl}-amino)-pyrrolidin-1-yl]-ethanone;
2-Hydroxy-1-(7-{6-[5-(2H-pyrazol-3-yl)-pyridin-2-yloxy]-quinolin-2-ylmethyl}-2,7-diaza-spiro[4.4]non-2-yl)-ethanone;
(S)-2-Methoxy-1-(4-{6-[5-(2H-pyrazol-3-yl)-pyridin-2-yloxy]-quinolin-2-ylmethyl}-piperazin-1-yl)-propan-1-one;
(R)-2-Hydroxy-1-(4-{6-[5-(2H-pyrazol-3-yl)-pyridin-2-yloxy]-quinolin-2-ylmethyl}-piperazin-1-yl)-propan-1-one;
(1-Hydroxy-cyclopropyl)-(4-{6-[5-(2H-pyrazol-3-yl)-pyridin-2-yloxy]-quinolin-2-ylmethyl}-piperazin-1-yl)-methanone;
2-Methoxy-2-methyl-1-(4-{6-[5-(2H-pyrazol-3-yl)-pyridin-2-yloxy]-quinolin-2-ylmethyl}-piperazin-1-yl)-propan-1-one;
(S)-2-Hydroxy-1-(4-{6-[5-(2H-pyrazol-3-yl)-pyridin-2-yloxy]-quinolin-2-ylmethyl}-piperazin-1-yl)-propan-1-one;
(R)-2-Methoxy-1-(4-{6-[5-(2H-pyrazol-3-yl)-pyridin-2-yloxy]-quinolin-2-ylmethyl}-piperazin-1-yl)-propan-1-one; and
2-Methyl-3-oxo-3-(4-{6-[5-(2H-pyrazol-3-yl)-pyridin-2-yloxy]-quinolin-2-ylmethyl}-piperazin-1-yl)-propionitrile;
and pharmaceutically acceptable salts thereof.

In another embodiment, the invention relates to a compound selected from the group consisting of:
1-{6-[5-(2H-Pyrazol-3-yl)-pyridin-2-yloxy]-naphthalen-2-ylmethyl}-azetidin-3-ol;
1-{6-[5-(2H-Pyrazol-3-yl)-pyridin-2-yloxy]-naphthalen-2-ylmethyl}-azetidine-3-carboxylic acid amide;
N-(1-{6-[5-(2H-Pyrazol-3-yl)-pyridin-2-yloxy]-naphthalen-2-ylmethyl}-azetidin-3-yl)-acetamide;
(1-{6-[5-(2H-Pyrazol-3-yl)-pyridin-2-yloxy]-naphthalen-2-ylmethyl}-azetidin-3-yl)-methanol;
(S)-1-{6-[5-(2H-Pyrazol-3-yl)-pyridin-2-yloxy]-naphthalen-2-ylmethyl}-pyrrolidin-3-ol;
(R)-1-{6-[5-(2H-Pyrazol-3-yl)-pyridin-2-yloxy]-naphthalen-2-ylmethyl}-pyrrolidin-3-ol;
2-Hydroxy-1-(4-{6-[5-(2H-pyrazol-3-yl)-pyridin-2-yloxy]-naphthalen-2-ylmethyl}-piperazin-1-yl)-ethanone;
2-Hydroxy-N-(1-{6-[5-(2H-pyrazol-3-yl)-pyridin-2-yloxy]-naphthalen-2-ylmethyl}-piperidin-4-yl)-acetamide;

2-{6-[5-(2H-Pyrazol-3-yl)-pyridin-2-yloxy]-naphthalen-2-ylmethyl}-2-aza-spiro[3.3]heptan-6-ol;
3-Methyl-1-{6-[5-(2H-pyrazol-3-yl)-pyridin-2-yloxy]-naphthalen-2-ylmethyl}-azetidin-3-ol;
N-((R)-1-{6-[5-(2H-Pyrazol-3-yl)-pyridin-2-yloxy]-naphthalen-2-ylmethyl}-pyrrolidin-3-yl)-acetamide;
N-((S)-1-{6-[5-(2H-Pyrazol-3-yl)-pyridin-2-yloxy]-naphthalen-2-ylmethyl}-pyrrolidin-3-yl)-acetamide;
(S)-1-{6-[5-(2H-Pyrazol-3-yl)-pyridin-2-yloxy]-naphthalen-2-ylmethyl}-piperidin-3-ol;
(R)-1-{6-[5-(2H-Pyrazol-3-yl)-pyridin-2-yloxy]-naphthalen-2-ylmethyl}-piperidin-3-ol;
2-(Methyl-{6-[5-(2H-pyrazol-3-yl)-pyridin-2-yloxy]-naphthalen-2-ylmethyl}-amino)-ethanol;
(1-{6-[5-(2H-Pyrazol-3-yl)-pyridin-2-yloxy]-naphthalen-2-ylmethyl}-piperidin-4-yl)-methanol;
((S)-1-{6-[5-(2H-Pyrazol-3-yl)-pyridin-2-yloxy]-naphthalen-2-ylmethyl}-pyrrolidin-3-yl)-methanol;
2-Hydroxy-1-[(R)-3-(methyl-{6-[5-(2H-pyrazol-3-yl)-pyridin-2-yloxy]-naphthalen-2-ylmethyl}-amino)-pyrrolidin-1-yl]-ethanone;
2-Hydroxy-N-methyl-N-((S)-1-{6-[5-(2H-pyrazol-3-yl)-pyridin-2-yloxy]-naphthalen-2-ylmethyl}-pyrrolidin-3-yl)-acetamide;
2-Hydroxy-N-methyl-N-((R)-1-{6-[5-(2H-pyrazol-3-yl)-pyridin-2-yloxy]-naphthalen-2-ylmethyl}-pyrrolidin-3-yl)-acetamide;
((R)-1-{6-[5-(2H-Pyrazol-3-yl)-pyridin-2-yloxy]-naphthalen-2-ylmethyl}-pyrrolidin-3-yl)-methanol; and
2-Hydroxy-1-[(S)-3-(methyl-{6-[5-(2H-pyrazol-3-yl)-pyridin-2-yloxy]-naphthalen-2-ylmethyl}-amino)-pyrrolidin-1-yl]-ethanone;
and pharmaceutically acceptable salts thereof.

In another embodiment, the invention relates to a compound selected from the group consisting of:
1-(1-{(R)-6-[5-(2H-Pyrazol-3-yl)-pyridin-2-yloxy]-2,3-dihydro-benzofuran-2-ylmethyl}-piperidin-4-yl)-pyrrolidin-2-one;
1-(1-{(S)-6-[5-(2H-Pyrazol-3-yl)-pyridin-2-yloxy]-2,3-dihydro-benzofuran-2-ylmethyl}-piperidin-4-yl)-pyrrolidin-2-one;
1-[1-(2-{6-[5-(2H-Pyrazol-3-yl)-pyridin-2-yloxy]-benzofuran-3-yl}-ethyl)-piperidin-4-yl]-pyrrolidin-2-one;
(S)-3-Hydroxy-1-[1-(2-{6-[5-(2H-Pyrazol-3-yl)-pyridin-2-yloxy]-benzofuran-3-yl}-ethyl)-piperidin-4-yl]-pyrrolidin-2-one;
2-Methoxy-1-[4-(2-{6-[5-(2H-pyrazol-3-yl)-pyridin-2-yloxy]-benzofuran-3-yl}-ethyl)-piperazin-1-yl]-ethanone;
(R)-2-Methoxy-1-[4-(2-{6-[5-(2H-pyrazol-3-yl)-pyridin-2-yloxy]-benzofuran-3-yl}-ethyl)-piperazin-1-yl]-propan-1-one;
1-(4-{6-[5-(2H-Pyrazol-3-yl)-pyridin-2-yloxy]-benzofuran-3-ylmethyl}-[1,4]diazepan-1-yl)-ethanone;
1-{6-[5-(2H-Pyrazol-3-yl)-pyridin-2-yloxy]-benzofuran-3-ylmethyl}-piperidine-4-carboxylic acid methylamide;
N-(1-{6-[5-(2H-Pyrazol-3-yl)-pyridin-2-yloxy]-benzofuran-3-ylmethyl}-piperidin-4-yl)-acetamide;
N-(1-{6-[5-(2H-Pyrazol-3-yl)-pyridin-2-yloxy]-benzofuran-3-ylmethyl}-piperidin-4-yl)-methanesulfonamide;
N-(1-{6-[5-(2H-Pyrazol-3-yl)-pyridin-2-yloxy]-benzofuran-3-ylmethyl}-piperidin-4-ylmethyl)-acetamide;
1-{4-[({6-[5-(2H-Pyrazol-3-yl)-pyridin-2-yloxy]-benzofuran-3-ylmethyl}-amino)-methyl]-piperidin-1-yl}-ethanone;
1-[4-({6-[5-(2H-Pyrazol-3-yl)-pyridin-2-yloxy]-benzofuran-3-ylmethyl}-amino)-piperidin-1-yl]-ethanone;
(S)-3-Hydroxy-1-(1-{6-[5-(2H-pyrazol-3-yl)-pyridin-2-yloxy]-benzofuran-3-ylmethyl}-piperidin-4-yl)-pyrrolidin-2-one;
2-Methyl-8-{6-[5-(2H-pyrazol-3-yl)-pyridin-2-yloxy]-benzofuran-3-ylmethyl}-2,8-diaza-spiro[4.5]decan-1-one;
2-(4-{6-[5-(2H-Pyrazol-3-yl)-pyridin-2-yloxy]-benzofuran-3-ylmethyl}-piperazin-1-yl)-1-pyrrolidin-1-yl-ethanone;
2-Hydroxy-N-methyl-N-((R)-1-{6-[5-(2H-pyrazol-3-yl)-pyridin-2-yloxy]-benzofuran-3-ylmethyl}-pyrrolidin-3-yl)-acetamide;
2-Hydroxy-N-methyl-N-((S)-1-{6-[5-(2H-pyrazol-3-yl)-pyridin-2-yloxy]-benzofuran-3-ylmethyl}-pyrrolidin-3-yl)-acetamide; and
2-Hydroxy-1-(7-{6-[5-(2H-pyrazol-3-yl)-pyridin-2-yloxy]-benzofuran-3-ylmethyl}-2,7-diaza-spiro[4.4]non-2-yl)-ethanone;
and pharmaceutically acceptable salts thereof.

All terms as used herein in this specification, unless otherwise stated, shall be understood in their ordinary meaning as known in the art. Other more specific definitions are as follows:

Unless otherwise defined, the phrases "compound of the invention" and "compounds of the invention" refer to the compounds described in any one of the embodiments above.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1\text{-}C_4)$alkyl$^{4+}$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the examples presented below, and methods known to those of ordinary skill in the art and reported in the chemical literature. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section.

EXAMPLES

General Methods

Unless noted otherwise, all reactions are run at ambient temperature (about 25° C.), under inert atmosphere (e.g., Argon, $N_2$), and under anhydrous conditions. All compounds are characterized by at least one of the following methods: $^1$H NMR, HPLC, HPLC-MS, and melting point.

Typically, reaction progress is monitored by thin layer chromatography (TLC) or HPLC-MS. Intermediates and products are purified using at least one of the following methods:

Flash chromatography on silica gel,

Recrystallization,

Chiral HPLC using a 20×500 mm Chiralpak AD-H column, or 20×500 mm Chiralpak OD-H column, and eluting with an isocratic mixture of isopropanol in heptanes with 0.1% diethylamine (DEA) at 7.5 mL/min, 20×250 mm Chiralcel OD-H column, and eluting with an isocratic mixture of isopropanol in heptanes at 7.5 mL/min, Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or RP-HPLC using a C18 semi-preparative column eluting with a gradient of MeCN+0.1% TFA/$H_2O$+0.1% TFA, or MeCN+0.1% formic acid/$H_2O$+0.1% formic acid.

The reported MS data is for observed [M+H]$^+$. For bromine containing compounds, the [M+H]$^+$ is either reported for one or both of the bromine isotopes (i.e., $^{79}$Br and $^{81}$Br).

Compounds of the invention are characterized using LC/MS/MS with electron spray ionization (ESI). The LC method includes the following parameters:

Injection volume: 5 uL

Mobile Phases: 0.1% Formic Acid in Water (A) and 0.1% Formic Acid in Acetonitrile (B) (HPLC grade)

Left and Right Temperature: 35° C.

Run Time: 4 min

Column: Thermo Scientific, Aquasil C18, 50×2.1 mm, 5µ, part number 77505-052130, or equivalent LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.0 | 500 | 90.0 | 10.0 |
| 4.0 | 500 | 90.0 | 10.0 |

Synthesis of Intermediates

Intermediate A

Preparation of 2-Chloro-5-[2-(2-trimethylsilanyl-ethoxymethyl)-2H-pyrazol-3-yl]-pyridine (A)

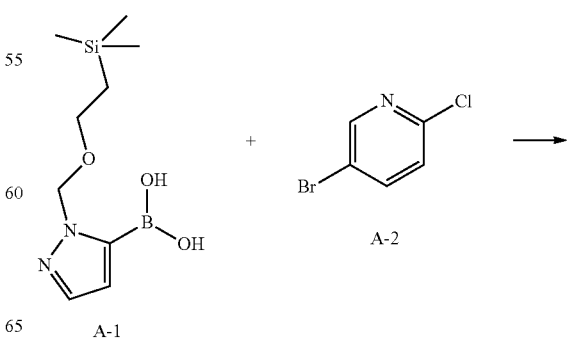

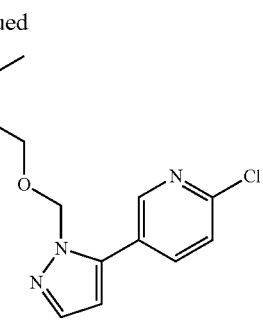

A

To a mixture of A-1 (16.0 g, 83.1 mmol) and A-2 (24.1 g, 99.6 mmol) in THF (200 mL) is added an aqueous solution of Na₂CO₃ (26.0 g, 100 mL of water). The mixture is sparged with Ar for 30 min. Next, tetrakis(triphenylphosphine)palladium(0) (1.92 g, 1.66 mmol) is added and the resultant mixture is heated at 76° C. for 16 h. The mixture is diluted with water (400 mL) and extracted with EtOAc (2×150 mL). Phases are separated, and the aqueous layer is extracted with EtOAc (100 mL). The combined organic layers are washed with brine (150 mL), dried over Na₂SO₄, filtered and concentrated. The residue is purified on SiO₂ (0-40% EtOAc in heptane) to give the title product (A).

Intermediate B

Preparation of 4-[2-(2-Trimethylsilanyl-ethoxymethyl)-2H-pyrazol-3-yl]-phenol (B)

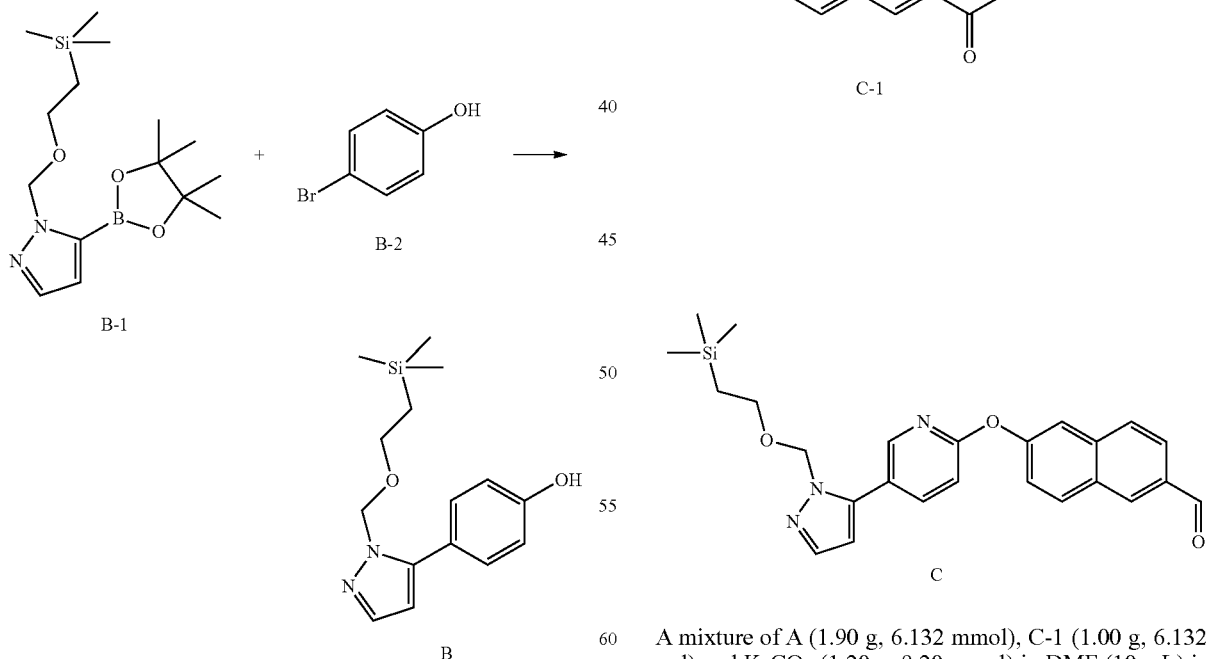

B

A suspension of B-1 (5.6 g, 17 mmol), B-2 (2.5 g, 14 mmol), Tetrakis(triphenylphosphine)palladium(0) (1.6 g, 1.4 mmol) in a mixture of DME (75 mL) and aqueous Na₂CO₃ (2 N, 22 mL) is evacuated and purged thrice with argon, and heated at 100° C. for 16 hours. Upon cooling, the reaction is diluted with EtOAc, washed with water, brine and dried over Na₂SO₄, filtered and concentrated. The residue is purified on SiO₂ (10-60% EtOAc in heptane) to give the title product (B).

Intermediate C

Preparation of 6-{5-[2-(2-Trimethylsilanyl-ethoxymethyl)-2H-pyrazol-3-yl]-pyridin-2-yloxy}-naphthalene-2-carbaldehyde (C)

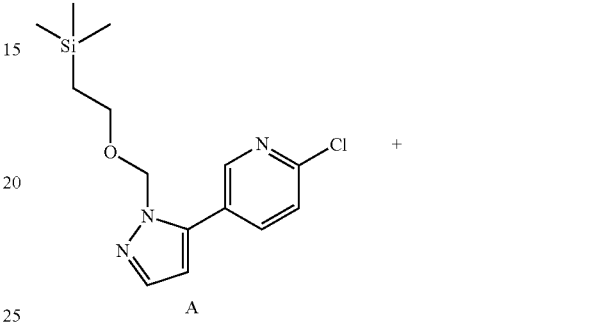

A

C-1

C

A mixture of A (1.90 g, 6.132 mmol), C-1 (1.00 g, 6.132 mmol) and K₂CO₃ (1.20 g, 9.20 mmol) in DMF (10 mL) is stirred at 120° C. After 2 days, the mixture is poured into water and thrice extracted with EtOAc. The combined organic extracts are washed with water and brine, dried over Na₂SO₄, filtered and concentrated. The residue is purified by flash chromatography (0-40% EtOAc/heptane) to give the title product (C). MS (ES+): m/z 446.2 [M+H]⁺

Intermediate D

Preparation of 6-{5-[2-(2-Trimethylsilanyl-ethoxymethyl)-2H-pyrazol-3-yl]-pyridin-2-yloxy}-quinoline-2-carbaldehyde (D)

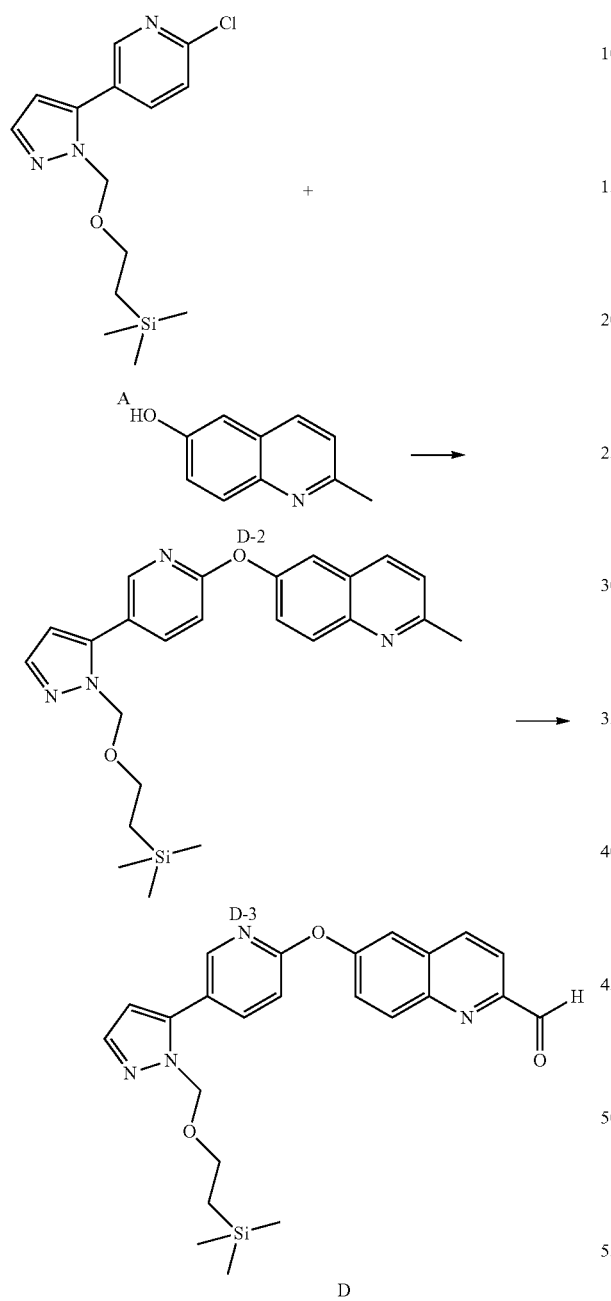

A solution of A (31.0 g, 100 mmol) and D-2 (17.5 g, 110 mmol) in DMSO (300 mL) is treated with K$_2$CO$_3$ (69.0 g, 500 mmol) and the mixture is sparged with argon for 5 minutes. The reaction is warmed to 130° C. under an Ar atmosphere overnight. After cooling to room temperature, the mixture is poured into water (1000 mL), neutralized to pH 7 with aqueous 1N HCl and is extracted with EtOAc (3×300 mL). The extracts are combined, washed with water (4×300 mL) and brine (300 mL), dried over Na$_2$SO$_4$, filtered and concentrated. The residue is dissolved in a minimum amount of DCM, treated with activated charcoal, filtered through Diatomaceous earth, and concentrated to afford the crude intermediate D-3.

Selenium dioxide (11.4 g, 103 mmol) is added to a solution of D-3 (37.0 g, 85.5 mmol) in 1,4-dioxane (300 mL). The reaction is then warmed to 100° C. for 3.5 h, cooled to ambient temperature, filtered through Diatomaceous earth, and concentrated. The residue is dissolved in dichloromethane (300 mL) and passed though Diatomaceous earth, and concentrated. The residue is passed through a bed of silica gel (400 g), eluting with a gradient of 0-40% EtOAc in heptanes (10% increase in gradient every 1 L, and holding at 40% until product eluted). The fractions containing the product are pooled and concentrated. The residue is triturated with heptanes and the resultant solid is filtered to afford the title compound (D).

Intermediate E

Preparation of 5-[4-[2-(2-trimethylsilylethoxymethyl)pyrazol-3-yl]phenoxy]pyridin-2-amine (E)

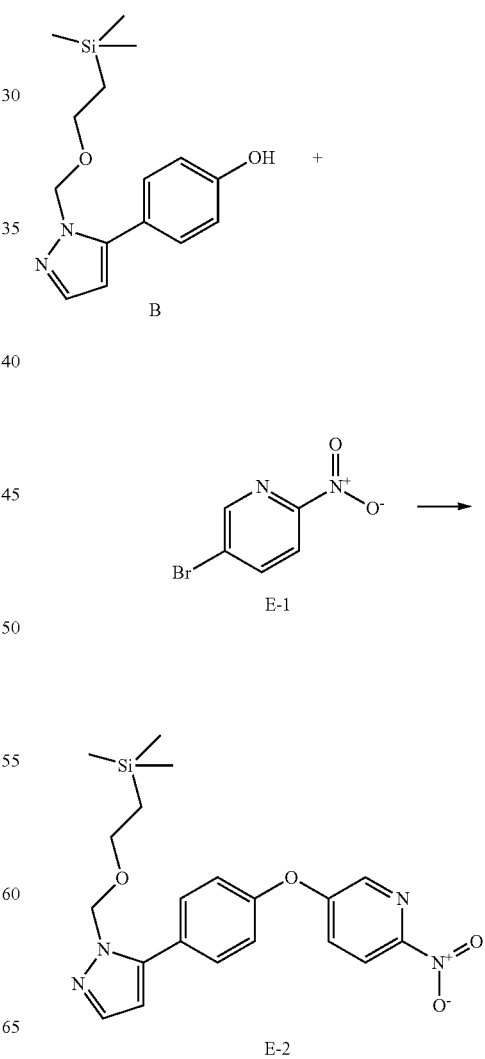

63

-continued

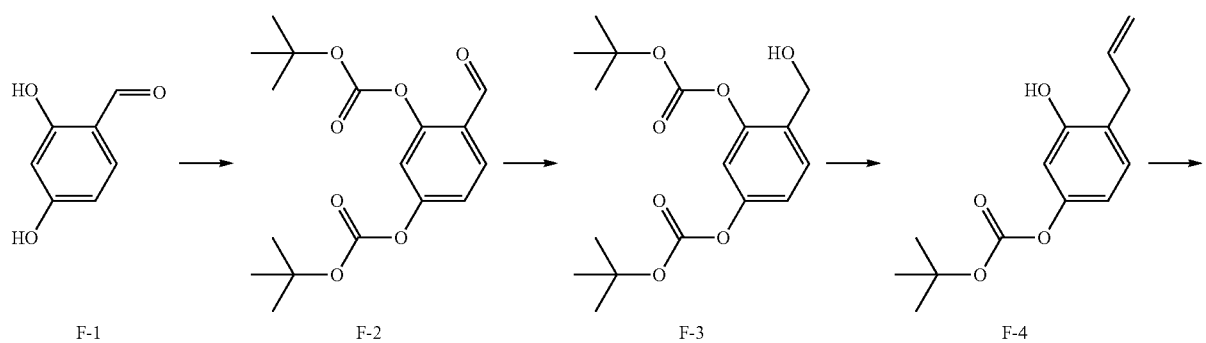

E

To a stirred solution of intermediate B (2.00 g, 6.89 mmol) in DMF (15 mL) is added cesium carbonate (4.50 g, 13.8 mmol). After 20 min, E-1 (1.50 g, 7.58 mmol) is added

64 and the mixture is stirred at 60° C. for 2 h. The mixture is diluted with EtOAc (50 mL) and washed with water (2×10 mL). The organic layer is dried over Na$_2$SO$_4$, filtered and concentrated. The residue is purified by flash chromatography (0-50% EtOAc in heptane) to give E-2.

A solution of E-2 (1.87 g, 4.53 mmol) in MeOH (45 mL) is treated with Pd (10% on carbon, 200 mg). The mixture is stirred under an atmosphere of H$_2$ for 3 h, filtered and concentrated. The residue is purified by flash chromatography (0-6% MeOH in DCM) to give title product (E).

Intermediate F

Preparation of Methanesulfonic acid 6-{5-[2-(2-trimethylsilanyl-ethoxymethyl)-2H-pyrazol-3-yl]-pyridin-2-yloxy}-2,3-dihydro-benzofuran-2-ylmethyl ester (F)

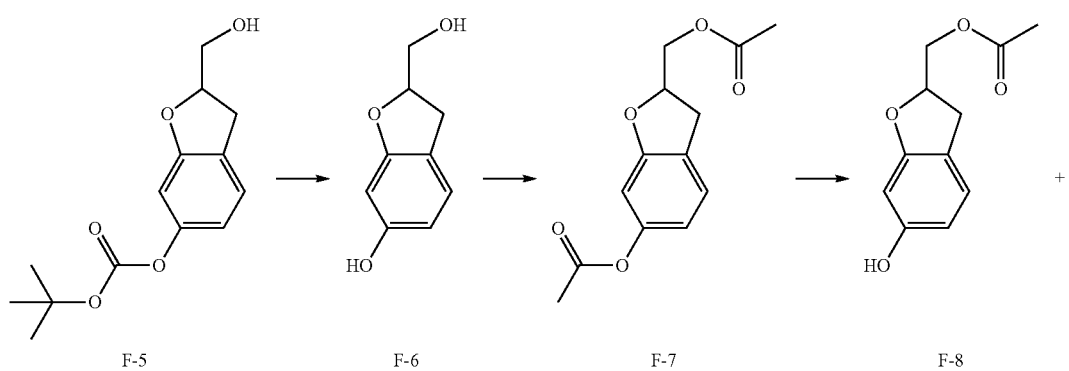

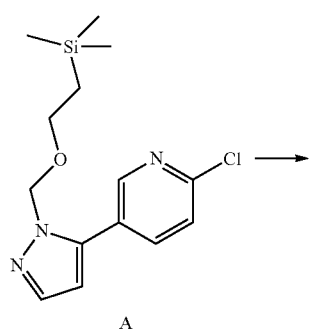

A

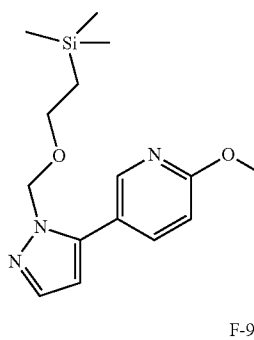 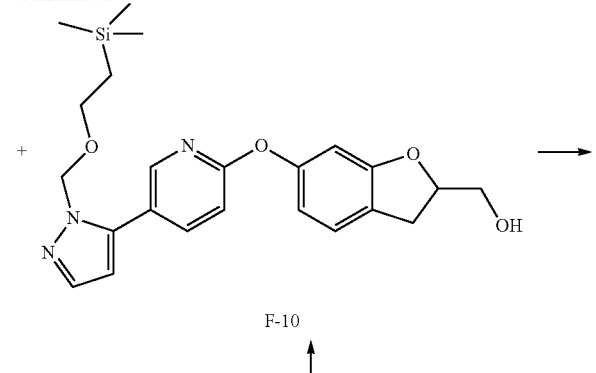

F-9 + F-10 →

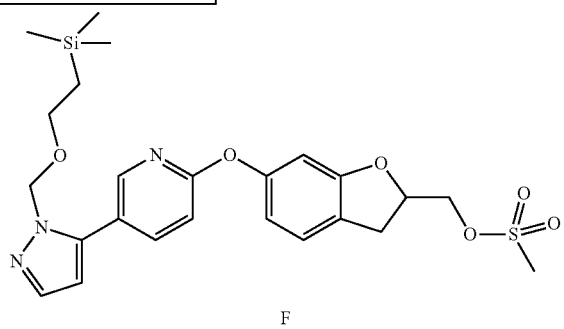

F

To a solution of F-1 (10.0 g, 72.4 mmol) in dry THF (100 mL) is added BOC anhydride (33.2 g, 152 mmol), DIPEA (30.0 mL, 160 mmol) and DMAP (7 mmol). The mixture is stirred overnight, diluted with EtOAc (700 mL), washed with saturated aqueous NH$_4$Cl (2×500 mL), H$_2$O (2×500 mL) and brine (500 mL), dried over MgSO$_4$, filtered and concentrated to give F-2.

To a solution of F-2 (24.0 g, 70.9 mmol) in THF (500 mL) at 4° C. is added BH$_3$.DMS (7.31 mL, 77.0 mmol). The mixture is stirred for 3 h and warmed to ambient temperature, placed in a water bath and quenched with 0.1 M HCl. The mixture is diluted with Et$_2$O (500 mL), washed with water (2×200 mL), and brine (200 mL), dried over MgSO$_4$, filtered and concentrated. The residue is purified on a SiO$_2$ column (0-25% EtOAc in heptane) to afford F-3.

To vinylMgBr (140 mL, 1.0 M in THF) at 4° C. is added F-3 (15.4 g, 45.2 mmol) in Et$_2$O (200 mL+100 ML rinse). The mixture is warmed slowly to ambient temperature and stirred for 3 h, quenched with 0.1 M HCl (100 mL), and diluted with Et$_2$O (500 mL). Phases are separated, and the organic layer is washed with H$_2$O (500 mL). The aqueous phase is extracted with Et$_2$O (200 mL). The combined organic layers are washed with brine (500 mL), dried over MgSO$_4$, filtered and concentrated. The residue is purified on a SiO$_2$ column (0-25% EtOAc in heptane) to give F-4.

To a stirred solution of F-4 (11.3 g, 45.3 mmol) in DCM (200 ML) is added mCPBA (77%, 10.3 g, 46.2 mmol). The solution is stirred at ambient temperature for 5 h, diluted with EtOAc (400 mL), and sequentially washed with 10% Sodium sulfite (50 mL) and saturated aqueous K$_2$CO$_3$ (300 mL). The organic layer is dried over MgSO$_4$, filtered and concentrated. The residue is re-dissolved DCM (1 L), and treated with SiO$_2$ (500 mL). The mixture is stirred overnight and filtered. The SiO$_2$ pad is washed with DCM (1.5 L) and EtOAc (3 L). The filtrates are concentrated separately. The residue from DCM wash is purified on a SiO$_2$ column (0-50% EtOAc in heptane). The desired fractions are pooled and combined with the residue from EtOAc wash to give F-5.

To a solution of F-5 (9.40 g, 35.3 mmol) in MeOH (150 mL) is added K$_2$CO$_3$ (9.0 g). The mixture is stirred for 1 h and concentrated. The residue is treated with H$_2$O (200 mL), neutralized with AcOH, and extracted with EtOAc (2×400 mL). The combined organic layers are washed with brine (200 mL), dried over MgSO$_4$, filtered and concentrated to give F-6.

To a solution of F-6 (5.94 g, 35.7 mmol) in DCM (250 mL) at 4° C. is added DIPEA (13 mL, 75.8 mmol) and acetyl chloride (7.85 g, 100 mmol). The mixture is stirred for 16 h, concentrated and diluted with EtOAc (500 mL). The organic phase is washed with saturated aqueous NaHCO$_3$ (3×100 mL), saturated aqueous NH$_4$Cl (2×100 mL), and brine (200 mL), dried over MgSO$_4$, filtered and concentrated to give F-7.

To a solution of F-7 (8.90 g, 35.6 mmol) in a 4:1 mixture of MeOH/H$_2$O (100 mL) is added NH$_4$OAc (20 g). The mixture is stirred for 16 h, additional NH$_4$OAc (20 g) is added and the mixture is heated at 50° C. for 3 h. The mixture is concentrated; the resultant residue is dissolved in H$_2$O (200 mL) and extracted with EtOAc (2×200 mL). The combined organic extracts are washed with brine (300 mL), dried over MgSO$_4$, filtered and concentrated to give F-8.

A mixture of F-8 (6.78 g, 32.6 mmol), A (20.2 g, 65.1 mmol) and K$_2$CO$_3$ (22.5 g, 163 mmol) in DMSO (100 mL) is heated in a sealed flask at 160° C. for 4 h. The reaction mixture is cooled to ambient temperature, diluted with EtOAc (500 mL) and washed with H$_2$O (2×400 mL). The aqueous phase is extracted with EtOAc (500 mL). The organic extracts are combined and washed with brine (600 mL), dried over MgSO$_4$, filtered and concentrated. The residue is purified on a SiO$_2$ column (0-50% EtOAc in heptane) to give F-9 and F-10.

To a solution of F-9 (10.1 g, 20.9 mmol) in a 1:5 mixture of H₂O/MeOH (100 mL) is added solid K₂CO₃ (10.0 g), and the resultant mixture is stirred at 50° C. for 2 h. The reaction is cooled to ambient temperature and concentrated. The residue is suspended in H₂O (300 mL), treated with AcOH until gas evolution ceased and extracted with EtOAc (2×500 mL). The combined organic layers are washed with brine (500 mL), dried over MgSO4, filtered and concentrated to give F-10.

To a solution of F-10 (262 mg, 0.600 mmol) in DCM (10 ML) is added DIPEA (0.440 mL, 2.40 mmol) and methanesulfonyl chloride (0.120 mL, 1.50 mmol). The mixture is stirred for 2 h at ambient temperature, diluted with EtOAc (50 mL), and quenched with saturated aqueous NH₄Cl (20 mL). Phases are separated and the organic layer is washed with saturated aqueous K₂CO₃ (2×20 mL) and brine (20 mL), dried over MgSO4, filtered and concentrated to give the title product (F).

Intermediate G

Preparation of 6-{5-[2-(2-Trimethylsilanyl-ethoxymethyl)-2H-pyrazol-3-yl]-pyridin-2-yloxy}-benzofuran-3-carbaldehyde (G)

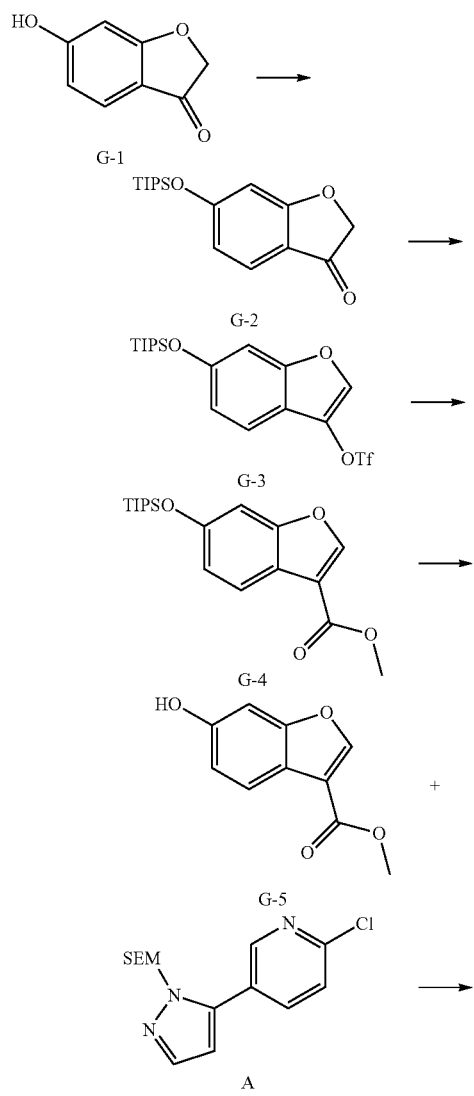

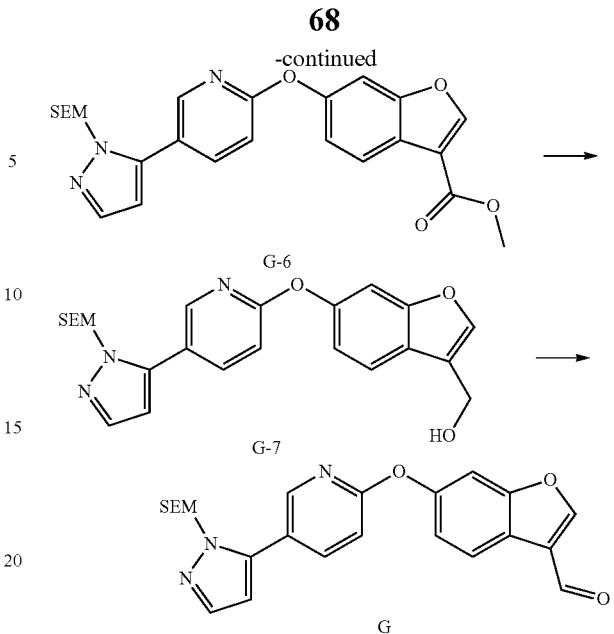

To a solution of G-1 (10.2 g, 65.7 mmol) and 1H-imidazole (10.8 g, 157 mmol) in DMF (80 mL) is added chlorotriisopropylsilane (17.4 mL, 78.9 mmol) and the reaction is stirred at ambient temperature for 2 h. The reaction is diluted with EtOAc (400 mL) and washed with water (400 mL) and brine (200 mL). The aqueous layers are extracted with EtOAc (400 mL), and the combined organic layers are dried over Na₂SO₄, filtered and concentrated. The residue is purified by silica gel chromatography (0-25% EtOAc in heptane) to afford G-2.

To a solution of G-2 (1.00 g, 3.17 mmol) in DCM (20 mL) at 0° C. is added 2,6-lutidine (0.405 mL, 3.48 mmol) and trifluoromethanesulfonic anhydride (0.582 mL, 3.48 mmol) over 2 min. The stirred mixture is warmed to ambient temperature over 45 min, cooled to 0° C., quenched with saturated aqueous NH₄Cl (50 mL) and extracted with EtOAc (2×50 mL). The combined organic layers are dried over Na₂SO₄ and concentrated. The crude is purified by silica gel chromatography (100% heptane) to give G-3.

To a mixture of G-3 (100 mg, 0.228 mmol) in DMF (2 mL) is added Mo(CO)₆ (61 mg, 0.23 mmol) and trans-di-mu-acetobis[2-(di-O-tolylphosphino)benzyl]dipalladium(II) (Hermann's Catalyst, 22 mg, 0.023 mmol). The reaction is heated at 100° C. in a microwave for 15 min, cooled to ambient temperature, quenched with 1M HCl (20 mL) and extracted with EtOAc (2×20 mL). The combined organic layers are dried over Na₂SO₄ and concentrated. The crude is purified by prep-TLC (10% EtOAc in heptane) to give G-4.

To a stirred solution of G-4 (110 mg, 0.316 mmol) in THF (5 mL) at ambient temperature is added TBAF (1.0M in THF, 0.325 mL). After 24 h, the reaction is quenched with water (40 mL) and extracted with EtOAc (3×50 mL). The combined organic layers are dried over Na₂SO₄ and concentrated to give G-5.

A mixture of G-5 (51.0 mg, 0.260 mmol), A (107 mg, 0.335 mmol), and K₂CO₃ (108 mg, 0.772 mmol) in DMSO (2 mL) is heated at 150° C. for 3 h. The reaction is quenched with water (50 mL) and is extracted with EtOAc (3×50 mL). The combined organic layers are washed with brine (30 mL), dried over Na₂SO₄, filtered and concentrated. The residue is purified by silica gel chromatography (0-30% EtOAc in heptane) to give G-6.

To a solution of G-6 (41.0 mg, 0.0870 mmol) in THF (5 mL) at −25° C. is added LAH (1M in THF, 0.436 mL). The mixture is warmed to ambient temperature over 1 h. LCMS indicates presence of starting material. The mixture is cooled to −25° C. and more LAH (1M in THF, 0.218 mL) is added. The reaction is stirred at ambient temperature for 1 h, quenched with saturated solution of Rochelle salt (75 mL) and extracted with EtOAc (2×100 mL). The combined organic layers are washed with brine (50 mL) and dried over Na$_2$SO$_4$, filtered and concentrated. The residue is purified by silica gel chromatography (0-55% EtOAc in heptane) to afford G-7.

To a solution of G-7 (3.36 g, 7.45 mmol) in DCM (125 mL) at 0° C. is added Dess-Martin Periodinane (3.60 g, 8.23 mmol). After 1 h at 0° C., more Dess-Martin Periodinane (7.20 g, 16.5 mmol) is added, the reaction is warmed to ambient temperature and stirred 1 h. The reaction is cooled to −10° C., quenched with saturated aqueous NaHCO$_3$ (500 mL) and stirred for 30 min. The mixture is extracted with EtOAc (3×500 mL). The combined organic layers are washed with brine (150 mL), dried over Na$_2$SO$_4$, filtered and concentrated. The residue is suspended in DCM and filtered. The filtrate is concentrated and purified by silica gel chromatography (0-50% EtOAc in heptane). The resultant residue is dissolved in EtOAc (20 mL), treated with heptane (150 mL), concentrated to 100 mL and filtered to give the title product (G).

Intermediate H

Preparation of 2-Chloro-5-[2-(2-trimethylsilanyl-ethoxymethyl)-2H-pyrazol-3-yl]-pyrimidine (H)

The title product (H) is synthesized from A-1 and H-2 according to the procedure described for the synthesis of intermediate A from A-1 and A-2.

Intermediate I

Preparation of (6-{5-[2-(2-Trimethylsilanyl-ethoxymethyl)-2H-pyrazol-3-yl]-pyridin-2-yloxy}-benzofuran-3-yl)-acetaldehyde (I)

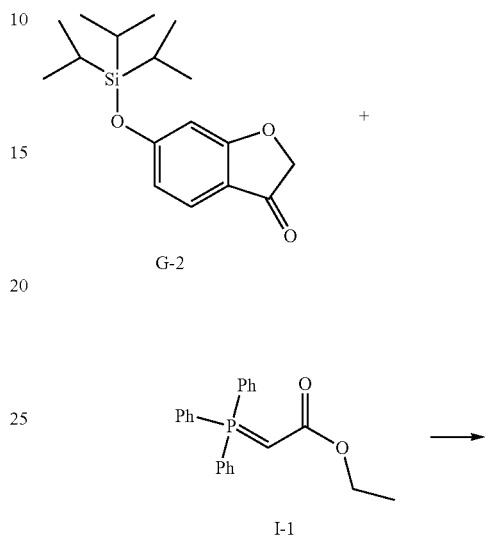

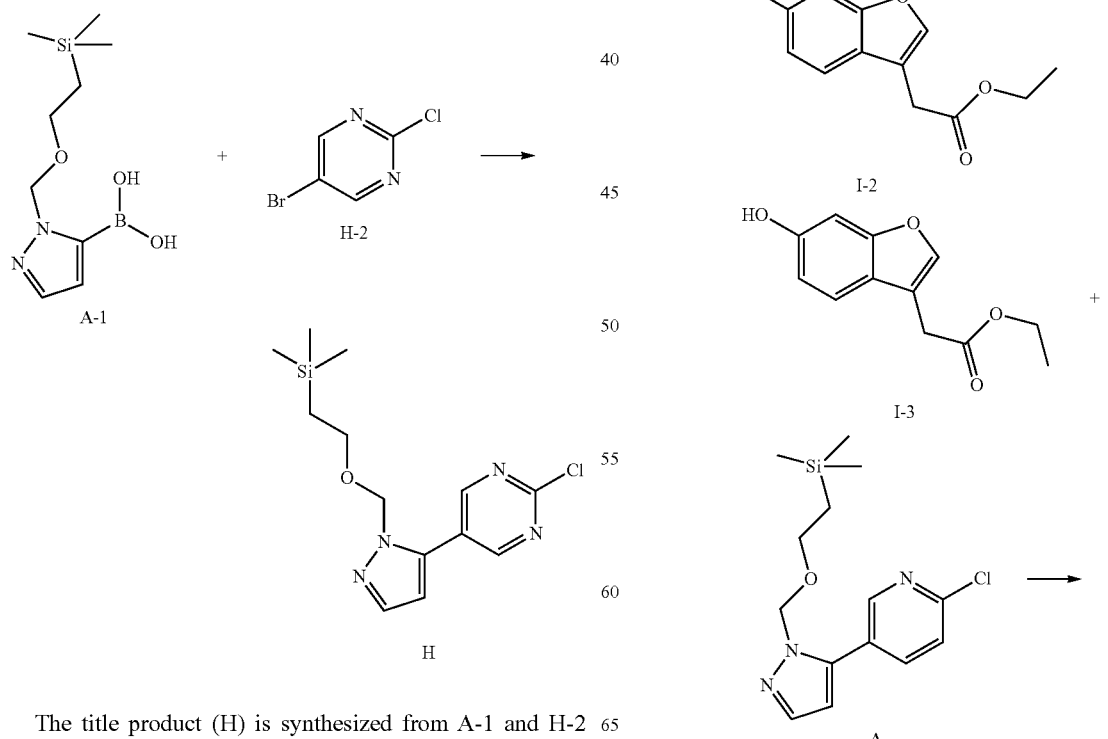

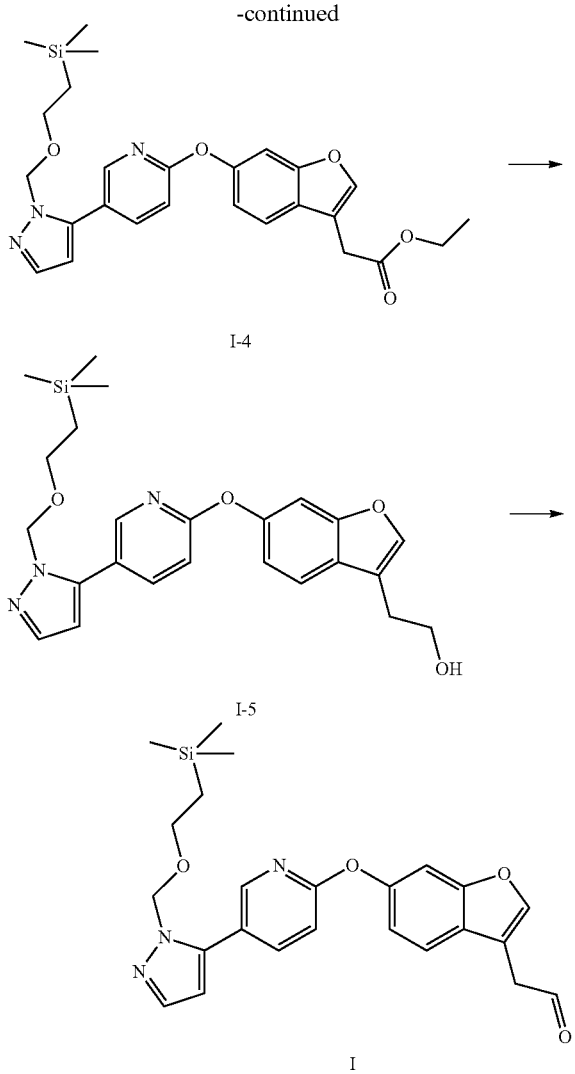

temperature for 6 h. Phases are separated, and the aqueous layer is extracted with EtOAc (2×50 mL). The combined organic layers are washed with NaHCO₃ (100 mL) and brine (100 mL), dried over MgSO₄, filtered and concentrated. The residue is purified on SiO₂ (0-70% EtOAc in heptane) to provide I-5.

To a 0° C. solution of I-5 (600 mg, 1.33 mmol) in anhydrous DCM (20 mL) is added Dess-Martin periodinane (592 mg, 1.40 mmol). The mixture is stirred at 0° C. for 30 min, quenched with saturated aqueous NaHCO₃ (20 mL), and stirred for 20 min at ambient temperature. The resultant mixture is extracted with EtOAc (3×50 mL). The combined organic layers are washed with saturated aqueous NaHCO₃ (50 mL) and brine (50 mL), dried over MgSO₄, filtered and concentrated. The mixture is purified on SiO₂ (0-50% EtOAc in heptane) to yield the title product (I).

Intermediate J

Preparation of (6-{5-[2-(2-Trimethylsilanyl-ethoxymethyl)-2H-pyrazol-3-yl]-pyridin-2-yloxy}-2,3-dihydro-benzofuran-3-yl)-acetaldehyde (J)

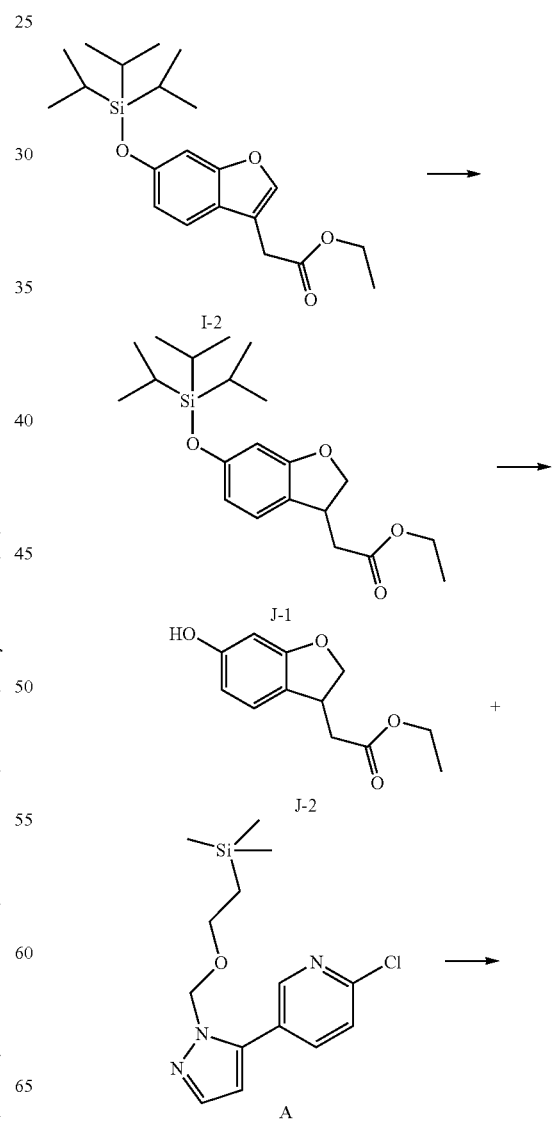

To a solution of G-2 (1.00 g, 3.26 mmol) in toluene (40 mL) is added I-1 (4.55 g, 13.0 mmol). The resultant solution is stirred at 110° C. After 78 h, the mixture is concentrated and purified on SiO₂ (0-30% EtOAc in heptane) to give I-2.

To a solution of I-2 (300 mg, 0.797 mmol) in THF (3 mL) is added TBAF (797 µL, 0.797 mmol) at ambient temperature. After 30 min, the mixture is poured into a mixture of EtOAc (100 mL) and water (100 mL). Phases are separated and the aqueous layer is extracted with EtOAc (3×30 mL). The combined organic layers are washed with water (100 mL), brine (100 mL), dried over MgSO₄, filtered and concentrated. The mixture is purified on SiO₂ (0-30% EtOAc in heptane) to give I-3.

Compound I-4 is synthesized from I-3 (787 mg, 3.57 mmol) and intermediate A (1.44 g, 4.65 mmol) according to the procedure described for the synthesis G-6 from G-5 and intermediate A.

A solution of I-4 (1.20 g, 2.43 mmol) in anhydrous THF (20 mL) is cooled to 0° C., and treated with DIBAL-H (1.5M in toluene, 1.78 mL). The mixture is stirred at 0° C. for 1 h, and warmed to ambient temperature. After 22 h, the mixture is cooled to 0° C., quenched with EtOAc (350 mL) water (100 mL), and saturated aqueous Rochelle salt solution (200 mL) while insuring that the internal temperature stayed below 10° C. The resultant mixture is stirred at ambient

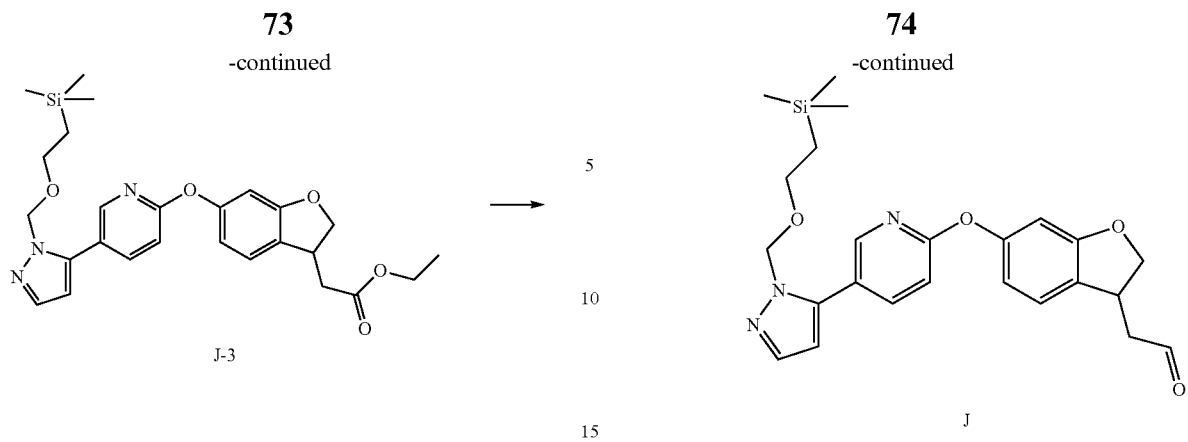

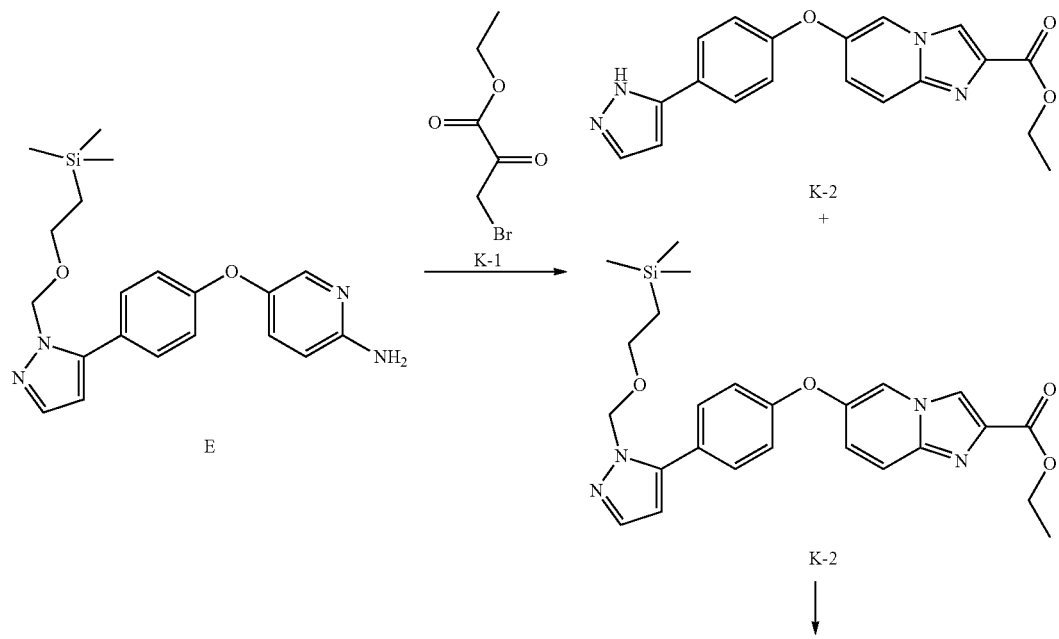

A mixture of I-2 (350 mg, 0.929 mmol) and 10% Pd/C (50 mg) in EtOAc (50 ml) is stirred under an atmosphere of $H_2$. After 4 h, the mixture is filtered through a pad of Diatomaceous earth and concentrated to give J-1.

The title product (J) is synthesized from J-1 according to procedures described for the synthesis of intermediate I from I-2.

Intermediate K

Preparation of (6-{4-[2-(2-Trimethylsilanyl-ethoxymethyl)-2H-pyrazol-3-yl]-phenoxy}-imidazo[1,2-a]pyridin-2-yl)-methanol (K)

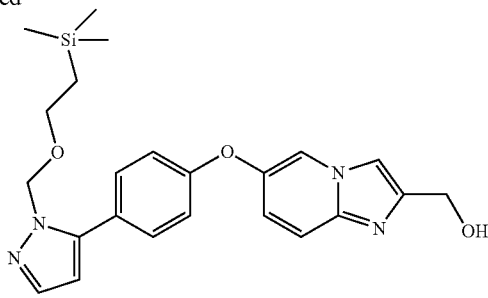

K

To a solution of E (1.11 mg, 2.91 mmol) in THF (25 ml) is added K-1 (0.43 ml, 3.4 mmol). The mixture is heated at 60° C. for 4 h, cooled to ambient temperature, washed with saturated aqueous NaHCO$_3$ and brine, and concentrated. The residue is purified on SiO$_2$ (0-10% MeOH in DCM) to give K-2 and K-3.

A solution of K-3 (355 mg, 0.740 mmol) in THF (10 ml) is treated with LAH (43 mg, 1.1 mmol). The mixture is stirred at ambient temperature for 3 h, treated with Na$_2$SO$_4$.10H$_2$O, stirred for 15 min, and filtered. The filtrate is concentrated and purified on SiO$_2$ (0-10% MeOH in DCM) to give the title product (K).

Intermediate L

Preparation of 2-Piperazin-1-ylmethyl-6-{5-[2-(2-trimethylsilanyl-ethoxymethyl)-2H-pyrazol-3-yl]-pyridin-2-yloxy}-quinoline (L)

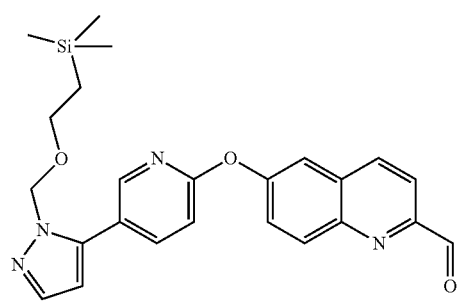

D

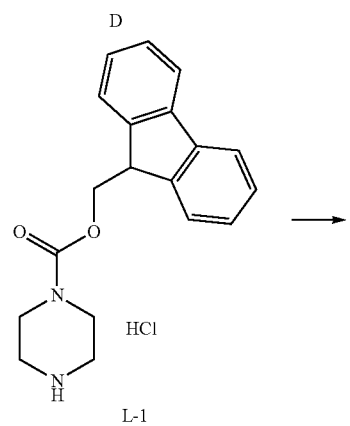

L-1

-continued

[structure L-2]

L-2

[structure L]

L

A mixture of D (7.00 g, 15.7 mmol), L-1 (6.48 g, 18.8 mmol) and DIPEA (3.25 mL, 18.8 mmol) in dry DCM (400 mL) is stirred at ambient temperature for 20 minutes, sodium triacetoxyborohydride (6.64 g, 31.4 mmol) is added, and the reaction mixture is stirred at ambient temperature. After 22 h, the mixture is diluted with DCM (200 mL). The organic layer is washed with saturated aqueous NaHCO$_3$ (400 mL), dried over MgSO$_4$, filtered and concentrated. The residue is purified on SiO$_2$ (0-10% gradient of MeOH in DCM) to give L-2.

A solution of L-2 (0.900 g, 1.04 mmol) in DMF (20 mL) is treated with piperidine (0.31 mL, 3.1 mmol) and the reaction is stirred for 16 hours. The mixture is diluted with water (200 mL) and extracted with EtOAc (3×75 mL). The combined extracts are washed with water (4×50 mL), brine (50 mL), dried over Na$_2$SO$_4$, filtered and concentrated. The residue is purified by flash chromatography (0-8% MeOH in DCM, followed by 0.5% NH₄OH, 10% MeOH in DCM) to afford the title product (L).

Intermediate M

Preparation of 3,8-Diaza-bicyclo[3.2.1]octane-3-carboxylic acid 9H-fluoren-9-ylmethyl ester.TFA (M)

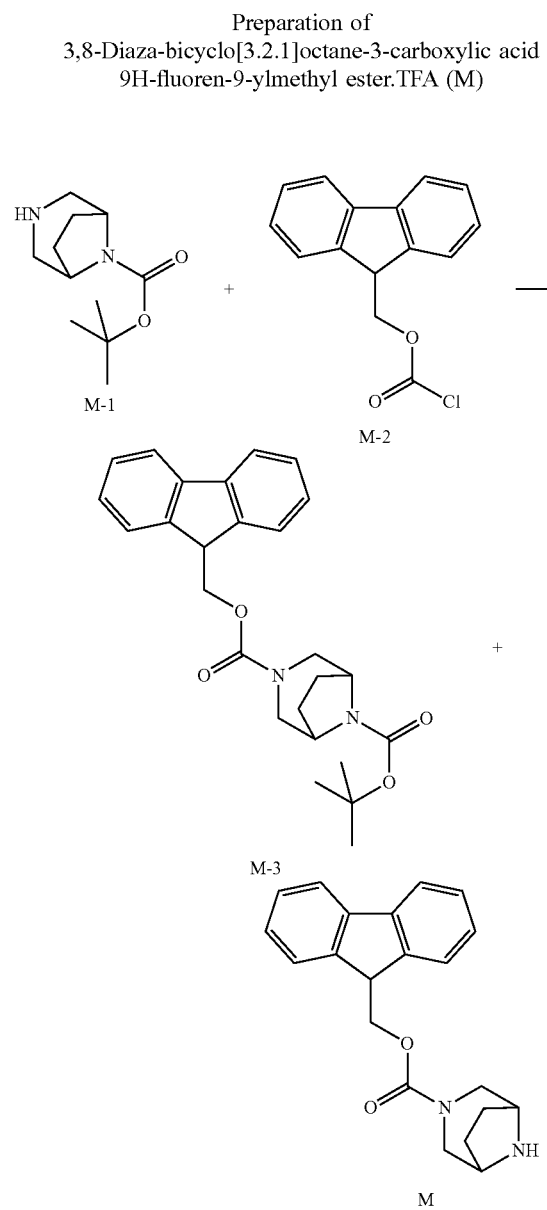

To a chilled solution of M-1 (1.00 g, 4.71 mmol) in DCM (50 mL) is added M-2 (1.22 g, 4.71 mmol) followed by DIPEA (900 µL, 5.17 mmol). After 10 h, the reaction is poured into water (100 mL) and extracted with DCM (100 mL). The organic layer is washed with 10% aqueous citric acid (100 mL), saturated aqueous NaHCO₃ (100 mL) and brine (100 mL), dried over MgSO₄, filtered and concentrated. The residue is purified on SiO₂ (0-50% EtOAc in heptane) to afford M-3.

To a stirred solution of the M-3 (1.90 g, 4.37 mmol) in DCM (10 mL) is added TFA (10 mL). After 20 h, the mixture is concentrated to give the title product (M).

Intermediate N

Preparation of 2-(3,8-Diaza-bicyclo[3.2.1]oct-8-ylmethyl)-6-{5-[2-(2-trimethylsilanyl-ethoxymethyl)-2H-pyrazol-3-yl]-pyridin-2-yloxy}-quinoline (N)

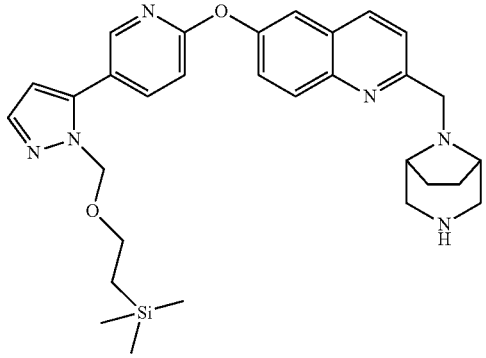

The title product (N) is synthesized from D (1.80 g, 4.03 mmol) and M (2.01 g, 4.48 mmol) according to the procedure described for the synthesis of intermediate L from D and L-1.

Intermediate O

Preparation of 1-(6-{5-[2-(2-Trimethylsilanyl-ethoxymethyl)-2H-pyrazol-3-yl]-pyridin-2-yloxy}-2,3-dihydro-benzofuran-2-ylmethyl)-piperazine (O)

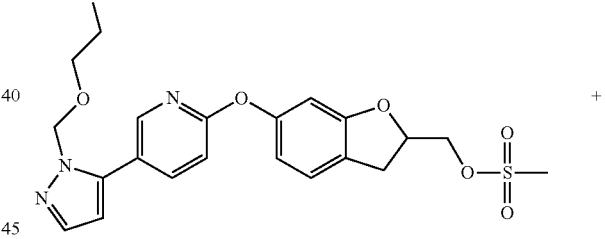

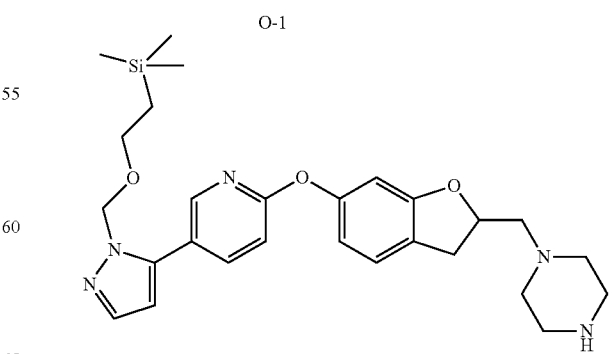

A mixture of F (350 mg, 0.676 mmol), and O-1 (1.16 g, 13.5 mmol) in DMSO (3 mL) is heated at 80° C. After 16 h, the mixture is cooled to ambient temperature, diluted with EtOAc (100 mL), washed with water (3×100 mL) and brine (100 mL), dried over MgSO₄, filtered and concentrated to give the title product (O), which is used without purification.

Intermediate P

Preparation of 1-[2-(6-{5-[2-(2-Trimethylsilanyl-ethoxymethyl)-2H-pyrazol-3-yl]-pyridin-2-yloxy}-2,3-dihydro-benzofuran-3-yl)-ethyl]-piperazine (P)

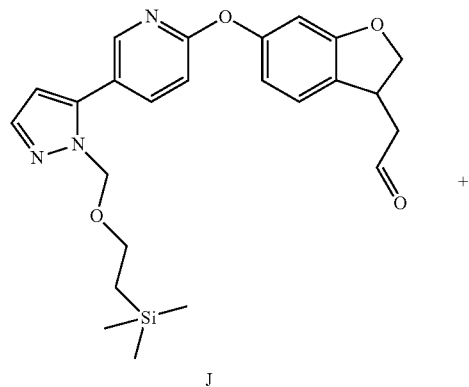

J

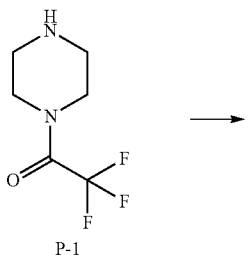

P-1

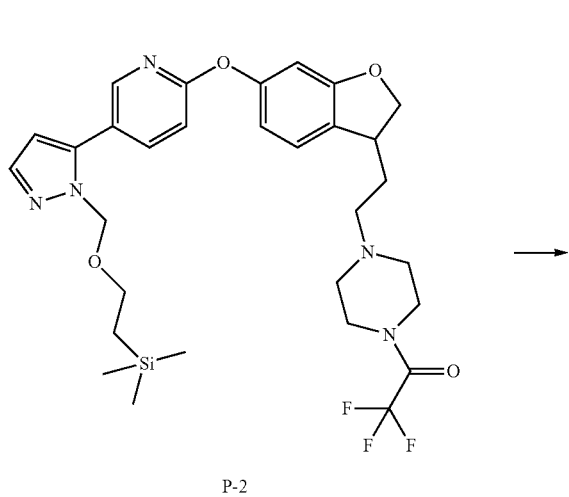

P-2

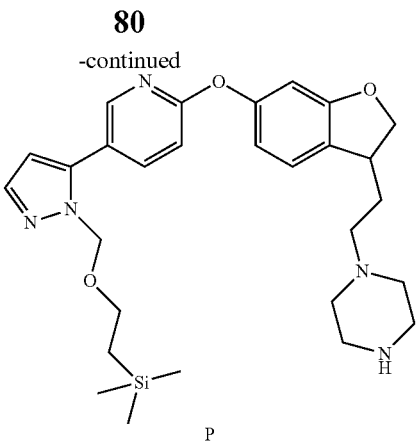

P

A mixture of J (1.00 g, 2.21 mmol), and P-1 (807 mg, 4.42 mmol) in dry DCE (40 mL) is stirred at ambient temperature. After 20 min, sodium triacetoxyborohydride (939 mg, 4.42 mmol) is added, and the mixture is stirred at ambient temperature overnight. After 22 h, the reaction is diluted with EtOAC (250 mL), washed with 10% aqueous NaHCO₃ (100 mL), dried over MgSO₄, filtered and concentrated to give P-2.

To a solution of P-2 (1.35 g, 2.18 mmol) in MeOH (40 mL) is added a solution of K₂CO₃ (1.21 g, 8.74 mmol) in water (15 mL). The mixture is stirred for 2 h at 45° C., concentrated to remove MeOH, extracted with EtOAc (250 mL), dried over MgSO₄, filtered and concentrated to afford the title product (P), which is used without purification.

Intermediate Q

Preparation of 1-[2-(6-{5-[2-(2-Trimethylsilanyl-ethoxymethyl)-2H-pyrazol-3-yl]-pyridin-2-yloxy}-benzofuran-3-yl)-ethyl]-piperazine (Q)

Q

The title product (Q) is synthesized from I (1.00 g, 2.22 mmol) and P-1 (810 mg, 4.45 mmol) according to the procedure described for the synthesis of intermediate P from J and P-1.

Intermediate R

Preparation of 2-Piperazin-1-ylmethyl-6-{4-[2-(2-trimethylsilanyl-ethoxymethyl)-2H-pyrazol-3-yl]-phenoxy}-imidazo[1,2-a]pyridine (R)

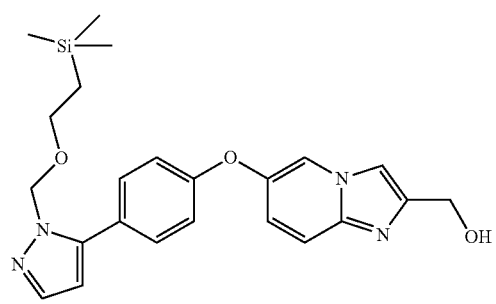

K

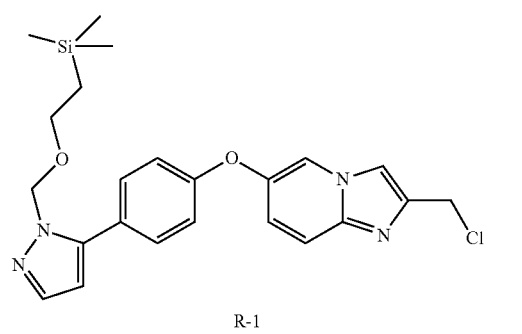

R-1

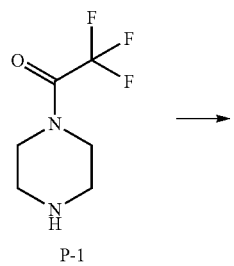

P-1

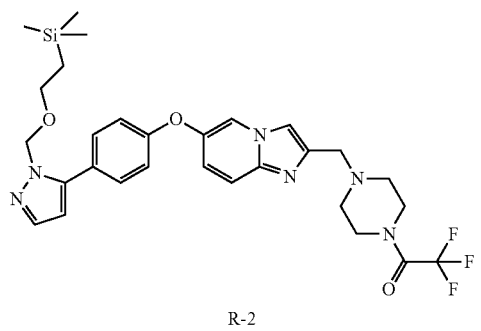

R-2

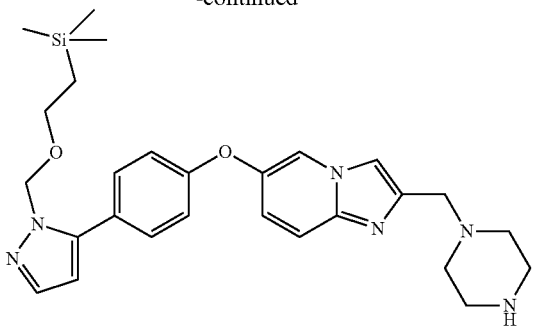

R

To a solution of K (1.50 g, 3.44 mmol) in DCM (50 mL) at 0° C. is added methanesulfonyl chloride (294 μL, 3.78 mmol) and DIPEA (1.20 mL, 6.87 mmol). The reaction is stirred for 2 h, warmed to ambient temperature and concentrated to give R-1, which is used without purification.

A solution of R-1 (1.82 g, 4.00 mmol) and P-1 (1.46 g, 8.00 mmol) in DCM (10 mL) is stirred at ambient temperature overnight. After 20 h, the mixture is concentrated and the residue is purified on $SiO_2$ eluting with a gradient of 0-10% MeOH in EtOAc to give R-2.

The title product (R) is synthesized from R-2 (1.50 g, 2.50 mmol) according to the procedure described for the synthesis of intermediate P from P-2.

Intermediate S

Preparation of Acetic acid ((R)-methyl-pyrrolidin-3-yl-carbamoyl)-methyl ester (S)

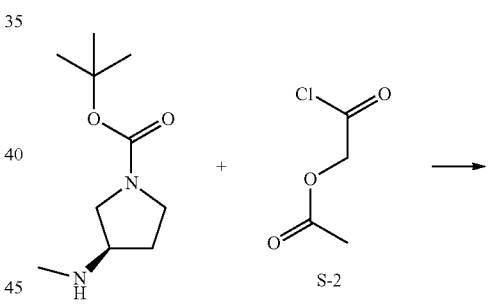

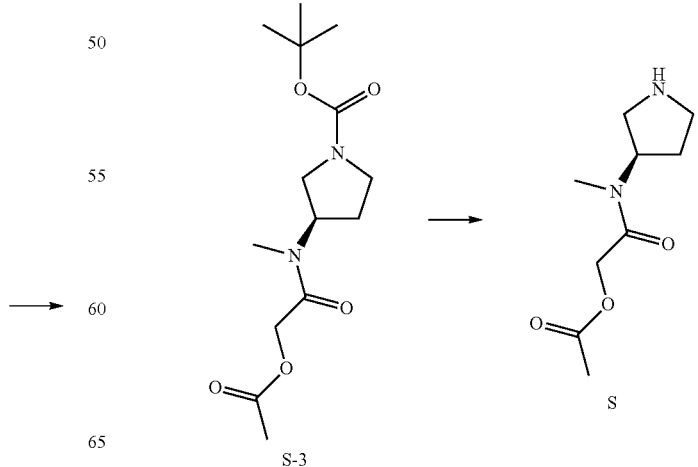

To a solution of S-1 (1.00 g, 4.84 mmol) in DCM (5 ml) at −35° C. is added DIPEA (2.61 ml, 14.5 mmol) followed by S-2 (644 µl, 5.81 mmol). The reaction is warmed up to ambient temperature over 1 h and stirred for 24 h. The mixture is diluted with EtOAc (125 ml), and washed with saturated aqueous NH₄Cl (100 ml), saturated aqueous NaHCO₃ (100 ml) and brine (40 ml). The combined aqueous layers are extracted with EtOAc (125 ml). The organic layers are pooled, dried over Na₂SO₄, filtered and concentrated to afford S-3, which is used in the next step without purification.

To a solution of S-3 (1.53 g, 4.84 mmol) in DCM (50 ml) is added HCl in 1,4-dioxane (24.7 ml, 4 M, 98.8 mmol) at ambient temperature. The mixture is stirred at ambient temperature for 24 h, concentrated in vacuo, dissolved in a mixture of MeOH and DCM (1 mL: 100 ml), treated with PS-DIEA resin (3.5 g) and stirred for 18 h. The suspension is filtered, and the filtrate is concentrated to afford the title product (S), which is used in the next step without purification.

The following intermediates are synthesized from their corresponding starting material and intermediate S-2 according to the procedure described for the synthesis of intermediate S.

| Intermediate | Structure | Intermediate Name | Starting Material |
|---|---|---|---|
| T | 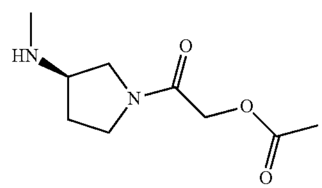 | Acetic acid 2-((R)-3-methylamino-pyrrolidin-1-yl)-2-oxo-ethyl ester | |
| U | 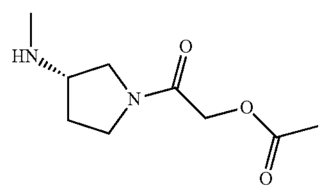 | Acetic acid 2-((S)-3-methylamino-pyrrolidin-1-yl)-2-oxo-ethyl ester | |
| V | 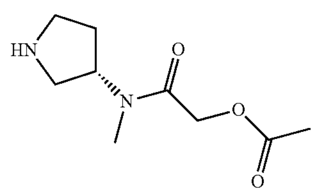 | Acetic acid ((S)-methyl-pyrrolidin-3-yl-carbamoyl)-methyl ester | |
| W | 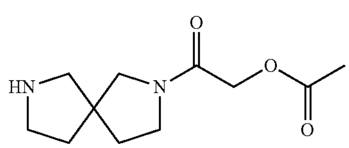 [SMILES: CC(=O)OCC(=O)N1CCC2(CCNC2)C1] | Acetic acid 2-(2,7-diaza-spiro[4.4]non-2-yl)-2-oxo-ethyl ester | |
| X | 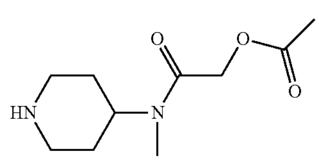 | Acetic acid (methyl-piperidin-4-yl-carbamoyl)-methyl ester | |
| Y | 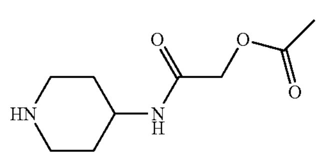 | Acetic acid (piperidin-4-ylcarbamoyl)-methyl ester | |

Intermediate Z

Preparation of 6-{5-[2-(2-Trimethylsilanyl-ethoxymethyl)-2H-pyrazol-3-yl]-pyrimidin-2-yloxy}-naphthalene-2-carbaldehyde (Z)

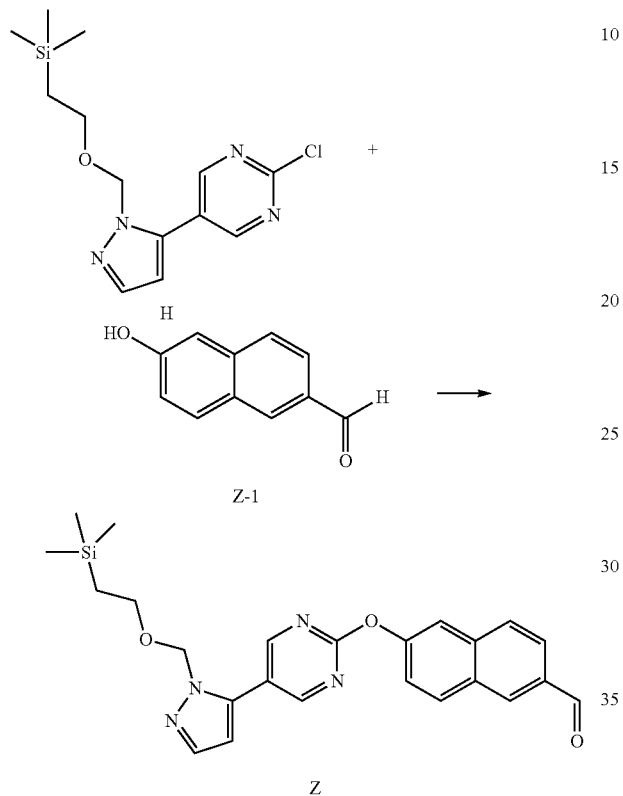

A mixture of H (0.50 g, 1.6 mmol), Z-1 (0.27 g, 1.6 mmol) and K$_2$CO$_3$ (0.33 g, 2.4 mmol) in DMF (6 mL) is stirred at 120° C. for 8 h. The mixture is poured into water and twice extracted with EtOAc. The combined organic extracts are washed with water and brine, dried over Na$_2$SO$_4$, filtered and concentrated. The residue is purified by flash chromatography (0-50% EtOAc/heptane) to give the title product (Z). MS (ES+): m/z 447.4 [M+H]$^+$.

Intermediate AA

Preparation of 2-methoxy-1-piperazin-1-yl-ethanone (AA)

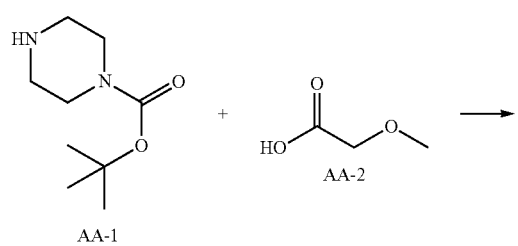

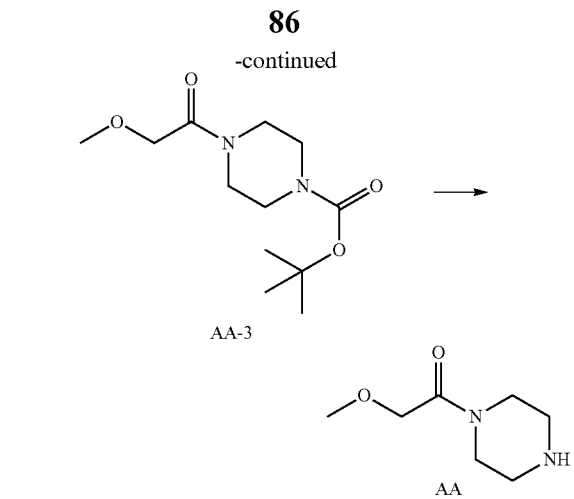

A stirred solution of AA-1 (100 μL, 1.25 mmol) in MeCN (10 mL) is treated with TBTU (400 mg, 1.25 mmol). After 20 minutes, AA-2 (0.190 g, 1.00 mmol) is added, and the mixture is stirred overnight. The reaction is poured into dilute aqueous Na$_2$CO$_3$, and extracted with DCM (3×5 mL). The combined extracts are dried over Na$_2$SO$_4$, filtered and concentrated. The residue is dissolved in DCM and passed through a MP-TSOH cartridge, and concentrated to afford AA-3.

A stirred solution of AA-3 (0.100 g, 0.380 mmol) in 1,4-dioxane (4 mL) is treated with a solution of HCl in 1,4-dioxane (4M, 1 mL). After 72 h, the reaction is concentrated, redissolved in wet MeOH, passed through a PL-HCO$_3$ cartridge, and concentrated to afford the title product (AA).

Intermediate AB

Preparation of (S)-2-Hydroxy-1-piperazin-1-yl-propan-1-one (AB)

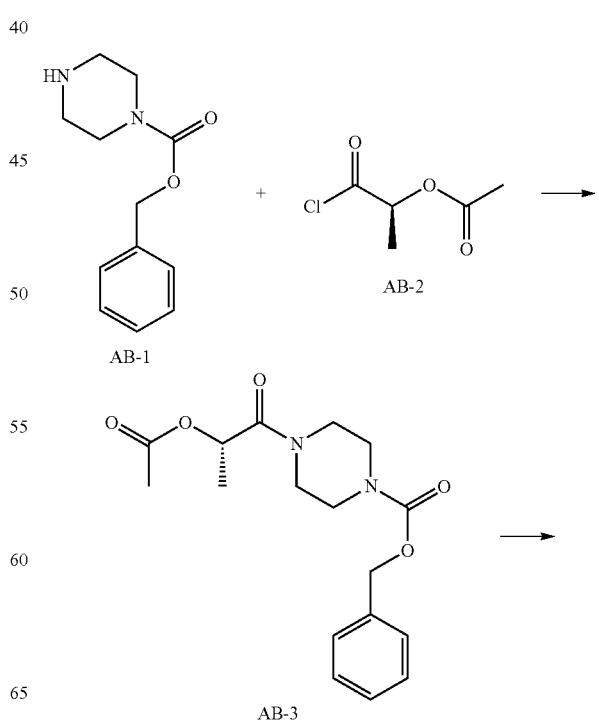

87
-continued

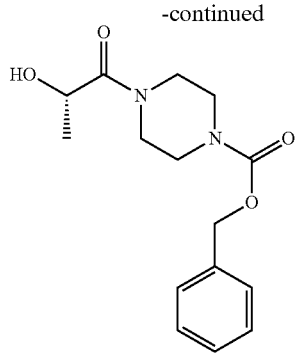

AB-4

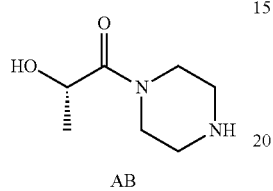

AB

To a solution of AB-1 (1.0 g, 4.5 mmol) and TEA (1.3 mL, 9.1 mmol) in MeCN (25 mL) at 0° C. is added AB-2 (0.7 g, 4.5 mmol). The resultant mixture is warmed to ambient temperature, stirred for 30 min, poured into ice water, and extracted with EtOAc. The organic layer is extracted with saturated aqueous NaHCO$_3$ and brine, dried over Na$_2$SO$_4$, filtered and concentrated to afford AB-3.

To a solution of AB-3 (1.3 g, 3.8 mmol) in a mixture of dioxane (10 mL) and water (10 mL) is added LiOH (0.40 g, 9.7 mmol). The resultant mixture is stirred for 2 h, neutralized with concentrated HCl, and extracted with EtOAc. The organic layer is dried over Na$_2$SO$_4$, filtered and concentrated to give AB-4.

To a solution of AB-4 (1.3 g, 4.4 mmol) in EtOH (25 mL) is added 10% Pd/C (0.3 g). The mixture is stirred for 4 h under an atmosphere of H$_2$, filtered through a pad of diatomaceous earth, and concentrated to give the title product (AB).

The following intermediate is synthesized from the corresponding acyl chloride and intermediate AB-1 according to the procedure described for the synthesis of intermediate AB.

88

Intermediate AD

Preparation of
1-(3-Methylaminomethyl-azetidin-1-yl)-ethanone.HCl
(AD)

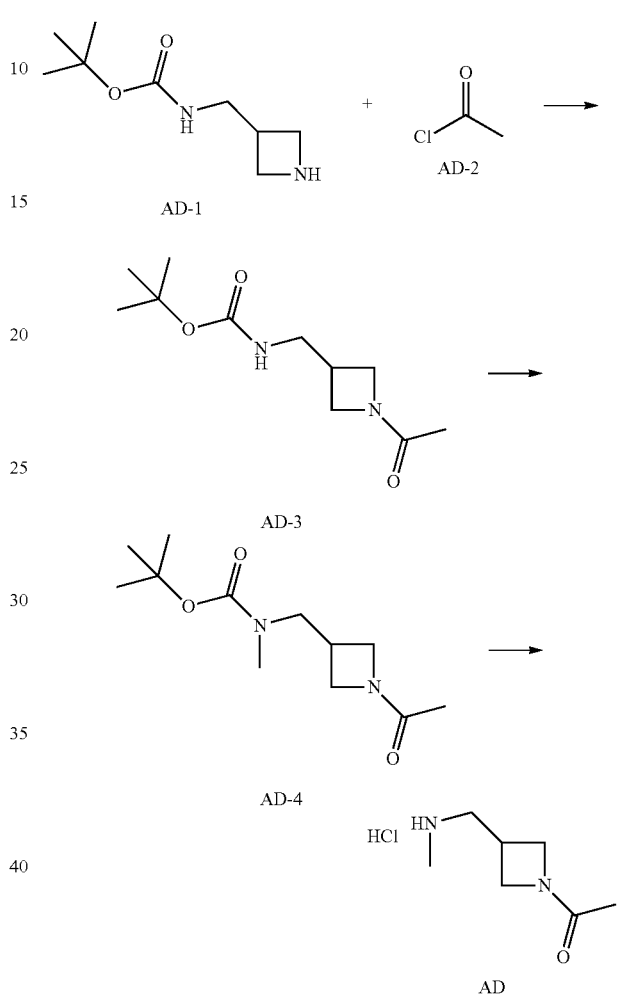

| Intermediate | Structure | Intermediate Name | Acyl Chloride |
|---|---|---|---|
| AC | ![structure] | 2-Hydroxy-2-methyl-1-piperazin-1-yl-propan-1-one | ![acyl chloride] |

To a solution of AD-1 (7.90 g, 40.9 mmol) and TEA (11.5 mL, 82.5 mmol) in DCM (125 mL) at −10° C. is added AD-2 (3.2 mL, 44 mmol). The resultant mixture is warmed to ambient temperature, and stirred for 18 h. The reaction mixture is concentrated, and the residue is dissolved in EtOAc (300 mL). The organic layer is extracted with saturated aqueous NaHCO₃ (200 mL), saturated aqueous NH₄Cl (200 mL), and brine (50 mL), dried over Na₂SO₄, filtered and concentrated to afford AD-3.

To a solution of AD-3 (8.50 g, 36.1 mmol) in THF (100 mL) at 0° C. is added sodium hydride (60% dispersion in oil, 3.00 g, 75.0 mmol), and the resultant mixture is stirred for 1 h at 0° C. Iodomethane (4.6 mL, 75 mmol) is added, and the mixture is stirred at ambient temperature for 24 h. The reaction mixture is cooled to 0° C., quenched with saturated aqueous NH₄Cl (300 mL), and extracted with EtOAc (3×300 mL). The combined organic layers are washed with brine (50 mL), dried over Na₂SO₄, filtered and concentrated. The residue is purified by flash chromatography eluting with 0-5% MeOH in DCM to give AD-4.

A stirred solution of AD-4 (8.23 g, 32.9 mmol) in DCM (200 mL) is treated with a solution of HCl in 1,4-dioxane (4 M, 82.3 mL). After 18 h, the reaction mixture is concentrated. The resultant residue is titurated with ether, and dried in vacuo under P₂O₅ to afford the title product (AD).

Intermediates AE and AF

Preparation of ((R)-6-{5-[2-(2-Trimethylsilanyl-ethoxymethyl)-2H-pyrazol-3-yl]-pyridin-2-yloxy}-2,3-dihydro-benzofuran-2-yl)-methanol (AE), and ((S)-6-{5-[2-(2-Trimethylsilanyl-ethoxymethyl)-2H-pyrazol-3-yl]-pyridin-2-yloxy}-2,3-dihydro-benzofuran-2-yl)-methanol (AF)

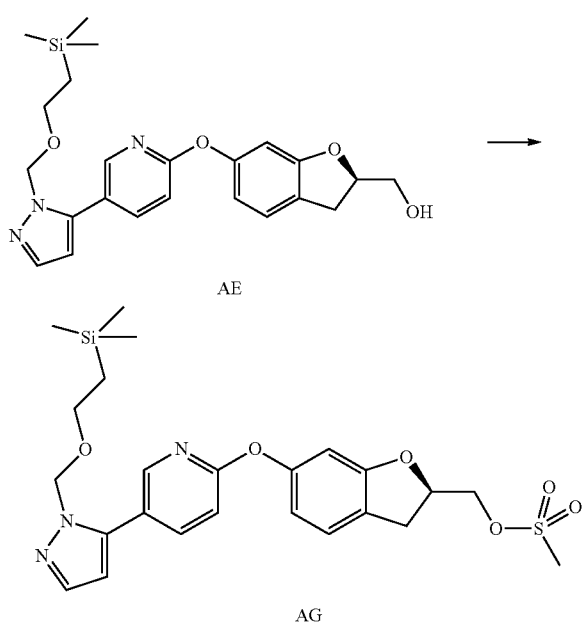

Intermediate F-10 is resolved using Supercritical Fluid Chromatography [column: Regis RegisPack 21.1×25 cm; mobile phase: 10.5 ml/min (1:1:1 MeOH:EtOH:IPA)+75 g/min CO2; temperature: 40° C.] to afford the title product (AE) as the first eluting enantiomer and the title product (AF) as the second eluting enantiomer. The title product (AE) is arbitrarily assigned as the (R)-enantiomer, and the title product (AF) is arbitrarily assigned as the (S)-enantiomer.

Intermediates AG

Preparation of Methanesulfonic acid (R)-6-{5-[2-(2-trimethylsilanyl-ethoxymethyl)-2H-pyrazol-3-yl]-pyridin-2-yloxy}-2,3-dihydro-benzofuran-2-ylm-ethyl ester (AG)

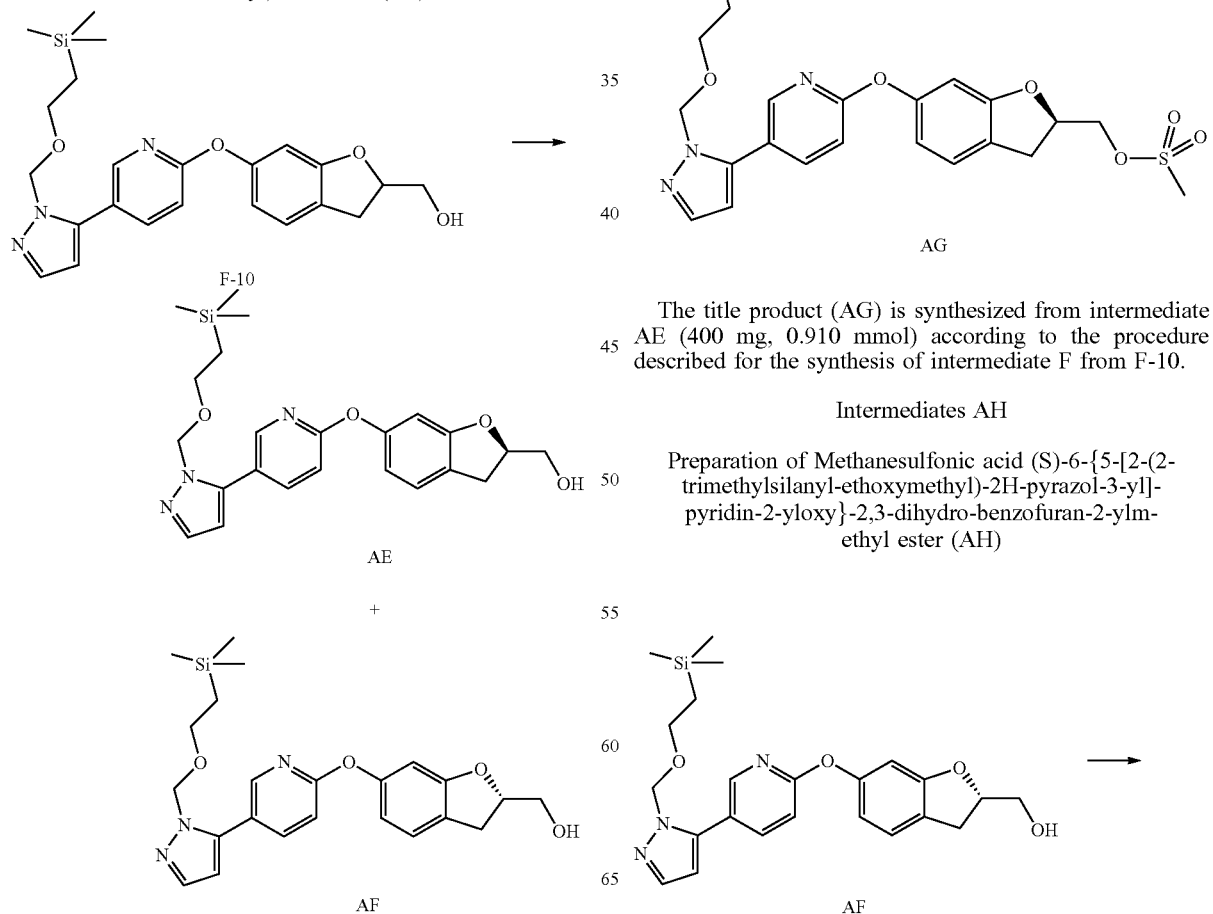

The title product (AG) is synthesized from intermediate AE (400 mg, 0.910 mmol) according to the procedure described for the synthesis of intermediate F from F-10.

Intermediates AH

Preparation of Methanesulfonic acid (S)-6-{5-[2-(2-trimethylsilanyl-ethoxymethyl)-2H-pyrazol-3-yl]-pyridin-2-yloxy}-2,3-dihydro-benzofuran-2-ylm-ethyl ester (AH)

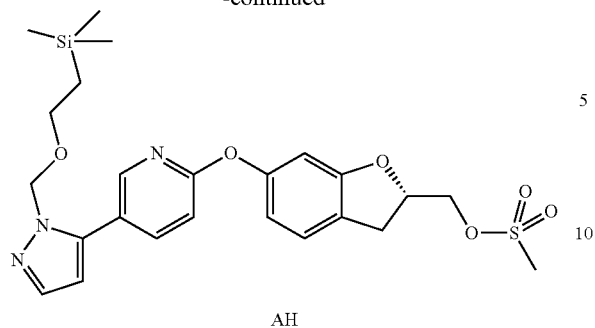

AH

The title product (AH) is synthesized from intermediate AF (400 mg, 0.910 mmol) according to the procedure described for the synthesis of intermediate F from F-10.

Syntheses of Compounds of the Invention

Methods of making the compounds of the invention are described in detail below. Mass spectral and HPLC data for the compounds of the invention are found in Table 2.

Example 1

Preparation of 1-{6-[5-(2H-Pyrazol-3-yl)-pyridin-2-yloxy]-naphthalen-2-ylmethyl}-azetidin-3-ol (1)

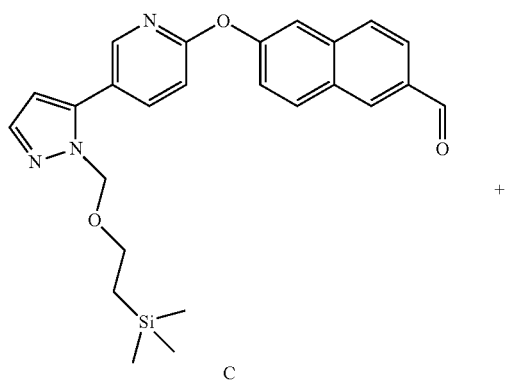

C

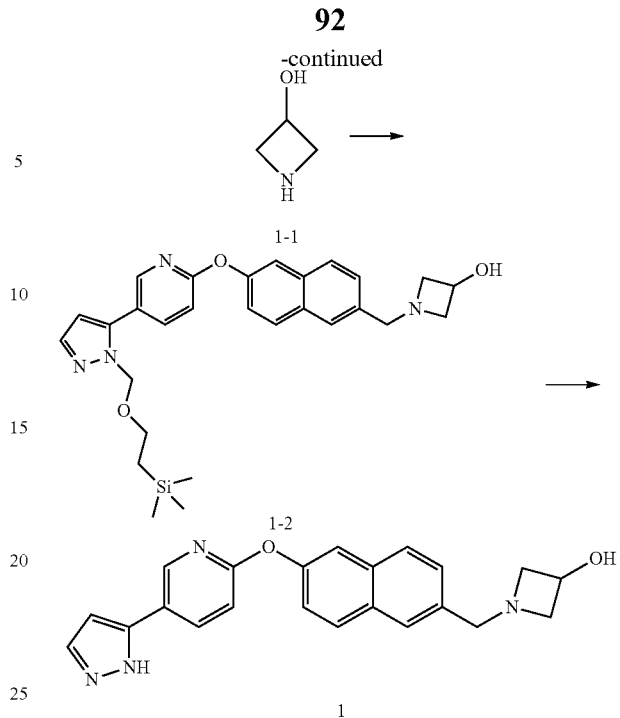

A solution of intermediates C (67.0 mg, 0.150 mmol), 1-1 (32.9 mg, 0.301 mmol) and TEA (43.4 µL, 0.301 mmol) in DCM (1 mL) is treated with sodiumtriacetoxyborohydride (63.7 mg, 0.301 mmol). The resultant mixture is stirred at ambient temperature for 24 h and concentrated. The residue is purified by RP-HPLC eluting with 5-75% MeCN in water (+0.1% TFA) to give intermediate 1-2.

To 1-2 (61 mg, 0.11 mmol) is added a solution of TFA/DCM (2 mL, 1:1). The mixture is stirred for 2 h and concentrated. The residue is purified by RP-HPLC eluting with 0-65% MeCN in water (+0.1% TFA). Fractions containing the desired product are combined and concentrated. The residue is dissolved in DCM and washed with saturated aqueous NaHCO₃. The organic layer is dried over Na₂SO₄, filtered, and concentrated to give the title product (1).

The following examples are synthesized from the appropriate amine reagents and intermediate C according to the procedure described for the synthesis of Example 1.

| Ex. | Compound Name | Amine Reagent |
| --- | --- | --- |
| 2 | 1-{6-[5-(2H-Pyrazol-3-yl)-pyridin-2-yloxy]-naphthalen-2-ylmethyl}-azetidine-3-carboxylic acid amide | |
| 3 | N-(1-{6-[5-(2H-Pyrazol-3-yl)-pyridin-2-yloxy]-naphthalen-2-ylmethyl}-azetidin-3-yl)-acetamide | |
| 4 | (1-{6-[5-(2H-Pyrazol-3-yl)-pyridin-2-yloxy]-naphthalen-2-ylmethyl}-azetidin-3-yl)-methanol | |

| Ex. | Compound Name | Amine Reagent |
|---|---|---|
| 5 | (S)-1-{6-[5-(2H-Pyrazol-3-yl)-pyridin-2-yloxy]-naphthalen-2-ylmethyl}-pyrrolidin-3-ol | |
| 6 | (R)-1-{6-[5-(2H-Pyrazol-3-yl)-pyridin-2-yloxy]-naphthalen-2-ylmethyl}-pyrrolidin-3-ol | |
| 7 | 2-Hydroxy-1-(4-{6-[5-(2H-pyrazol-3-yl)-pyridin-2-yloxy]-naphthalen-2-ylmethyl}-piperazin-1-yl)-ethanone | |

Example 8

Preparation of (S)-3-Hydroxy-1-(1-{6-[5-(2H-pyrazol-3-yl)-pyridin-2-yloxy]-quinolin-2-ylmethyl}-piperidin-4-yl)-pyrrolidin-2-one (8)

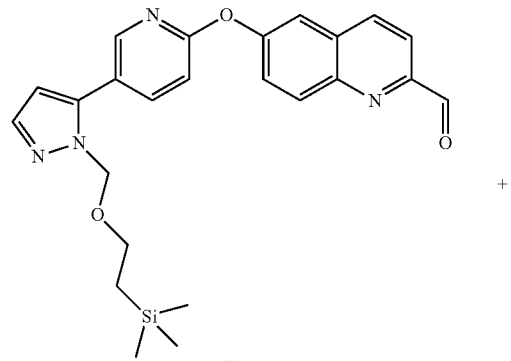

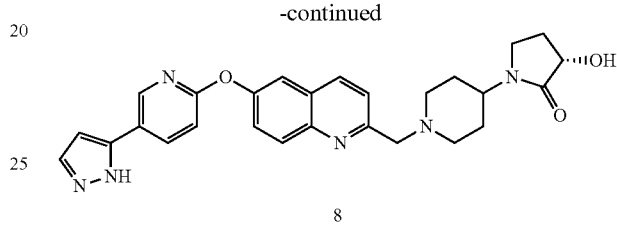

Intermediate 8-2 is synthesized from intermediates D (100 mg, 0.224 mmol) and 8-1 (57.7 mg, 0.313 mmol) according to the procedure described in Example 1 for the synthesis of intermediate 1-2.

The title product 8 is synthesized from intermediates 8-2 (113 mg, 0.171 mmol) according to the procedure described in Example 1 for the synthesis of compound 1 from 1-2.

Example 10

Preparation of 2-{6-[5-(2H-Pyrazol-3-yl)-pyridin-2-yloxy]-naphthalen-2-ylmethyl}-2-aza-spiro[3.3]heptan-6-ol (10)

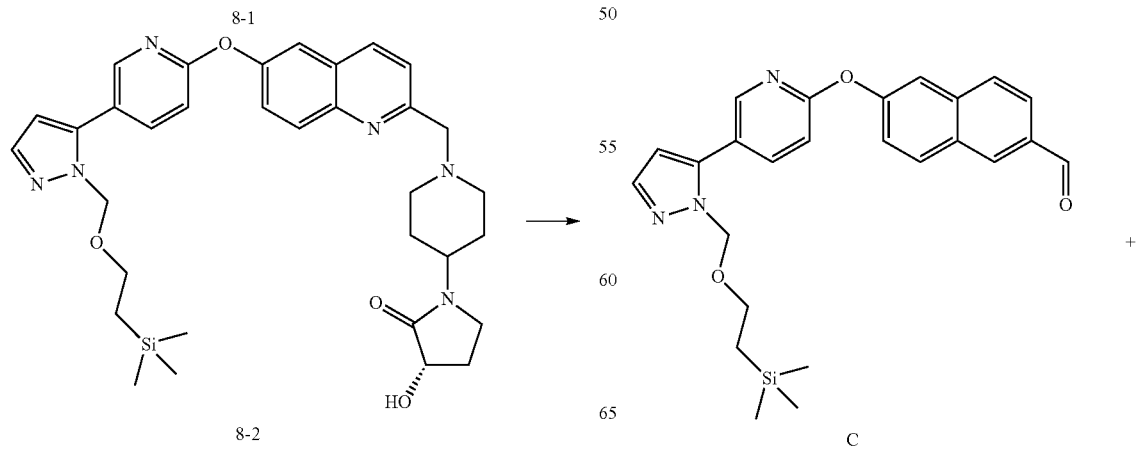

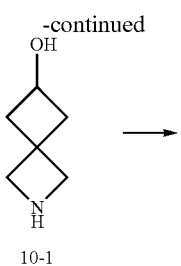
10-1

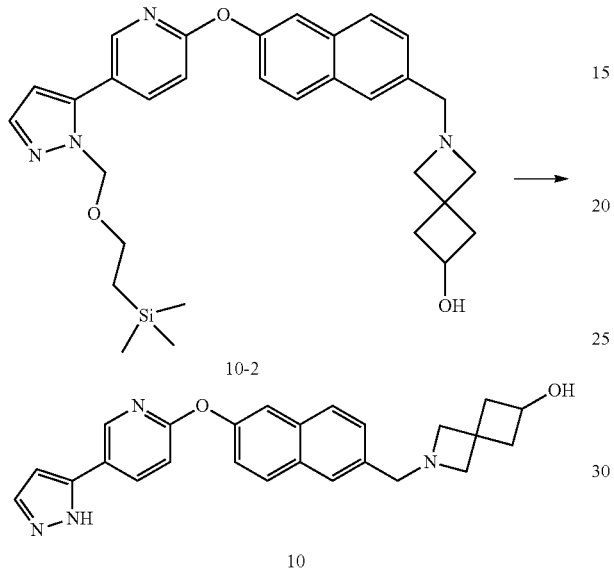
10-2
10

A solution of intermediates C (100.0 mg, 0.224 mmol), 10-1 (101.9 mg, 0.449 mmol) and TEA (64.7 μL, 0.449 mmol) in DCM (2 mL) is treated with sodiumtriacetoxyborohydride (95.1 mg, 0.449 mmol). The resultant mixture is stirred at ambient temperature for 24 h and concentrated. The residue containing 10-2 is used in the next step without purification.

To a crude mixture of 10-2 (117.0 mg) is added a solution of TFA/DCM (2 mL, 1:1). The mixture is stirred for 2 h and concentrated. The residue is purified by RP-HPLC eluting with 0-50% MeCN in water (+0.1% TFA). Fractions containing the desired product are combined and concentrated. The residue is dissolved in DCM and washed with saturated aqueous NaHCO$_3$. The organic layer is dried over Na$_2$SO$_4$, filtered, concentrated to give the title product (10).

The following examples are synthesized from the appropriate amine reagents and intermediate C according to the procedure described for the synthesis of Example 10.

| Ex. | Compound Name | Amine Reagent |
|---|---|---|
| 11 | 3-Methyl-1-{6-[5-(2H-pyrazol-3-yl)-pyridin-2-yloxy]-naphthalen-2-ylmethyl}-azetidin-3-ol | |
| 12 | N-((R)-1-{6-[5-(2H-Pyrazol-3-yl)-pyridin-2-yloxy]-naphthalen-2-ylmethyl}-pyrrolidin-3-yl)-acetamide | |
| 13 | N-((S)-1-6-[5-(2H-Pyrazol-3-yl)-pyridin-2-yloxy]-naphthalen-2-ylmethyl}-pyrrolidin-3-yl)-acetamide | |
| 14 | (S)-1-{6-[5-(2H-Pyrazol-3-yl)-pyridin-2-yloxy]-naphthalen-2-ylmethyl}-piperidin-3-ol | |
| 15 | (R)-1-{6-[5-(2H-Pyrazol-3-yl)-pyridin-2-yloxy]-naphthalen-2-ylmethyl}-piperidin-3-ol | |

| Ex. | Compound Name | Amine Reagent |
|---|---|---|
| 16 | 2-(Methyl-{6-[5-(2H-pyrazol-3-yl)-pyridin-2-yloxy]-naphthalen-2-ylmethyl}-amino)-ethanol | |
| 17 | (1-{6-[5-(2H-Pyrazol-3-yl)-pyridin-2-yloxy]-naphthalen-2-ylmethyl}-piperidin-4-yl)-methanol | |
| 18 | ((S)-1-{6-[5-(2H-Pyrazol-3-yl)-pyridin-2-yloxy]-naphthalen-2-ylmethyl}-pyrrolidin-3-yl)-methanol | |
| 22 | ((R)-1-{6-[5-(2H-Pyrazol-3-yl)-pyridin-2-yloxy]-naphthalen-2-ylmethyl}-pyrrolidin-3-yl)-methanol | |

Example 19

Preparation of 2-Hydroxy-1-[(R)-3-(methyl-{6-[5-(2H-pyrazol-3-yl)-pyridin-2-yloxy]-naphthalen-2-ylmethyl}-amino)-pyrrolidin-1-yl]-ethanone (19)

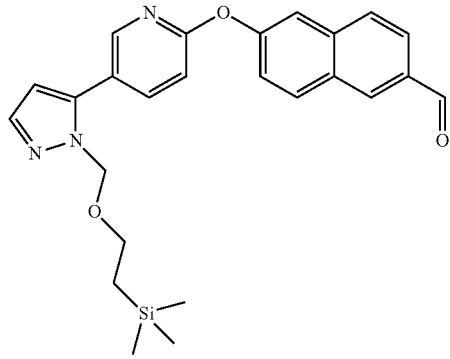

C

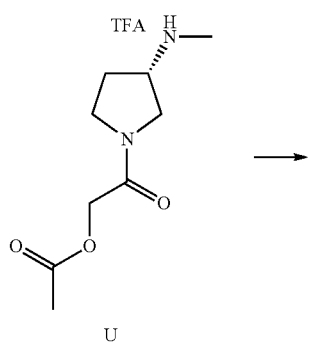

U

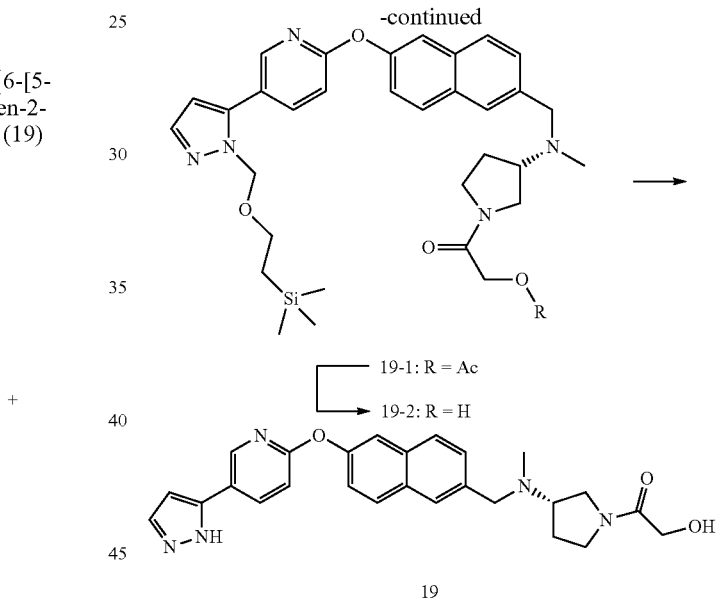

Intermediate 19-1 is synthesized from intermediates C (150 mg, 0.337 mmol) and U (135 mg, 0.673 mmol) according to the procedure described in Example 1 for the synthesis of intermediate 1-2.

To a solution of 19-1 (160 mg, 0.254 mmol) in a mixture of dioxane (2 mL) and water (1 mL) is added LiOH.H$_2$O (21.3 mg, 0.508 mmol). The mixture is stirred at ambient temperature for 1 h, neutralized with concentrated HCl, and diluted with DCM and water. The organic layer is dried over anhydrous Na$_2$SO$_4$, filtered and concentrated. The resultant crude mixture of 19-2 is treated with a solution of TFA/DCM (2 mL, 1:1). The mixture is stirred at ambient temperature for 2 h and concentrated. The residue is purified by RP-HPLC eluting with 0-50% MeCN in water (+0.1% TFA). Fractions containing the desired product are combined and concentrated. The residue is dissolved in DCM and washed with saturated aqueous NaHCO$_3$. The organic layer is dried over Na$_2$SO$_4$, filtered, and concentrated to give the title product (19).

The following examples are synthesized from the appropriate amine reagents and intermediate C according to the procedure described for the synthesis of Example 19.

| Ex. | Compound Name | Amine Reagent |
|---|---|---|
| 9 | 2-Hydroxy-N-(1-{6-[5-(2H-pyrazol-3-yl)-pyridin-2-yloxy]-naphthalen-2-ylmethyl}-piperidin-4-yl)-acetamide | |
| 20 | 2-Hydroxy-N-methyl-N-((S)-1-{6-[5-(2H-pyrazol-3-yl)-pyridin-2-yloxy]-naphthalen-2-ylmethyl}-pyrrolidin-3-yl)-acetamide | |
| 21 | 2-Hydroxy-N-methyl-N-((R)-1-{6-[5-(2H-pyrazol-3-yl)-pyridin-2-yloxy]-naphthalen-2-ylmethyl}-pyrrolidin-3-yl)-acetamide | |
| 23 | 2-Hydroxy-1-[(S)-3-(methyl-{6-[5-(2H-pyrazol-3-yl)-pyridin-2-yloxy]-naphthalen-2-ylmethyl}-amino)-pyrrolidin-1-yl]-ethanone | |

Example 24

Preparation of 2-Methoxy-1-(4-{6-[5-(2H-pyrazol-3-yl)-pyrimidin-2-yloxy]-naphthalen-2-ylmethyl}-piperazin-1-yl)-ethanone (24)

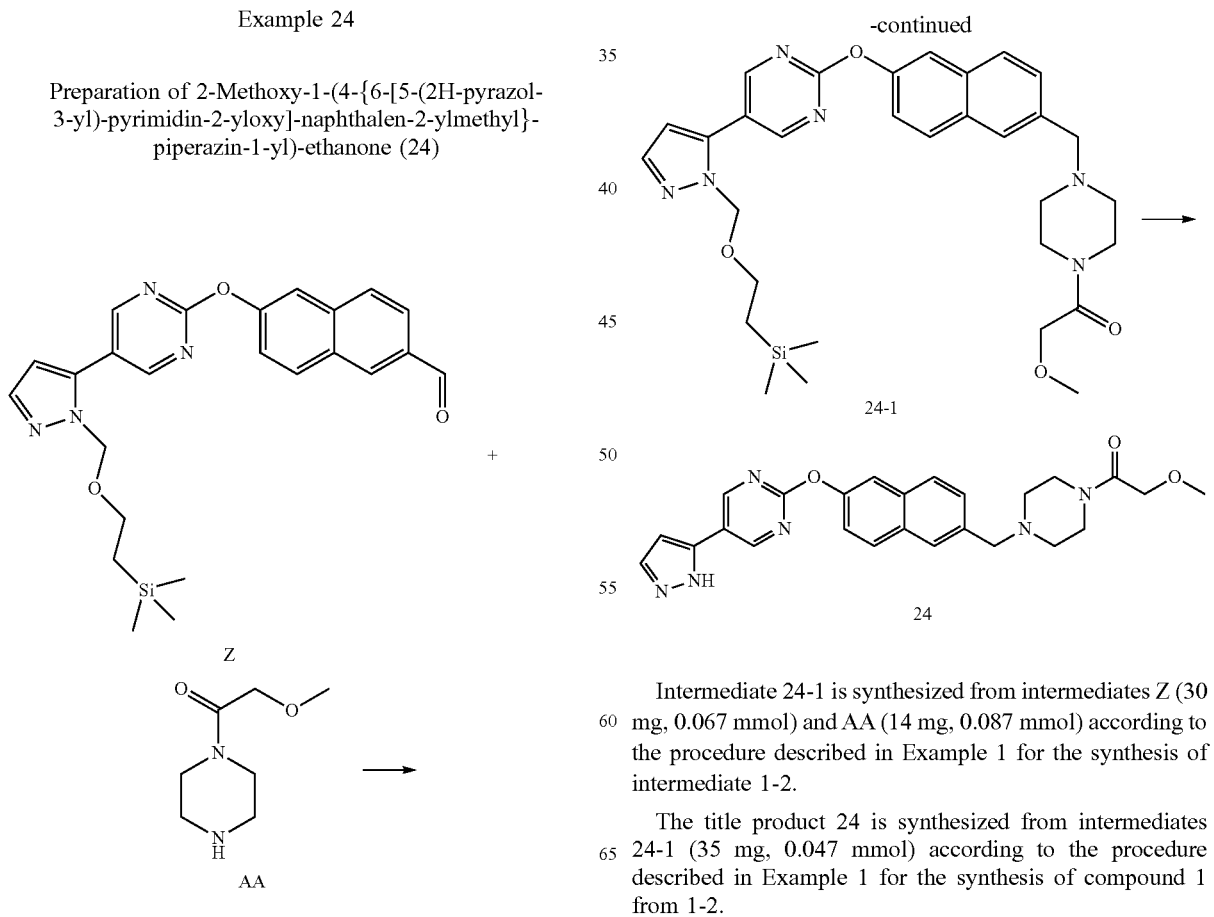

Intermediate 24-1 is synthesized from intermediates Z (30 mg, 0.067 mmol) and AA (14 mg, 0.087 mmol) according to the procedure described in Example 1 for the synthesis of intermediate 1-2.

The title product 24 is synthesized from intermediates 24-1 (35 mg, 0.047 mmol) according to the procedure described in Example 1 for the synthesis of compound 1 from 1-2.

The following examples are synthesized from the appropriate amine reagents and intermediate Z according to the procedure described for the synthesis of Example 1.

| Ex. | Compound Name | Amine Reagent |
|---|---|---|
| 25 | 1-(4-{6-[5-(2H-Pyrazol-3-yl)-pyrimidin-2-yloxy]-naphthalen-2-ylmethyl}-piperazin-1-yl)-ethanone | |
| 26 | 1-{6-[5-(2H-Pyrazol-3-yl)-pyrimidin-2-yloxy]-naphthalen-2-ylmethyl}-piperidin-4-ol | |
| 27 | 1-{6-[5-(2H-Pyrazol-3-yl)-pyrimidin-2-yloxy]-naphthalen-2-ylmethyl}-piperidine-4-carboxylic acid amide | |
| 28 | N-(1-{6-[5-(2H-Pyrazol-3-yl)-pyrimidin-2-yloxy]-naphthalen-2-ylmethyl}-piperidin-4-yl)-acetamide | |
| 29 | (S)-3-Hydroxy-1-(1-{6-[5-(2H-pyrazol-3-yl)-pyrimidin-2-yloxy]-naphthalen-2-ylmethyl}-piperidin-4-yl)-pyrrolidin-2-one | |
| 31 | 2-Hydroxy-N-methyl-N-(1-{6-[5-(2H-pyrazol-3-yl)-pyrimidin-2-yloxy]-naphthalen-2-ylmethyl}-piperidin-4-yl)-acetamide | |

The following examples are synthesized from the appropriate amine reagents and intermediate Z according to the procedure described for the synthesis of Example 10.

| Ex. | Compound Name | Amine Reagent |
|---|---|---|
| 30 | (S)-2-Hydroxy-1-(4-{6-[5-(2H-pyrazol-3-yl)-pyrimidin-2-yloxy]-naphthalen-2-ylmethyl}-piperazin-1-yl)-propan-1-one | |
| 32 | 1-{3-[(Methyl-{6-[5-(2H-pyrazol-3-yl)-pyrimidin-2-yloxy]-naphthalen-2-ylmethyl}-amino)-methyl]-azetidin-1-yl}-ethanone | |
| 33 | 3-(1-{6-[5-(2H-Pyrazol-3-yl)-pyrimidin-2-yloxy]-naphthalen-2-ylmethyl}-piperidin-4-yl)-oxazolidin-2-one | |
| 34 | 4-{6-[5-(2H-Pyrazol-3-yl)-pyrimidin-2-yloxy]-naphthalen-2-ylmethyl}-piperazine-1-carboxylic acid dimethylamide | |
| 35 | 2,2-Dimethyl-1-(4-{6-[5-(2H-pyrazol-3-yl)-pyrimidin-2-yloxy]-naphthalen-2-ylmethyl}-piperazin-1-yl)-propan-1-one | |
| 36 | 1-(1-{6-[5-(2H-Pyrazol-3-yl)-pyrimidin-2-yloxy]-naphthalen-2-ylmethyl}-piperidin-4-yl)-pyrrolidin-2-one | |
| 37 | 1-(4-{6-[5-(2H-Pyrazol-3-yl)-pyrimidin-2-yloxy]-naphthalen-2-ylmethyl}-piperazin-1-yl)-propan-1-one | |
| 38 | 1-{6-[5-(2H-Pyrazol-3-yl)-pyrimidin-2-yloxy]-naphthalen-2-ylmethyl}-piperidine-4-carboxylic acid dimethylamide | |

103

-continued

| Ex. | Compound Name | Amine Reagent |
|---|---|---|
| 39 | 2-Hydroxy-2-methyl-1-(4-{6-[5-(2H-pyrazol-3-yl)-pyrimidin-2-yloxy]-naphthalen-2-ylmethyl}-piperazin-1-yl)-propan-1-one | |
| 40 | Cyclopropyl-(4-{6-[5-(2H-pyrazol-3-yl)-pyrimidin-2-yloxy]-naphthalen-2-ylmethyl}-piperazin-1-yl)-methanone | |
| 41 | 2-Methyl-1-(4-{6-[5-(2H-pyrazol-3-yl)-pyrimidin-2-yloxy]-naphthalen-2-ylmethyl}-piperazin-1-yl)-propan-1-one | |

Example 42

Preparation of 1-{6-[5-(2H-Pyrazol-3-yl)-pyridin-2-yloxy]-quinolin-2-ylmethyl}-azetidin-3-ol (42)

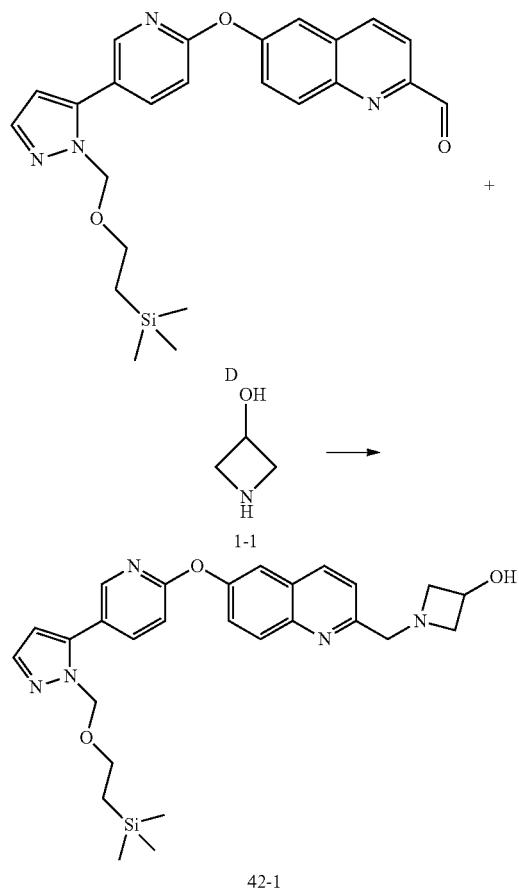

42-1

104

-continued

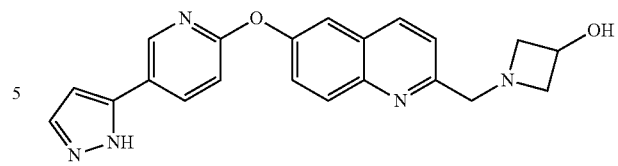

42

To a solution of intermediate D (300 mg, 0.672 mmol) in DCM (1 mL) is added 1-1 (88.0 mg, 0.803 mmol) and TEA (117 μL, 0.810 mmol). The mixture is stirred for 30 min, and treated with sodiumtriacetoxyborohydride (285 mg, 1.34 mmol). The resultant mixture is stirred at ambient temperature for 18 h, quenched with MeOH, stirred for 1 h, and concentrated. The residue is dissolved in EtOAc (50 mL), and extracted with saturated aqueous NaHCO$_3$ (50 mL). The organic layer is dried over Na$_2$SO$_4$, filtered and concentrated. The residue is purified on SiO$_2$ eluting with 0-5% MeOH in DCM to give the intermediate 42-1.

To a solution of 42-1 (94.0 mg, 0.187 mmol) in DCM (2 mL) is added TFA (1 mL). The mixture is stirred for 2 h and concentrated. The residue is dissolved in EtOAc (25 mL), and extracted with saturated aqueous NaHCO$_3$ (25 mL). The organic layer is dried over Na$_2$SO$_4$, filtered and concentrated. The residue is purified on SiO$_2$ eluting with 0-5% MeOH (+2% NH$_4$OH) in DCM to give the title compound (42).

Example 43

Preparation of 3-({6-[5-(2H-pyrazol-3-yl)-pyridin-2-yloxy]-quinolin-2-ylmethyl}-amino)-propionitrile (43)

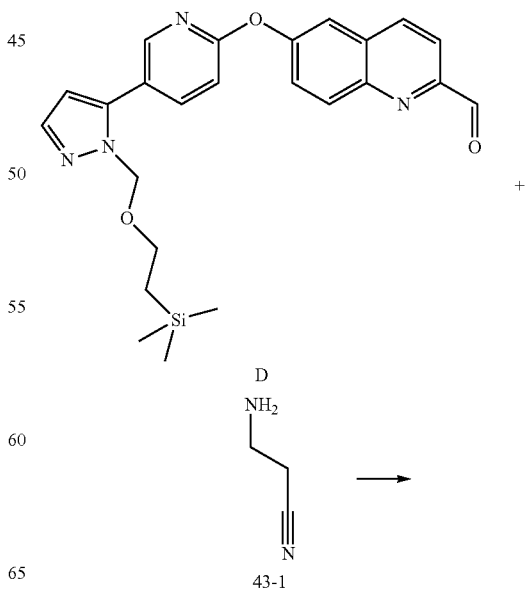

43-1

Example 45

Preparation of (R)-1-{6-[5-(2H-pyrazol-3-yl)-pyrimidin-2-yloxy]-naphthalen-2-ylmethyl}-pyrrolidin-3-ol (45)

To a mixture of D (100 mg, 0.224 mmol), 43-1 (35 mg, 0.50 mmol) and sodium triacetoxyborohydride (50.5 mg, 0.796 mmol) in MeOH (5.0 mL) is added acetic acid (2 drops). The mixture is stirred at 50° C. for 16 h, cooled to ambient temperature, concentrated, diluted with EtOAc (25 mL), and extracted with H₂O (2×25 mL). The combined organic layers are dried over Na₂SO₄, filtered and concentrated. The residue is purified on SiO₂ (0-10% MeOH in DCM) to give 43-2.

A solution of 43-2 (84.0 mg, 0.168 mmol) in HCl in dioxane (4 M, 25 mL) is stirred at ambient temperature overnight. The reaction mixture is concentrated, and the resultant residue is purified on SiO₂ eluting with 0-10% MeOH (+1% NH₄OH) in DCM to give the title compound (43).

The following example is synthesized from D and the appropriate amine reagent according to the procedure described for the synthesis of Example 43.

| Ex. | Compound Name | Amine Reagent |
|---|---|---|
| 44 | (R)-3-({6-[5-(2H-Pyrazol-3-yl)-pyridin-2-yloxy]-quinolin-2-ylmethyl}-amino)-pentanenitrile | H₂N-CH(CH₂CH₃)-CH₂-C≡N |

A solution of Z (50.0 mg, 0.112 mmol) and 45-1 (12.0 mg, 0.138 mmol) in dry DCM (5.0 mL) is stirred for 10 minutes. Sodium triacetoxyborohydride (35.0 mg, 0.165 mmol) is added, and the resultant mixture is stirred at ambient temperature for 16 h. Additional amounts of 45-1 (12.0 mg, 0.138 mmol) and sodium triacetoxyborohydride (35.0 mg, 0.165 mmol) are added, and the reaction mixture is stirred for an additional 16 h. The mixture is diluted with DCM (25 mL), and extracted with H₂O (25 mL). The organic layer is dried over Na₂SO₄, filtered and concentrated. The residue is purified on SiO₂ (0-10% MeOH in DCM) to give 45-2.

To a solution of 45-2 (58 mg, 0.11 mmol) in DCM (2.0 mL) is added TFA (2.0 mL). The mixture is stirred at ambient temperature for 16 h, and concentrated. The residue is dissolved in DCM (25 mL), and extracted with saturated aqueous NaHCO₃ (25 mL). The organic layer is dried over Na₂SO₄, filtered and concentrated. The residue is purified on SiO₂ eluting with 0-10% MeOH (+1% NH₄OH) in DCM to give the title compound (45).

The following examples are synthesized from intermediate Z and the appropriate amine reagent according to the procedure described for the synthesis of Example 45.

| Ex. | Compound Name | Amine Reagent |
|---|---|---|
| 46 | (S)-1-16-[5-(2H-Pyrazol-3-yl)-pyrimidin-2-yloxy]-naphthalen-2-ylmethyl}-pyrrolidin-3-ol | |
| 47 | 3-Methyl-1-16-[5-(2H-pyrazol-3-yl)-pyrimidin-2-yloxy]-naphthalen-2-ylmethyl}-azetidin-3-ol | |
| 48 | 2-Hydroxy-1-(4-16-[5-(2H-pyrazol-3-yl)-pyrimidin-2-yloxy]-naphthalen-2-ylmethyl}-piperazin-1-yl)-ethanone | |
| 49 | 1-{6-[5-(2H-Pyrazol-3-yl)-pyrimidin-2-yloxy]-naphthalen-2-ylmethyl}-azetidin-3-ol | |

Example 50

Preparation of 3-Oxo-3-(8-{6-[5-(2H-pyrazol-3-yl)-pyridin-2-yloxy]-quinolin-2-ylmethyl}-3,8-diaza-bicyclo[3.2.1]oct-3-yl)-propionitrile (50)

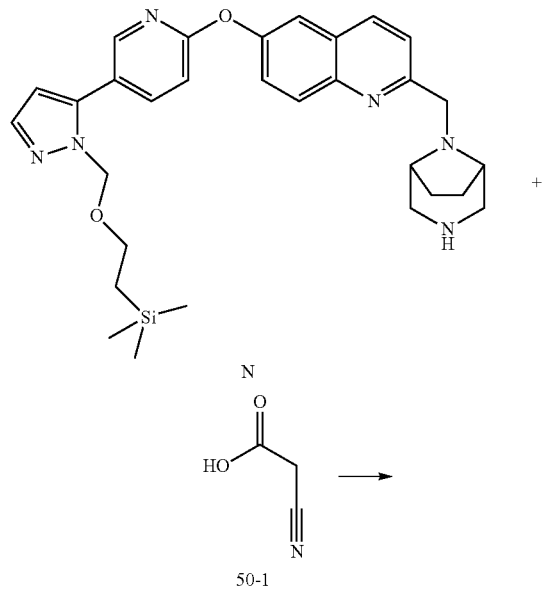

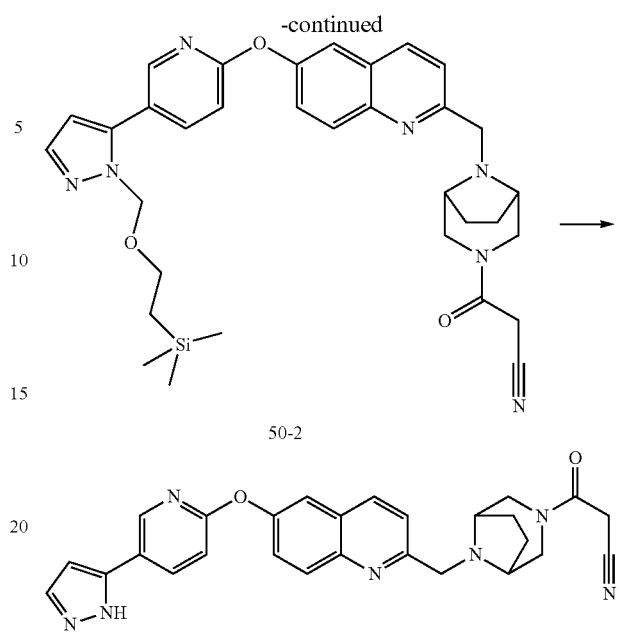

To a solution of N (100 mg, 0.184 mmol) in DMF (1 mL) is added 50-1 (17.2 mg, 0.203 mmol), DIPEA (39.4 µL, 0.221 mmol), and TBTU (65.0 mg, 0.203 mmol). After 13 h, the mixture is concentrated to give a crude, which is purified on RP-HPLC (C18 column, Solvents=MeCN+0.1% TFA:H2O+0.1% TFA; Gradient=10:90 to 100:0 over 20 min; Flow rate=30 mL/min) to give 50-2.

To 50-2 (118 mg, 0.163 mmol) in DCM (1 mL) is added TFA (0.3 mL). The mixture is stirred at ambient temperature for 3 h, concentrated, and purified on RP-HPLC (C18 column, Solvents=MeCN+0.1% TFA:H2O+0.1% TFA; Gradient=5:95 to 95:5 over 20 min; Flow rate=30 mL/min). The desired fractions are pooled and lyophilized. The residue is dissolved in MeOH, passed through a PL-HCO3 cartridge, and concentrated to give the title product (50).

The following examples are synthesized using the listed intermediates and acid reagents according to the procedure described for the synthesis of Example 50.

| Ex. | Compound Name | Intermediate | Acid Reagent |
|---|---|---|---|
| 51 | 2,2-Dimethyl-3-oxo-3-(8-{6-[5-(2H-pyrazol-3-yl)-pyridin-2-yloxy]-quinolin-2-ylmethyl}-3,8-diaza-bicyclo[3.2.1]oct-3-yl)-propionitrile | N | |
| 52 | (R)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one | N | |
| 53 | (S)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one | N | |

US 9,573,957 B2

109
-continued

| Ex. | Compound Name | Intermediate | Acid Reagent |
|---|---|---|---|
| 54 | (8-{6-[5-(2H-Pyrazol-3-yl)-pyridin-2-yloxy]-quinolin-2-ylmethyl}-3,8-diaza-bicyclo[3.2.1]oct-3-yl)-(R)-tetrahydro-furan-2-yl-methanone | N | |
| 55 | (8-{6-[5-(2H-Pyrazol-3-yl)-pyridin-2-yloxy]-quinolin-2-ylmethyl}-3,8-diaza-bicyclo[3.2.1]oct-3-yl)-(S)-tetrahydro-furan-2-yl-methanone | N | |
| 56 | (1-Hydroxy-cyclopropyl)-(8-{6-[5-(2H-pyrazol-3-yl)-pyridin-2-yloxy]-quinolin-2-ylmethyl}-3,8-diaza-bicyclo[3.2.1]oct-3-yl)-methanone | N | |
| 75 | (S)-2-Methoxy-1-[4-(2-{6-[5-(2H-pyrazol-3-yl)-pyridin-2-yloxy]-benzofuran-3-yl}-ethyl)-piperazin-1-yl]-propan-1-one | Q | |
| 76 | (R)-2-Methoxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one | P | |
| 78 | (R)-2-Methoxy-1-[4-(2-{6-[5-(2H-pyrazol-3-yl)-pyridin-2-yloxy]-benzofuran-3-yl}-ethyl)-piperazin-1-yl]-propan-1-one | Q | |
| 79 | (S)-2-Methoxy-1-(4-{6-[4-(2H-pyrazol-3-yl)-phenoxy]-imidazo[1,2-a]pyridin-2-ylmethyl}-piperazin-1-yl)-propan-1-one | R | |
| 80 | (R)-2-Methoxy-1-(4-{6-[4-(2H-pyrazol-3-yl)-phenoxy]-imidazo[1,2-a]pyridin-2-ylmethyl}-piperazin-1-yl)-propan-1-one | R | |
| 88 | (S)-2-Methoxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one | P | |
| 90 | (1-Hydroxy-cyclopropyl)-[4-(2-{6-[5-(2H-pyrazol-3-yl)-pyridin-2-yloxy]-2,3-dihydro-benzofuran-3-yl}-ethyl)-piperazin-1-yl]-methanone | P | |
| 93 | (1-Hydroxy-cyclopropyl)-[4-(2-{6-[5-(2H-pyrazol-3-yl)-pyridin-2-yloxy]-benzofuran-3-yl}-ethyl)-piperazin-1-yl]-methanone | Q | |

110
-continued

| Ex. | Compound Name | Intermediate | Acid Reagent |
|---|---|---|---|
| 96 | (1-Hydroxy-cyclopropyl)-(4-{6-[4-(2H-pyrazol-3-yl)-phenoxy]-imidazo[1,2-a]pyridin-2-ylmethyl}-piperazin-1-yl)-methanone | R | |

Example 57

Preparation of (S)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one (57)

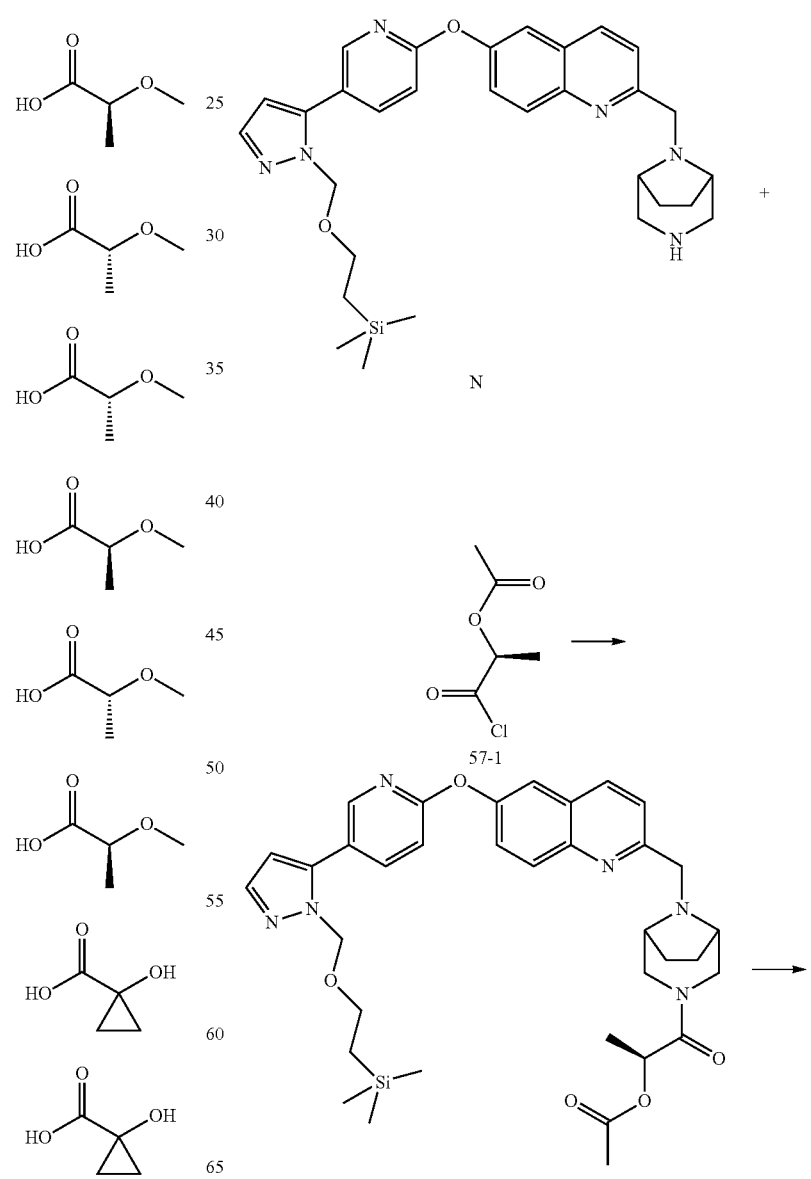

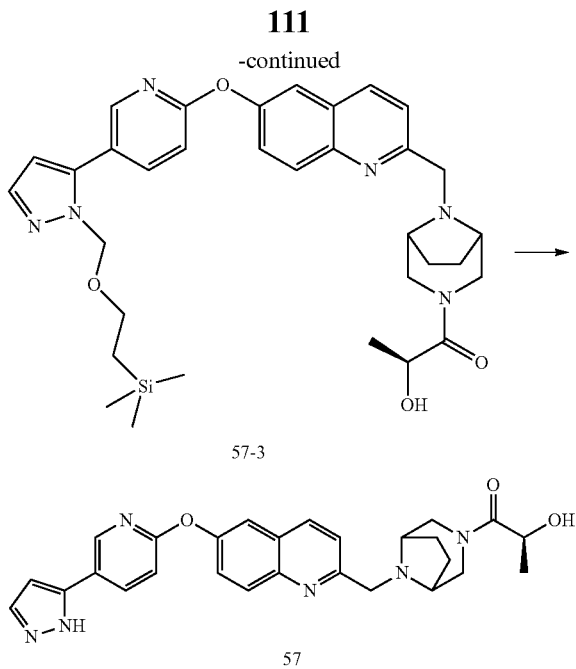

57-3

57

To a solution of N (100 mg, 0.184 mmol) in DMF (1 mL) is added 57-1 (35.0 μL, 0.276 mmol) followed by DIPEA (98.4 μL, 0.553 mmol) at ambient temperature. After 13 h, the crude reaction mixture is purified on RP-HPLC (C18 column, Solvents=MeCN+0.1% TFA:H2O+0.1% TFA; Gradient=5:95 to 95:5 over 20 min; Flow rate=30 mL/min). The desired fractions are pooled and lyophilized. The residue is dissolved in MeOH, passed through a PL-HCO3 cartridge, and concentrated to give 57-2.

To a solution of 57-2 (105.8 mg, 0.161 mmol) in Methanol (5 mL) is added a solution of NaOMe in MeOH (0.5 M, 322 μL, 0.161 mmol). The reaction is stirred for 18 h, neutralized with AcOH, and concentrated to give 57-3, which is dissolved in DCM (1 mL) and treated with TFA (300 μL). The resultant mixture is stirred at ambient temperature for 3 h, concentrated, and purified on RP-HPLC (C18 column, Solvents=MeCN+0.1% TFA:H2O+0.1% TFA; Gradient=5:95 to 95:5 over 20 min; Flow rate=30 mL/min). The desired fractions are pooled and lyophilized. The residue is dissolved in MeOH, passed through a PL-HCO3 cartridge, and concentrated to give the title product (57).

The following examples are synthesized using the listed intermediates and acid chloride reagents according to the procedure described for the synthesis of Example 57.

| Ex. | Compound Name | Intermediate | Acid Chloride Reagent |
|---|---|---|---|
| 58 | 2-Hydroxy-2-methyl-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one | N | ClC(O)C(CH3)2OAc |
| 65 | 2-Hydroxy-1-(4-{6-[5-(2H-pyrazol-3-yl)-pyridin-2-yloxy]-2,3-dihydro-benzofuran-2-ylmethyl}-piperazin-1-yl)-ethanone | O | ClCH2C(O)OAc |
| 81 | 2-Hydroxy-2-methyl-1-[4-(2-{6-[5-(2H-pyrazol-3-yl)-pyridin-2-yloxy]-2,3-dihydro-benzofuran-3-yl}-ethyl)-piperazin-1-yl]-propan-1-one | P | ClC(O)C(CH3)2OAc |
| 82 | 2-Hydroxy-1-[4-(2-{6-[5-(2H-pyrazol-3-yl)-pyridin-2-yloxy]-benzofuran-3-yl}-ethyl)-piperazin-1-yl]-ethanone | Q | ClCH2C(O)OAc |
| 83 | (S)-2-Hydroxy-1-[4-(2-{6-[5-(2H-pyrazol-3-yl)-pyridin-2-yloxy]-benzofuran-3-yl}-ethyl)-piperazin-1-yl]-propan-1-one | Q | ClCH(CH3)C(O)OAc (S) |
| 84 | (S)-2-Hydroxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one | P | ClCH(CH3)C(O)OAc (S) |
| 85 | 2-Hydroxy-2-methyl-1-[4-(2-{6-[5-(2H-pyrazol-3-yl)-pyridin-2-yloxy]-benzofuran-3-yl}-ethyl)-piperazin-1-yl]-propan-1-one | Q | ClC(O)C(CH3)2OAc |
| 86 | 2-Hydroxy-1-(4-{6-[4-(2H-pyrazol-3-yl)-phenoxy]-imidazo[1,2-a]pyridin-2-ylmethyl}-piperazin-1-yl)-ethanone | R | ClCH2C(O)OAc |
| 87 | (S)-2-Hydroxy-1-(4-{6-[4-(2H-pyrazol-3-yl)-phenoxy]-imidazo[1,2-a]pyridin-2-ylmethyl}-piperazin-1-yl)-propan-1-one | R | ClCH(CH3)C(O)OAc (S) |

Example 59

Preparation of (R)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one (59)

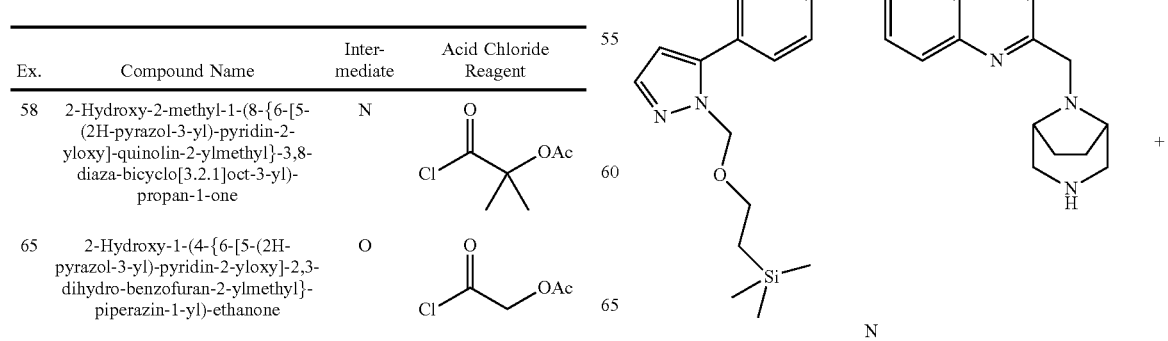

N

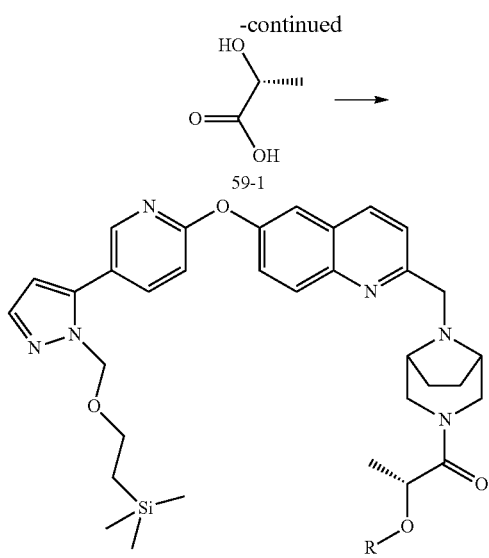

HPLC (C18 column, Solvents=MeCN+0.1% TFA:H2O+ 0.1% TFA; Gradient=5:95 to 95:5 over 20 min; Flow rate=30 mL/min). The desired fractions are pooled and lyophilized. The residue is dissolved in MeOH, passed through a PL-HCO3 cartridge, and concentrated to give the title product (59).

The following examples are synthesized using the listed intermediates and 59-1 according to the procedure described for the synthesis of Example 59.

| Ex. | Compound Name | Intermediate |
|---|---|---|
| 91 | (R)-2-Hydroxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one | P |
| 92 | (R)-2-Hydroxy-1-[4-(2-{6-[5-(2H-pyrazol-3-yl)-pyridin-2-yloxy]-benzofuran-3-yl}-ethyl)-piperazin-1-yl]-propan-1-one | Q |
| 94 | (R)-2-Hydroxy-1-(4-{6-[4-(2H-pyrazol-3-yl)-phenoxy]-imidazo[1,2-a]pyridin-2-ylmethyl}-piperazin-1-yl)-propan-1-one | R |

Example 60

Preparation of 2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone (60)

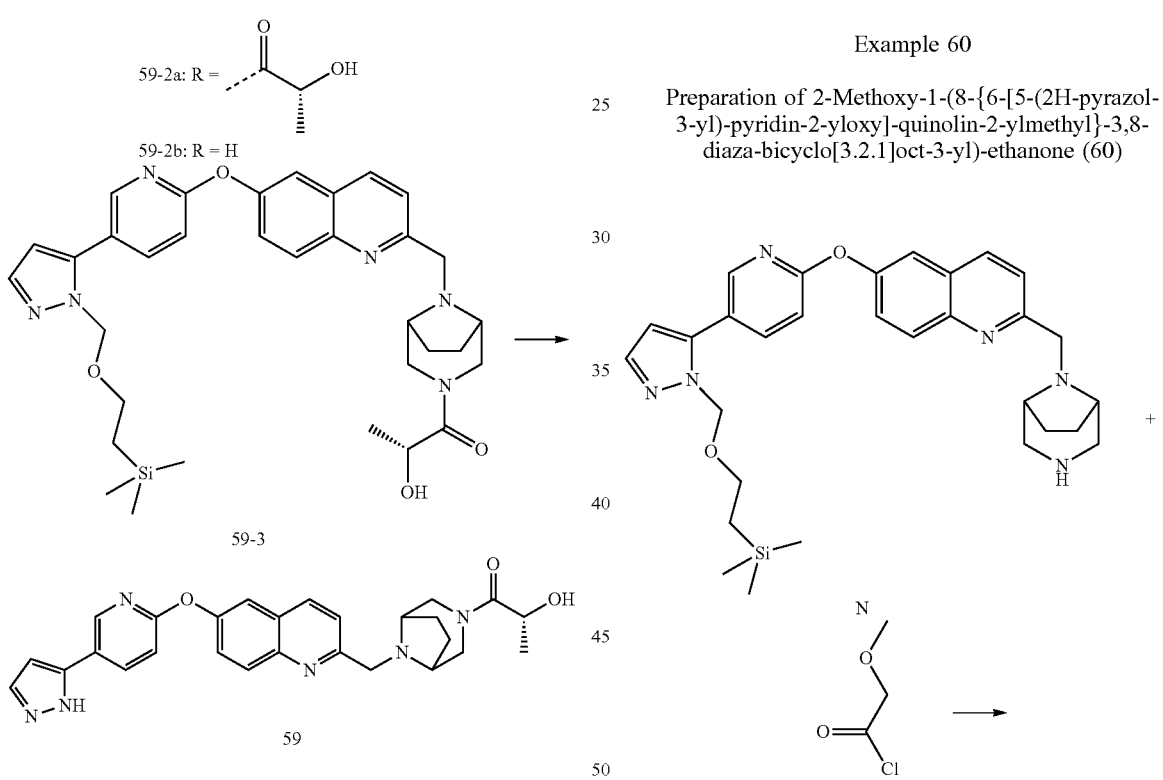

To a stirred solution of N (100 mg, 0.184 mmol) in DMF (1 mL) is added 59-1 (18.3 mg, 0.203 mmol), DIPEA (39 µL, 0.22 mmol), and TBTU (65.1 mg, 0.203 mmol). After 12 h, the reaction mixture is concentrated and the residue is purified on RP-HPLC (C18 column, Solvents=MeCN+0.1% TFA:H2O+0.1% TFA; Gradient=10:90 to 100:0 over 20 min; Flow rate=30 mL/min). The desired fractions are pooled and lyophilized to give a mixture of 59-2a and 59-2b as TFA salts.

To a solution of the mixture of 59-2a and 59-2b (136 mg) in MeOH (5 mL) is added a solution of NaOMe in MeOH (0.5 M, 369 µL, 0.184 mmol). The reaction is stirred for 18 h, neutralized with AcOH, and concentrated to give 59-3, which is dissolved in DCM (1 mL) and treated with TFA (0.300 mL). The resultant mixture is stirred at ambient temperature for 13 h, concentrated, and purified on RP-

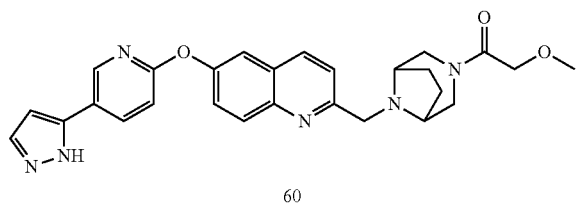

60

Intermediate 60-2 is synthesized from intermediates N (100 mg, 0.184 mmol) and 60-1 (25 μL, 0.28 mmol) according to the procedure described for the synthesis of 57-2 from intermediates N and 57-1.

The title product (60) is synthesized from intermediate 60-2 (101 mg, 0.163 mmol) according to the SEM deprotection procedure described for the synthesis of 57 from intermediate 57-3.

The following examples are synthesized using the appropriate intermediate and acylating reagent according to the procedure described for the synthesis of Example 60.

| Ex. | Compound Name | Intermediate | Acylating Reagents |
|---|---|---|---|
| 77 | 2-Methoxy-1-[4-(2-{6-[5-(2H-pyrazol-3-yl)-pyridin-2-yloxy]-benzofuran-3-yl}-ethyl)-piperazin-1-yl]-ethanone | Q | 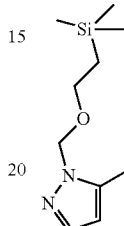 |
| 89 | 2-Methoxy-1-(4-{6-[4-(2H-pyrazol-3-yl)-phenoxy]-imidazo[1,2-a]pyridin-2-ylmethyl}-piperazin-1-yl)-ethanone | R | 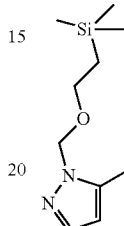 |
| 95 | 1-(4-{6-[4-(2H-Pyrazol-3-yl)-phenoxy]-imidazo[1,2-a]pyridin-2-ylmethyl}-piperazin-1-yl)-ethanone | R | (acetic anhydride) |

Example 61

Preparation of (S)-3-Hydroxy-1-(1-{(S)-6-[5-(2H-pyrazol-3-yl)-pyridin-2-yloxy]-2,3-dihydro-benzofuran-2-ylmethyl}-piperidin-4-yl)-pyrrolidin-2-one (61)

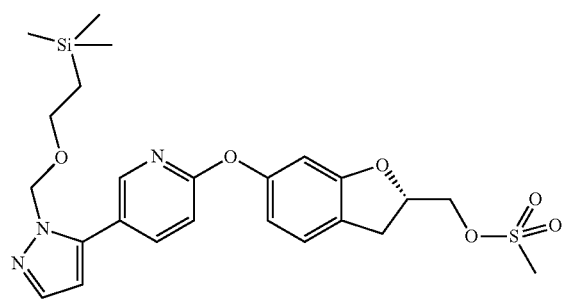

AH

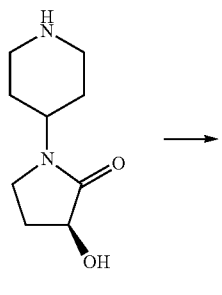

61-1

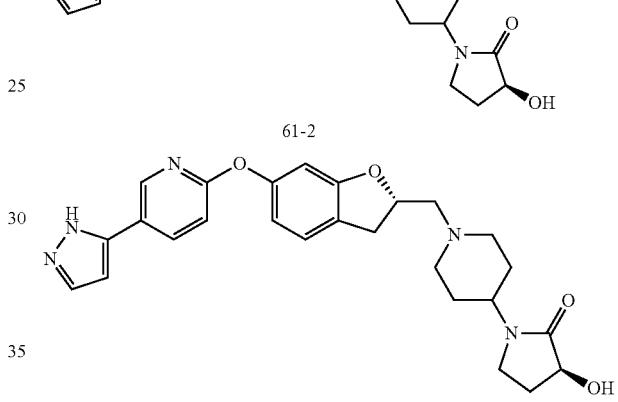

A solution of AH (235 mg, 0.454 mmol) and 61-1 (200 mg, 1.09 mmol) in DMSO (1 mL) is heated at 80° C. After 76 h, the crude reaction mixture is purified on RP-HPLC (C18 column, Solvents=MeCN+0.1% TFA:H2O+0.1% TFA; Gradient=5:95 to 95:5 over 20 min; Flow rate=30 mL/min). The desired fractions are pooled and lyophilized to give 61-2.

The title product (61) is synthesized from 61-2 (192 mg. 0.267 mmol) according to the procedure described for the synthesis of Example 50 from 50-2.

The following examples are synthesized from the appropriate intermediate and amine reagent according to the procedure described for the synthesis of Example 61.

| Ex. | Compound Name | Intermediate | Amine Reagent |
|---|---|---|---|
| 62 | (S)-3-Hydroxy-1-(1-{(R)-6-[5-(2H-pyrazol-3-yl)-pyridin-2-yloxy]-2,3-dihydro-benzofuran-2-ylmethyl}-piperidin-4-yl)-pyrrolidin-2-one | AG | (piperidine-pyrrolidinone-OH) |

| Ex. | Compound Name | Intermediate | Amine Reagent |
|---|---|---|---|
| 63 | 1-(1-{(R)-6-[5-(2H-Pyrazol-3-yl)-pyridin-2-yloxy]-2,3-dihydro-benzofuran-2-ylmethyl}-piperidin-4-yl)-pyrrolidin-2-one | AG | |
| 64 | 1-(1-{(S)-6-[5-(2H-Pyrazol-3-yl)-pyridin-2-yloxy]-2,3-dihydro-benzofuran-2-ylmethyl}-piperidin-4-yl)-pyrrolidin-2-one | AH | |

Example 66

Preparation of 2-(4-Methanesulfonyl-piperazin-1-ylmethyl)-6-[5-(2H-pyrazol-3-yl)-pyridin-2-yloxy]-quinoline (66)

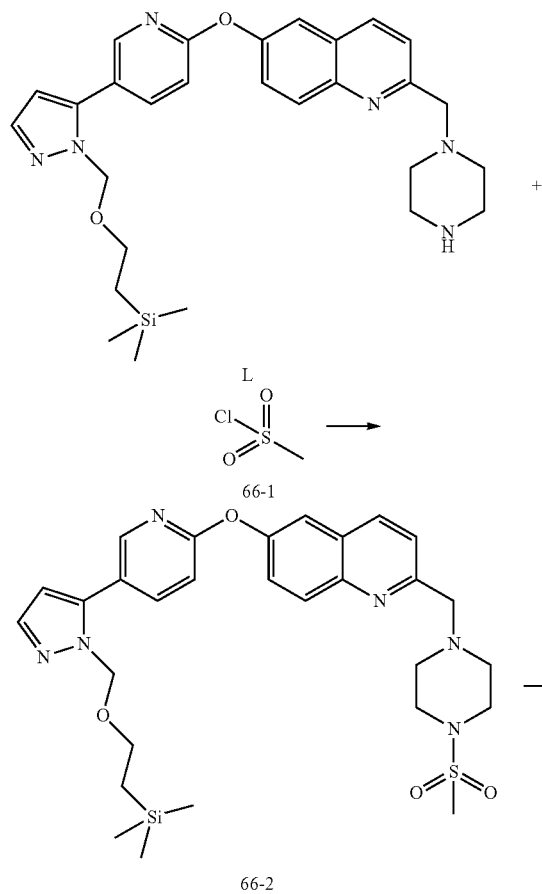

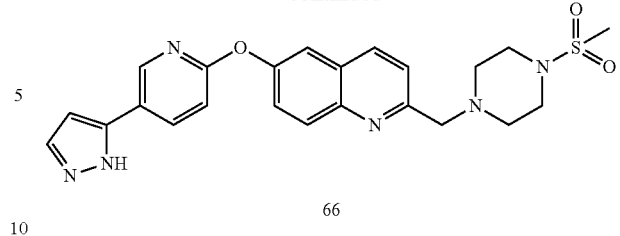

To a stirred solution of intermediate L (70.0 mg, 0.135 mmol) and TEA (75.5 µL, 0.542 mmol) in DCM (2.0 mL) is added intermediate 66-1 (16.3 µL, 0.203 mmol). After 16 h, the reaction is concentrated and the resultant crude mixture is purified on RP-HPLC (C18 column, Solvents=MeCN+0.1% TFA:H2O+0.1% TFA; Gradient=5:95 to 95:5 over 20 min; Flow rate=30 mL/min). The desired fractions are pooled and lyophilized. The residue is dissolved in MeOH, passed through a PL-HCO$_3$ cartridge, and concentrated to give 66-2.

The title product (66) is synthesized form intermediate 66-2 (78.0 mg, 0.131 mmol) according to the procedure described for the synthesis of Example 50 from 50-2.

The following example is synthesized from intermediate L and ethanesulfonyl chloride according to the procedure described for the synthesis of Example 66.

| Ex. | Compound Name |
|---|---|
| 67 | 2-(4-Ethanesulfonyl-piperazin-1-ylmethyl)-6-[5-(2H-pyrazol-3-yl)-pyridin-2-yloxy]-quinoline |

Example 68

Preparation of 1-[1-(2-{6-[5-(2H-Pyrazol-3-yl)-pyridin-2-yloxy]-2,3-dihydro-benzofuran-3-yl}-ethyl)-piperidin-4-yl]-pyrrolidin-2-one (68)

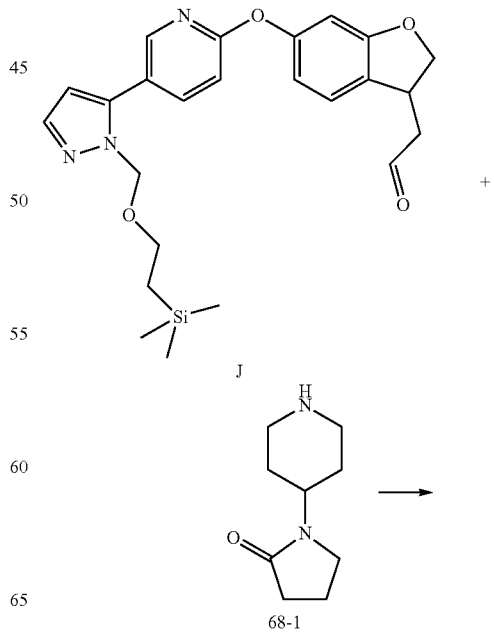

-continued

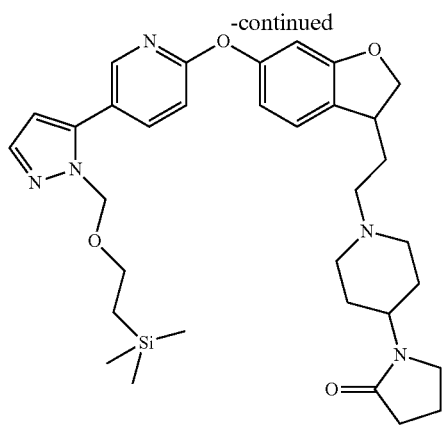

68-2

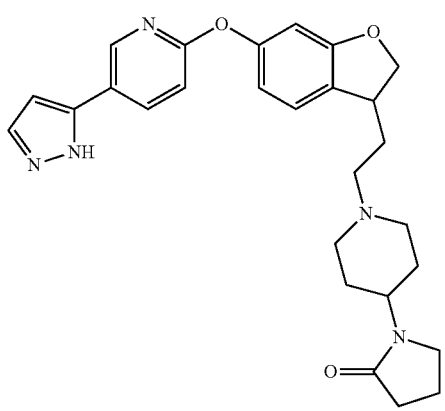

68

A mixture of intermediate J (100 mg, 0.221 mmol) and 68-1 (74.5 mg, 0.443 mmol) in dry DCE (2 mL) is stirred for 20 min; sodium triacetoxyborohydride (212 mg, 0.443 mmol) is added, and the resultant mixture is stirred at ambient temperature. After 20 h, the mixture is diluted with DCM (10 mL). The organic layer is washed with saturated aqueous NaHCO$_3$ (10 mL), dried over MgSO$_4$, filtered and concentrated. The residue is purified by RP-HPLC (C18 column, Solvents=MeCN+0.1% TFA:H2O+0.1% TFA; Gradient=5:95 to 95:5 over 20 min; Flow rate=30 mL/min). The desired fractions are pooled and lyophilized. The residue is dissolved in MeOH, passed through a PL-HCO$_3$ cartridge, and concentrated to give 68-2.

The title product (68) is synthesized from intermediate 68-2 (105 mg, 0.174 mmol) according to the procedure described for the synthesis of Example 50 from 50-2.

The following examples are synthesized from intermediate (J) or (I), and the appropriate amine reagents (free base or salt form) according to the procedure described for the synthesis of Example 68. Generally, for the syntheses that utilize amine salts, an equivalent of triethylamine is added prior to the addition of sodium triacetoxyborohydride.

| Ex. | Compound Name | Intermediate | Amine Reagent |
|---|---|---|---|
| 69 | 3-[1-(2-{6-[5-(2H-Pyrazol-3-yl)-pyridin-2-yloxy]-2,3-dihydro-benzofuran-3-yl}-ethyl)-piperidin-4-yl]-oxazolidin-2-one | J | |
| 70 | (S)-3-Hydroxy-1-[1-(2-{6-[5-(2H-pyrazol-3-yl)-pyridin-2-yloxy]-2,3-dihydro-benzofuran-3-yl}-ethyl)-piperidin-4-yl]-pyrrolidin-2-one | J | |
| 71 | 1-Methanesulfonyl-4-(2-{6-[5-(2H-pyrazol-3-yl)-pyridin-2-yloxy]-2,3-dihydro-benzofuran-3-yl}-ethyl)-piperazine | J | |
| 72 | 1-[1-(2-{6-[5-(2H-Pyrazol-3-yl)-pyridin-2-yloxy]-benzofuran-3-yl}-ethyl)-piperidin-4-yl]-pyrrolidin-2-one | I | |
| 73 | (S)-3-Hydroxy-1-[1-(2-{6-[5-(2H-pyrazol-3-yl)-pyridin-2-yloxy]-benzofuran-3-yl}-ethyl)-piperidin-4-yl]-pyrrolidin-2-one | I | |
| 74 | 1-Methanesulfonyl-4-(2-{6-[5-(2H-pyrazol-3-yl)-pyridin-2-yloxy]-benzofuran-3-yl}-ethyl)-piperazine | I | |

Example 97

Preparation of 1-(4-{6-[5-(2H-Pyrazol-3-yl)-pyridin-2-yloxy]-benzofuran-3-ylmethyl}-[1,4]diazepan-1-yl)-ethanone (97)

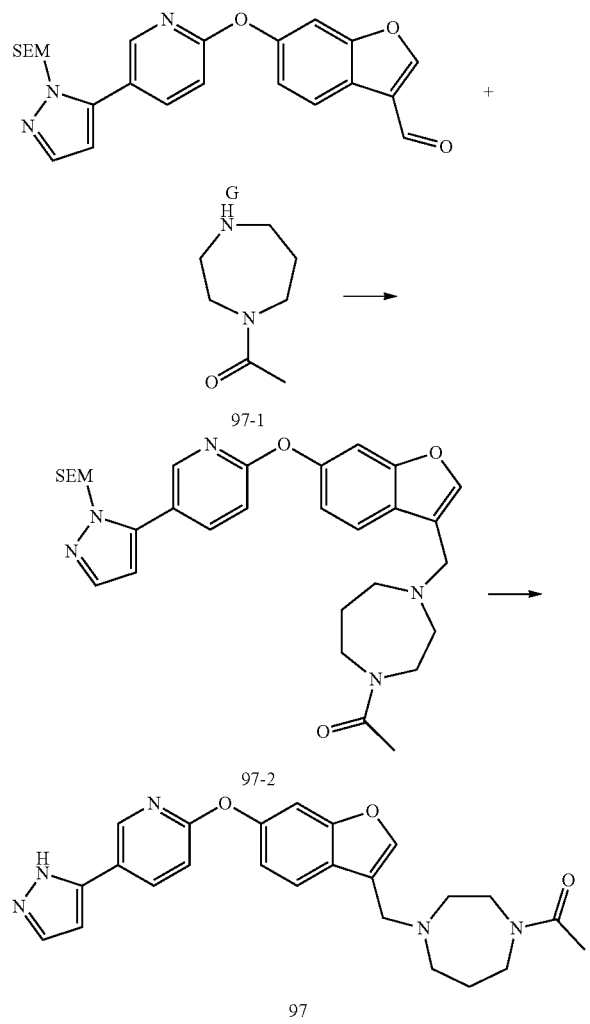

To a solution of 97-1 (46 mg, 0.32 mmol) in a mixture of DCM (3 mL) and DMF (2 mL) is added glacial AcOH (12 μL, 0.21 mmol) and ZnCl$_2$ (1.0 M in Et$_2$O, 0.27 mL). Next, G (60 mg, 0.13 mmol) and sodium triacetoxyborohydride (250 mg, 1.16 mmol) are added sequentially, and the resultant reaction is stirred at ambient temperature. After 1 h, additional amount of 97-1 (64 mg, 0.45 mmol) and sodium triacetoxyborohydride (75 mg, 0.35 mmol) are added. After 18 h, the reaction is diluted with EtOAc (50 mL), and washed with saturated aqueous NaHCO$_3$ (50 mL) and brine (20 mL). The aqueous layer is extracted with EtOAc (50 mL). The combined organic layers are dried over Na$_2$SO$_4$, filtered and concentrated to give 97-2.

To a solution of 97-2 (130 mg, 0.231 mmol) in DCM (5 mL) is added TFA (5 mL), and the reaction is stirred at ambient temperature for 2 h. The mixture is concentrated; the residue is dissolved in DCM (20 mL), and treated with a solution of 2M NH$_3$ in MeOH (10 mL). The mixture is concentrated and the residue is purified by silica gel chromatography (0-10% MeOH in DCM) to give the title product (97).

The following examples are synthesized from intermediate G, and the appropriate amine reagents (free base or salt form) according to the procedure described for the synthesis of Example 97.

| Ex. | Compound Name | Intermediate | Amine Reagent |
|---|---|---|---|
| 103 | 1-{6-[5-(2H-Pyrazol-3-yl)-pyridin-2-yloxy]-benzofuran-3-ylmethyl}-piperidine-4-carboxylic acid methylamide | G | |
| 104 | N-(1-{6-[5-(2H-Pyrazol-3-yl)-pyridin-2-yloxy]-benzofuran-3-ylmethyl}-piperidin-4-yl)-acetamide | G | |
| 105 | N-(1-{6-[5-(2H-Pyrazol-3-yl)-pyridin-2-yloxy]-benzofuran-3-ylmethyl}-piperidin-4-yl)-methanesulfonamide | G | |
| 106 | N-(1-{6-[5-(2H-Pyrazol-3-yl)-pyridin-2-yloxy]-benzofuran-3-ylmethyl}-piperidin-4-ylmethyl)-acetamide | G | |
| 107 | 1-{4-[({6-[5-(2H-Pyrazol-3-yl)-pyridin-2-yloxy]-benzofuran-3-ylmethyl}-amino)-methyl]-piperidin-1-yl}-ethanone | G | |
| 108 | 1-[4-({6-[5-(2H-Pyrazol-3-yl)-pyridin-2-yloxy]-benzofuran-3-ylmethyl}-amino)-piperidin-1-yl]-ethanone | G | |
| 109 | (S)-3-Hydroxy-1-(1-{6-[5-(2H-pyrazol-3-yl)-pyridin-2-yloxy]-benzofuran-3-ylmethyl}-piperidin-4-yl)-pyrrolidin-2-one | G | |
| 110 | 2-Methyl-8-{6-[5-(2H-pyrazol-3-yl)-pyridin-2-yloxy]-benzofuran-3-ylmethyl}-2,8-diazaspiro[4.5]decan-1-one | G | |

-continued

| Ex. | Compound Name | Intermediate | Amine Reagent |
|---|---|---|---|
| 111 | 2-(4-{6-[5-(2H-Pyrazol-3-yl)-pyridin-2-yloxy]-benzofuran-3-ylmethyl}-piperazin-1-yl)-1-pyrrolidin-1-yl-ethanone | G | 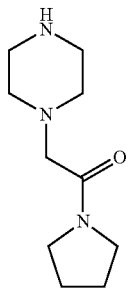 [SMILES: O=C(CN1CCNCC1)N1CCCC1] |

Example 98

Preparation of 2-Hydroxy-N-methyl-N-((R)-1-{6-[5-(2H-pyrazol-3-yl)-pyridin-2-yloxy]-quinolin-2-ylmethyl}-pyrrolidin-3-yl)-acetamide (98)

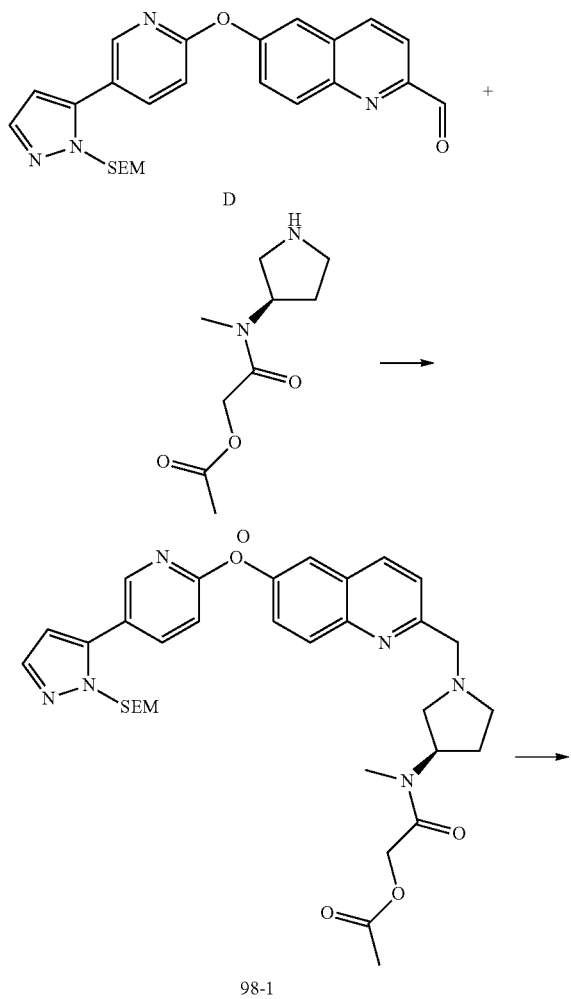

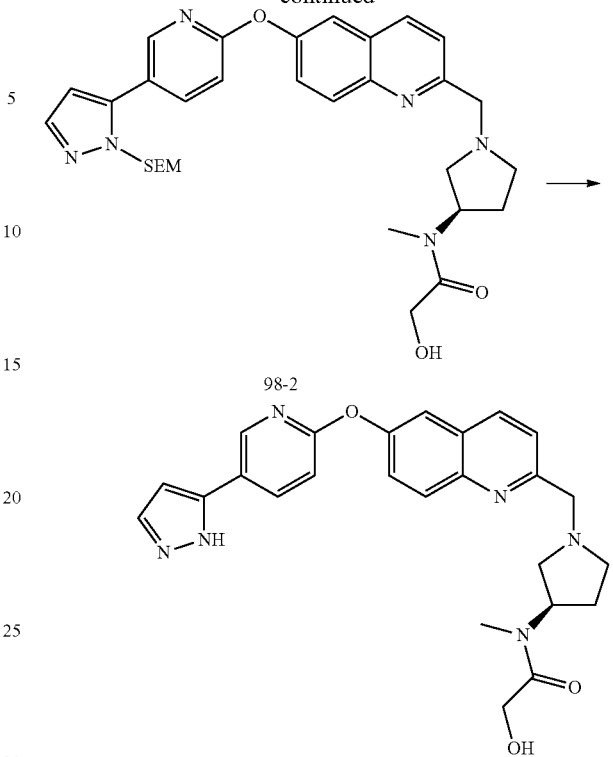

A mixture of D (300 mg, 0.652 mmol) and O (250 mg, 1.06 mmol) in DCM (3 mL) and DMF (1 mL) is treated with TEA (0.55 mL, 3.9 mmol). The mixture is stirred at 50° C. for 1 h, and cooled to ambient temperature. Sodium triacetoxyborohydride (310 mg, 1.43 mmol) is added, and the mixture is stirred at ambient temperature for 18 h. The reaction is quenched with water (50 mL) and extracted with EtOAc (2×50 mL). The combined organic layers are washed with brine (30 mL), dried over Na$_2$SO$_4$, filtered and concentrated. The residue is purified by silica gel chromatography (0-5% MeOH in DCM) to give 98-1.

To a solution of 98-1 (280 mg, 0.444 mmol) in MeOH (6 mL) is added a solution of LiOH (54 mg, 2.2 mmol) in water (3 mL). The mixture is stirred for 24 h, neutralized with HCl to pH 5-6, diluted with saturated NaHCO$_3$ (25 mL) and extracted with EtOAc (2×50 mL). The combined organic layers are dried over Na$_2$SO$_4$, filtered and concentrated to give 98-2.

To solution of 98-2 (248 mg, 0.421 mmol) in DCM (10 mL) is added TFA (10 mL), and the mixture is stirred at ambient temperature for 2 h. The reaction mixture is concentrated, and the crude reaction mixture is purified by silica gel chromatography (0-10% MeOH in DCM). The desired fractions are concentrated, and the residue dissolved in EtOAc (20 mL). Heptane (100 mL) is added, and the mixture is filtered. The resultant solid is washed with 20% EtOAc in heptane and air dried to afford the title product (98).

The following examples are synthesized from intermediate D and the appropriate amine reagents (TFA salt) according to the procedure described for the synthesis of Example 98.

| Ex. | Compound Name | Intermediate | Amine Reagent |
|---|---|---|---|
| 99 | 2-Hydroxy-N-methyl-N-((S)-1-{6-[5-(2H-pyrazol-3-yl)-pyridin-2-yloxy]-benzofuran-3-ylmethyl}-pyrrolidin-3-yl)-acetamide | D | |
| 100 | 2-Hydroxy-1-[(R)-3-(methyl-{6-[5-(2H-pyrazol-3-yl)-pyridin-2-yloxy]-quinolin-2-ylmethyl}-amino)-pyrrolidin-1-yl]-ethanone | D | |
| 101 | 2-Hydroxy-1-[(S)-3-(methyl-{6-[5-(2H-pyrazol-3-yl)-pyridin-2-yloxy]-quinolin-2-ylmethyl}-amino)-pyrrolidin-1-yl]-ethanone | D | |
| 102 | 2-Hydroxy-1-(7-{6-[5-(2H-pyrazol-3-yl)-pyridin-2-yloxy]-quinolin-2-ylmethyl}-2,7-diaza-spiro[4.4]non-2-yl)-ethanone | D | |

The following examples are synthesized from intermediate G and the appropriate amine reagents (TFA salt) according to the procedure described for the synthesis of Example 98.

| Ex. | Compound Name | Intermediate | Amine Reagent |
|---|---|---|---|
| 113 | 2-Hydroxy-N-methyl-N-((R)-1-{6-[5-(2H-pyrazol-3-yl)-pyridin-2-yloxy]-benzofuran-3-ylmethyl}-pyrrolidin-3-yl)-acetamide | G | |
| 114 | 2-Hydroxy-N-methyl-N-((S)-1-{6-[5-(2H-pyrazol-3-yl)-pyridin-2-yloxy]-benzofuran-3-ylmethyl}-pyrrolidin-3-yl)-acetamide | G | |
| 115 | 2-Hydroxy-1-(7-{6-[5-(2H-pyrazol-3-yl)-pyridin-2-yloxy]-benzofuran-3-ylmethyl}-2,7-diaza-spiro[4.4]non-2-yl)-ethanone | G | |

Example 112

Preparation of 1-(4-{6-[5-(2H-Pyrazol-3-yl)-pyridin-2-yloxy]-benzofuran-3-carbonyl}-piperazin-1-yl)-ethanone (112)

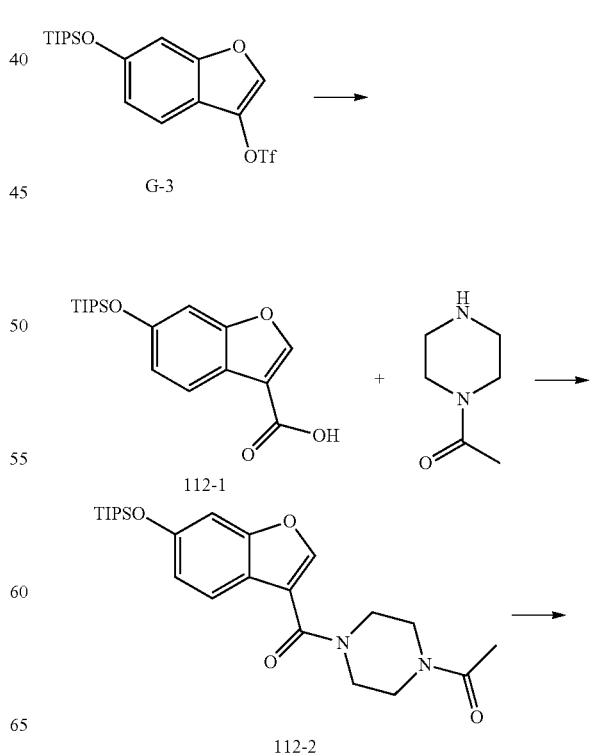

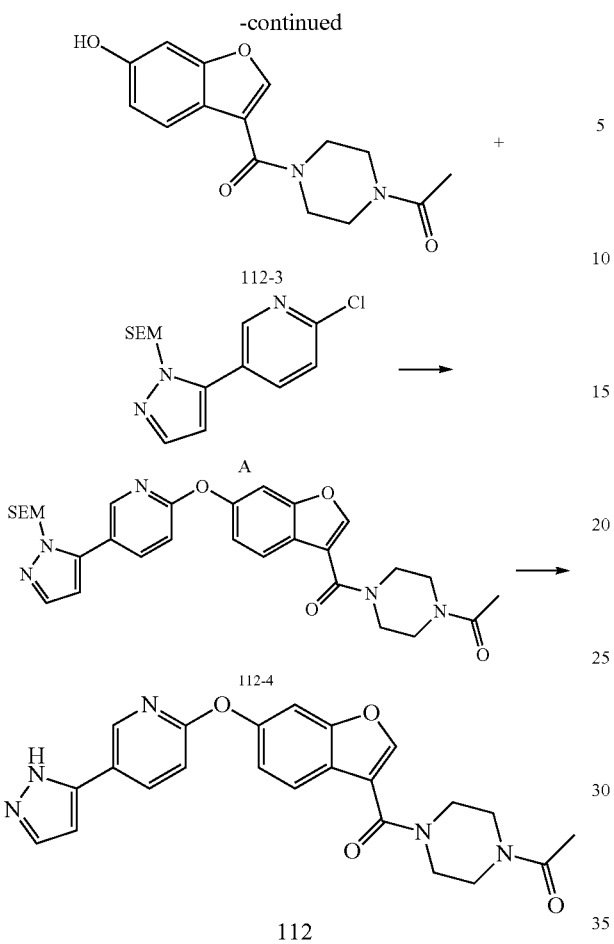

combined organic layers are washed with brine (30 mL), dried over Na₂SO₄, filtered and concentrated. The residue is purified by silica gel chromatography (0-4% MeOH in DCM) to give 112-4.

To a solution of 112-4 (30 mg, 0.053 mmol) in DCM (3 mL) is added TFA (3 mL). The reaction is stirred at ambient temperature for 3 h and concentrated. The resultant residue is dissolved in MeOH, passed through a PL-HCO₃ cartridge, and concentrated. The residue is dissolved in EtOAc (5 mL), treated with heptane (30 mL) and filtered to give the title product (112).

Example 116

Preparation of 1-(4-{6-[5-(2H-Pyrazol-3-yl)-pyridin-2-yloxy]-quinolin-2-ylmethyl}-piperazine-1-carbonyl)-cyclopropanecarbonitrile (116)

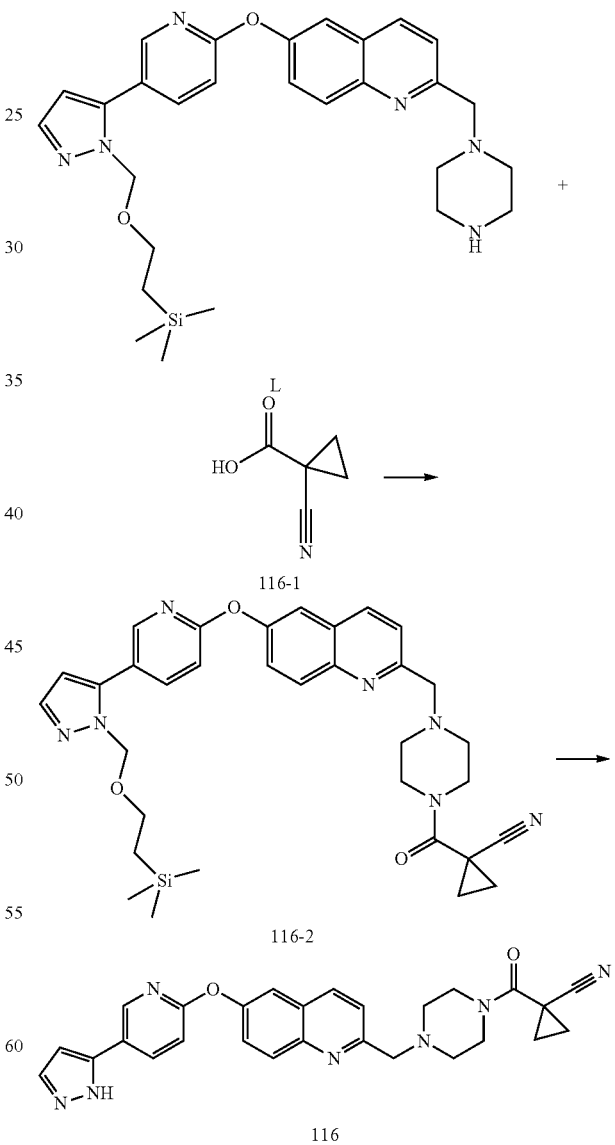

To a mixture of G-3 (100 mg, 0.228 mmol) in DMF (2 mL) is added Mo(CO)₆ (61 mg, 0.23 mmol) and trans-di-mu-acetobis[2-(di-O-tolylphosphino)benzyl]dipalladium(II) (Hermann's Catalyst, 22 mg, 0.023 mmol). The reaction is heated at 100° C. in a microwave for 15 min, cooled to ambient temperature, quenched with 1M HCl (20 mL) and extracted with EtOAc (2×20 mL). The combined organic layers are dried over Na₂SO₄, filtered and concentrated. The crude is purified by silica gel chromatography (0-50% EtOAc in heptane) to give 112-1.

To a stirred solution of 112-1 (84 mg, 0.25 mmol) in DMF (5 mL) is added HATU (145 mg, 0.377 mmol) and triethylamine (0.107 mL, 0.753 mmol) After 30 min, N-acetylpiperazine (49 mg, 0.38 mmol) is added, and the mixture is stirred for 24 h. The reaction is quenched with saturated aqueous NH₄Cl (20 mL) and extracted with EtOAc (2×20 mL). The combined organic layers are dried over Na₂SO₄, filtered and concentrated to give 112-2.

To a stirred solution of 112-2 (137 mg, 0.251 mmol) in THF (5 mL) at ambient temperature is added TBAF (1.0M in THF, 0.277 mL). After 72 h, the reaction is quenched with water (50 mL) and extracted with EtOAc (3×50 mL). The combined organic layers are dried over Na₂SO₄, filtered and concentrated. The crude is purified by silica gel chromatography (0-7% MeOH in DCM) to give 112-3.

A mixture of 112-3 (56 mg, 0.19 mmol), A (120 mg, 0.377 mmol), and K₂CO₃ (132 mg, 0.942 mmol) in DMSO (2 mL) is heated at 150° C. for 1 h. The reaction is quenched with water (50 mL) and extracted with EtOAc (3×50 mL). The A solution of 116-1 (17.8 mg, 0.160 mmol) in DMA (400 μL) is sequentially treated with HATU (16.8 mg, 0.160 mmol), a solution of L (75.0 mg, 0.145 mmol) in DMA (400 μL), and DIPEA (78 μL, 0.44 mmol). The reaction is shaken overnight. The crude mixture is purified by RP-HPLC to afford 116-2, which is dissolved in DCE (1.0 mL) and treated with TFA (0.2 mL). After shaking for 2 h, the mixture is concentrated and purified by RP-HPLC to afford the title product (116).

Compounds 117-151 are synthesized using Intermediate L and the appropriate acid reagent according to the procedure described for the synthesis of Example 116.

| Ex. | Compound Name | Acid Reagent |
|---|---|---|
| 117 | (S)-3-Hydroxy-1-(4-{6-[5-(2H-pyrazol-3-yl)-pyridin-2-yloxy]-quinolin-2-ylmethyl}-piperazin-1-yl)-butan-1-one | |
| 118 | (S)-2-Methoxy-1-(4-{6-[5-(2H-pyrazol-3-yl)-pyridin-2-yloxy]-quinolin-2-ylmethyl}-piperazin-1-yl)-propan-1-one | |
| 119 | (1-Hydroxy-cyclopentyl)-(4-{6-[5-(2H-pyrazol-3-yl)-pyridin-2-yloxy]-quinolin-2-ylmethyl}-piperazin-1-yl)-methanone | |
| 120 | (R)-2-Hydroxy-3-methyl-1-(4-{6-[5-(2H-pyrazol-3-yl)-pyridin-2-yloxy]-quinolin-2-ylmethyl}-piperazin-1-yl)-butan-1-one | |
| 121 | (R)-3-Hydroxy-1-(4-{6-[5-(2H-pyrazol-3-yl)-pyridin-2-yloxy]-quinolin-2-ylmethyl}-piperazin-1-yl)-butan-1-one | |
| 122 | 3-Hydroxy-3-methyl-1-(4-{6-[5-(2H-pyrazol-3-yl)-pyridin-2-yloxy]-quinolin-2-ylmethyl}-piperazin-1-yl)-butan-1-one | |
| 123 | (R)-2-Hydroxy-1-(4-{6-[5-(2H-pyrazol-3-yl)-pyridin-2-yloxy]-quinolin-2-ylmethyl}-piperazin-1-yl)-propan-1-one | |
| 124 | 2-Ethoxy-1-(4-{6-[5-(2H-pyrazol-3-yl)-pyridin-2-yloxy]-quinolin-2-ylmethyl}-piperazin-1-yl)-ethanone | |
| 125 | 2-Hydroxy-2-methyl-1-(4-{6-[5-(2H-pyrazol-3-yl)-pyridin-2-yloxy]-quinolin-2-ylmethyl}-piperazin-1-yl)-propan-1-one | |
| 126 | (1-Hydroxy-cyclopropyl)-(4-{6-[5-(2H-pyrazol-3-yl)-pyridin-2-yloxy]-quinolin-2-ylmethyl}-piperazin-1-yl)-methanone | |
| 127 | (S)-2-Hydroxy-1-(4-{6-[5-(2H-pyrazol-3-yl)-pyridin-2-yloxy]-quinolin-2-ylmethyl}-piperazin-1-yl)-butan-1-one | |
| 128 | 2-Methoxy-2-methyl-1-(4-{6-[5-(2H-pyrazol-3-yl)-pyridin-2-yloxy]-quinolin-2-ylmethyl}-piperazin-1-yl)-propan-1-one | |
| 129 | (S)-2-Hydroxy-1-(4-{6-[5-(2H-pyrazol-3-yl)-pyridin-2-yloxy]-quinolin-2-ylmethyl}-piperazin-1-yl)-propan-1-one | |
| 130 | 2-Isopropoxy-1-(4-{6-[5-(2H-pyrazol-3-yl)-pyridin-2-yloxy]-quinolin-2-ylmethyl}-piperazin-1-yl)-ethanone | |
| 131 | (4-{6-[5-(2H-Pyrazol-3-yl)-pyridin-2-yloxy]-quinolin-2-ylmethyl}-piperazin-1-yl)-(tetrahydro-pyran-4-yl)-methanone | |
| 132 | (4-{6-[5-(2H-Pyrazol-3-yl)-pyridin-2-yloxy]-quinolin-2-ylmethyl}-piperazin-1-yl)-(S)-tetrahydro-furan-2-yl-methanone | |
| 133 | (4-{6-[5-(2H-Pyrazol-3-yl)-pyridin-2-yloxy]-quinolin-2-ylmethyl}-piperazin-1-yl)-(R)-tetrahydro-furan-2-yl-methanone | |
| 134 | (R)-2-Hydroxy-1-(4-{6-[5-(2H-pyrazol-3-yl)-pyridin-2-yloxy]-quinolin-2-ylmethyl}-piperazin-1-yl)-butan-1-one | |
| 135 | 3-Hydroxy-2,2-dimethyl-1-(4-{6-[5-(2H-pyrazol-3-yl)-pyridin-2-yloxy]-quinolin-2-ylmethyl}-piperazin-1-yl)-propan-1-one | |
| 136 | (3-Oxa-bicyclo[3.1.0]hex-6-yl)-(4-{6-[5-(2H-pyrazol-3-yl)-pyridin-2-yloxy]-quinolin-2-ylmethyl}-piperazin-1-yl)-methanone | |
| 137 | (S)-2-Hydroxy-3-methyl-1-(4-{6-[5-(2H-pyrazol-3-yl)-pyridin-2-yloxy]-quinolin-2-ylmethyl}-piperazin-1-yl)-butan-1-one | |

| Ex. | Compound Name | Acid Reagent |
|---|---|---|
| 138 | (1-Hydroxymethyl-cyclopropyl)-(4-{6-[5-(2H-pyrazol-3-yl)-pyridin-2-yloxy]-quinolin-2-ylmethyl}-piperazin-1-yl)-methanone | 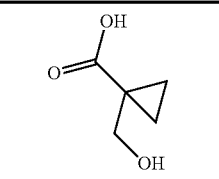 |
| 139 | (3-Hydroxy-cyclobutyl)-(4-{6-[5-(2H-pyrazol-3-yl)-pyridin-2-yloxy]-quinolin-2-ylmethyl-piperazin-1-yl)-methanone |  |
| 140 | (R)-2-Methoxy-1-(4-{6-[5-(2H-pyrazol-3-yl)-pyridin-2-yloxy]-quinolin-2-ylmethyl}-piperazin-1-yl)-propan-1-one | 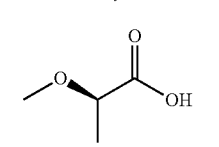 |
| 141 | (4-{6-[5-(2H-Pyrazol-3-yl)-pyridin-2-yloxy]-quinolin-2-ylmethyl}-piperazin-1-yl)-(R)-tetrahydro-furan-3-yl-methanone | 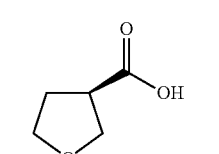 |
| 142 | 4-Methoxy-1-(4-{6-[5-(2H-pyrazol-3-yl)-pyridin-2-yloxy]-quinolin-2-ylmethyl}-piperazin-1-yl)-butan-1-one | 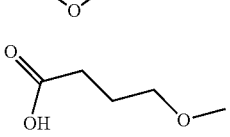 |
| 143 | (1-Hydroxy-cyclobutyl)-(4-{6-[5-(2H-pyrazol-3-yl)-pyridin-2-yloxy]-quinolin-2-ylmethyl}-piperazin-1-yl)-methanone | 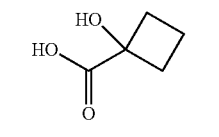 |
| 144 | 2-Propoxy-1-(4-{6-[5-(2H-pyrazol-3-yl)-pyridin-2-yloxy]-quinolin-2-ylmethyl}-piperazin-1-yl)-ethanone | 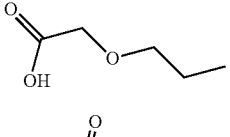 |
| 145 | 2,2-Dimethyl-3-oxo-3-(4-{6-[5-(2H-pyrazol-3-yl)-pyridin-2-yloxy]-quinolin-2-ylmethyl}-piperazin-1-yl)-propionitrile | 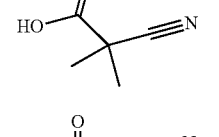 |
| 146 | 1-(4-{6-[5-(2H-Pyrazol-3-yl)-pyridin-2-yloxy]-quinolin-2-ylmethyl}-piperazine-1-carbonyl)-cyclobutanecarbonitrile | 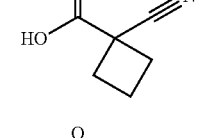 |
| 147 | 1-(4-{6-[5-(2H-Pyrazol-3-yl)-pyridin-2-yloxy]-quinolin-2-ylmethyl}-piperazine-1-carbonyl)-cyclopentanecarbonitrile | 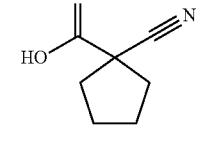 |
| 148 | 4-(4-{6-[5-(2H-Pyrazol-3-yl)-pyridin-2-yloxy]-quinolin-2-ylmethyl}-piperazine-1-carbonyl)-tetrahydro-pyran-4-carbonitrile | 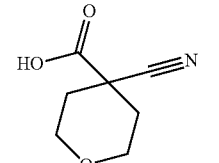 |
| 149 | 2-Methyl-3-oxo-3-(4-{6-[5-(2H-pyrazol-3-yl)-pyridin-2-yloxy]-quinolin-2-ylmethyl}-piperazin-1-yl)-propionitrile | 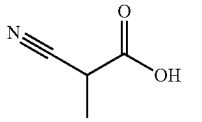 |
| 150 | (3-Hydroxy-3-methyl-cyclobutyl)-(4-{6-[5-(2H-pyrazol-3-yl)-pyridin-2-yloxy]-quinolin-2-ylmethyl}-piperazin-1-yl)-methanone | 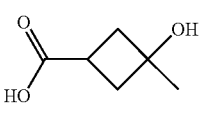 |
| 151 | ((1R,2S)-2-Hydroxy-cyclopentyl)-(4-{6-[5-(2H-pyrazol-3-yl)-pyridin-2-yloxy]-quinolin-2-ylmethyl}-piperazin-1-yl)-methanone | 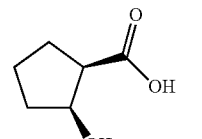 |

TABLE 2

Mass spectral and HPLC data for compounds 1-151

| Ex. | Obs. Mass (m/z) | R.T. (min) |
|---|---|---|
| 1 | 373.4 | 2.65 |
| 2 | 400.3 | 2.63 |
| 3 | 414.3 | 2.54 |
| 4 | 387.4 | 2.63 |
| 5 | 387.4 | 2.65 |
| 6 | 387.4 | 2.64 |
| 7 | 444.3 | 2.52 |
| 8 | 485.3 | 2.59 |
| 9 | 458.4 | 2.62 |
| 10 | 413.3 | 2.66 |
| 11 | 387.4 | 2.66 |
| 12 | 428.4 | 2.65 |
| 13 | 428.4 | 2.65 |
| 14 | 401.3 | 2.67 |
| 15 | 401.3 | 2.67 |
| 16 | 375.4 | 2.64 |
| 17 | 415.4 | 2.66 |
| 18 | 401.3 | 2.66 |
| 19 | 458.4 | 2.62 |
| 20 | 458.4 | 2.65 |
| 21 | 458.4 | 2.66 |
| 22 | 401.3 | 2.65 |
| 23 | 458.4 | 2.61 |
| 24 | 459.3 | 2.49 |
| 25 | 429.3 | 2.48 |
| 26 | 402.2 | 2.48 |
| 27 | 429.3 | 2.47 |
| 28 | 443.3 | 2.48 |
| 29 | 485.3 | 2.47 |
| 30 | 459.3 | 2.5 |
| 31 | 473.3 | 2.64 |
| 32 | 443.3 | 2.48 |
| 33 | 471.3 | 2.49 |
| 34 | 458.4 | 2.56 |
| 35 | 471.1 | 2.61 |
| 36 | 469.5 | 2.49 |
| 37 | 443.3 | 2.45 |
| 38 | 457.3 | 2.45 |
| 39 | 473.3 | 2.48 |
| 40 | 455.4 | 2.47 |
| 41 | 457.3 | 2.56 |
| 42 | 374.4 | 2.6 |
| 43 | 371.3 | 2.63 |
| 44 | 399.4 | 2.69 |
| 45 | 388.3 | 2.51 |
| 46 | 388.3 | 2.83 |
| 47 | 388.3 | 2.52 |
| 48 | 445.4 | 2.49 |

TABLE 2-continued

Mass spectral and HPLC data for compounds 1-151

| Ex. | Obs. Mass (m/z) | R.T. (min) |
|---|---|---|
| 49 | 374.4 | 2.43 |
| 50 | 480.4 | 2.55 |
| 51 | 508.2 | 2.66 |
| 52 | 499.3 | 2.56 |
| 53 | 499.3 | 2.56 |
| 54 | 511.3 | 2.57 |
| 55 | 511.3 | 2.58 |
| 56 | 497.2 | 2.55 |
| 57 | 485.3 | 2.62 |
| 58 | 499.4 | 2.67 |
| 59 | 485.3 | 2.62 |
| 60 | 485.3 | 2.64 |
| 61 | 476.4 | 2.58 |
| 62 | 476.4 | 2.58 |
| 63 | 460.4 | 2.63 |
| 64 | 460.3 | 2.64 |
| 65 | 436.3 | 2.57 |
| 66 | 465.3 | 2.55 |
| 67 | 479.3 | 2.58 |
| 68 | 474.3 | 2.56 |
| 69 | 476.4 | 2.55 |
| 70 | 490.2 | 2.53 |
| 71 | 470.4 | 2.57 |
| 72 | 472.3 | 2.58 |
| 73 | 488.3 | 2.53 |
| 74 | 468.4 | 2.6 |
| 75 | 476.3 | 2.89 |
| 76 | 478.3 | 2.76 |
| 77 | 462.3 | 2.89 |
| 78 | 476.3 | 2.88 |
| 79 | 461.3 | 2.72 |
| 80 | 461.3 | 2.71 |
| 81 | 478.3 | 2.73 |
| 82 | 448.3 | 2.53 |
| 83 | 462.3 | 2.73 |
| 84 | 464.2 | 2.52 |
| 85 | 476.3 | 2.9 |
| 86 | 433.3 | 2.62 |
| 87 | 447.3 | 2.65 |
| 88 | 478.4 | 2.55 |
| 89 | 447.3 | 2.52 |
| 90 | 476.3 | 2.56 |
| 91 | 464.3 | 2.54 |
| 92 | 462.3 | 2.54 |
| 93 | 474.4 | 2.56 |
| 94 | 447.3 | 2.5 |
| 95 | 417.3 | 2.52 |
| 96 | 459.3 | 2.52 |
| 97 | 432.3 | 2.62 |
| 98 | 459.3 | 2.51 |
| 99 | 459.3 | 2.51 |
| 100 | 459.3 | 2.48 |
| 101 | 459.3 | 2.48 |
| 102 | 485.2 | 2.49 |
| 103 | 432.4 | 2.62 |
| 104 | 432.4 | 2.61 |
| 105 | 468.4 | 2.64 |
| 106 | 446.4 | 2.62 |
| 107 | 446.4 | 2.64 |
| 108 | 432.4 | 2.62 |
| 109 | 474.3 | 2.59 |
| 110 | 458.4 | 2.68 |
| 111 | 487.4 | 2.7 |
| 112 | 432.4 | 2.78 |
| 113 | 448.3 | 2.63 |
| 114 | 448.3 | 2.62 |
| 115 | 474.3 | 2.6 |
| 116 | 480.4 | 2.57 |
| 117 | 473.4 | 2.61 |
| 118 | 473.0 | 2.59 |
| 119 | 499.3 | 2.68 |
| 120 | 487.3 | 2.67 |
| 121 | 473.4 | 2.6 |
| 122 | 487.3 | 2.64 |
| 123 | 459.3 | 2.6 |
| 124 | 473.4 | 2.65 |
| 125 | 473.4 | 2.63 |
| 126 | 471.3 | 2.62 |
| 127 | 473.4 | 2.63 |
| 128 | 487.3 | 2.72 |
| 129 | 459.3 | 2.6 |
| 130 | 487.3 | 2.7 |
| 131 | 499.3 | 2.64 |
| 132 | 485.3 | 2.65 |
| 133 | 485.3 | 2.64 |
| 134 | 473.4 | 2.63 |
| 135 | 487.3 | 2.64 |
| 136 | 497.3 | 2.66 |
| 137 | 487.3 | 2.67 |
| 138 | 485.3 | 2.6 |
| 139 | 485.3 | 2.59 |
| 140 | 473.4 | 2.64 |
| 141 | 485.3 | 2.63 |
| 142 | 487.3 | 2.66 |
| 143 | 485.3 | 2.65 |
| 144 | 487.3 | 2.72 |
| 145 | 482.3 | 2.73 |
| 146 | 494.2 | 2.75 |
| 147 | 508.2 | 2.81 |
| 148 | 524.3 | 2.7 |
| 149 | 468.3 | 2.67 |
| 150 | 499.3 | 2.61 |
| 151 | 499.3 | 2.65 |

Assessment of Biological Properties

The compounds of the invention are assessed for the ability to interact with human LTA$_4$ hydrolase in an enzymatic assay that measures the ability of the enzyme to cleave the peptide bond of arginyl-aminomethylcoumarin (Arg-AMC). LTA$_4$H Enzyme (1 nM final), Arg-AMC substrate (50 µM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm). In general, the preferred potency range (IC$_{50}$) of compounds in the LTA$_4$H Enzyme assay is between 0.1 nM to 10 µM, the more preferred potency range is 0.1 nM to 0.1 µM, and the most preferred potency range is 0.1 nM to 10 nM.

TABLE 3

IC$_{50}$ values of LTA$_4$H Enzyme assay.

| Ex. | Peptidase IC50 (nM) |
|---|---|
| 1 | 0.43 |
| 2 | 0.46 |
| 3 | 0.5 |
| 4 | 0.48 |
| 5 | 0.6 |
| 6 | 0.57 |
| 7 | 0.4 |
| 8 | 0.86 |
| 9 | 0.5 |
| 10 | 0.48 |
| 11 | 0.53 |
| 12 | 0.34 |
| 13 | 0.79 |
| 14 | 1.2 |
| 15 | 1.0 |
| 16 | 0.7 |

TABLE 3-continued

IC$_{50}$ values of LTA$_4$H Enzyme assay.

| Ex. | Peptidase IC50 (nM) |
|---|---|
| 17 | 0.75 |
| 18 | 0.76 |
| 19 | 0.63 |
| 20 | 0.76 |
| 21 | 0.67 |
| 22 | 0.64 |
| 23 | 0.9 |
| 24 | 2.0 |
| 25 | 1.7 |
| 26 | 2.3 |
| 27 | 1.4 |
| 28 | 1.8 |
| 29 | 1.8 |
| 30 | 1.3 |
| 31 | 1.5 |
| 32 | 1.1 |
| 33 | 0.92 |
| 34 | 0.81 |
| 35 | 2.7 |
| 36 | 1.9 |
| 37 | 0.43 |
| 38 | 1.2 |
| 39 | 2.2 |
| 40 | 1.8 |
| 41 | 0.97 |
| 42 | 0.92 |
| 43 | 2.0 |
| 44 | 2.7 |
| 45 | 2.4 |
| 46 | 2.5 |
| 47 | 1.9 |
| 48 | 2.9 |
| 49 | 2.2 |
| 50 | 0.69 |
| 51 | 0.73 |
| 52 | 0.77 |
| 53 | 0.66 |
| 54 | 1.3 |
| 55 | 1.7 |
| 56 | 0.53 |
| 57 | 0.43 |
| 58 | 0.45 |
| 59 | 0.54 |
| 60 | 0.33 |
| 61 | 1.2 |
| 62 | 0.77 |
| 63 | 0.66 |
| 64 | 0.95 |
| 65 | 4.6 |
| 66 | 1.7 |
| 67 | 2.9 |
| 68 | 1.1 |
| 69 | 0.75 |
| 70 | 1.7 |
| 71 | 1.7 |
| 72 | 0.47 |
| 73 | 0.73 |
| 74 | 1.4 |
| 75 | 0.88 |
| 76 | 1.7 |
| 77 | 0.88 |
| 78 | 0.92 |
| 79 | 1.0 |
| 80 | 0.85 |
| 81 | 2.2 |
| 82 | 1.3 |
| 83 | 0.86 |
| 84 | 1.3 |
| 85 | 1.3 |
| 86 | 0.79 |
| 87 | 1.0 |
| 88 | 1.2 |
| 89 | 0.66 |
| 90 | 1.5 |
| 91 | 2.2 |
| 92 | 1.1 |
| 93 | 0.91 |
| 94 | 0.87 |
| 95 | 0.59 |
| 96 | 1.2 |
| 97 | 0.58 |
| 98 | 0.72 |
| 99 | 0.86 |
| 100 | 0.92 |
| 101 | 2.0 |
| 102 | 0.66 |
| 103 | 0.49 |
| 104 | 0.56 |
| 105 | 0.81 |
| 106 | 0.38 |
| 107 | 0.7 |
| 108 | 0.71 |
| 109 | 0.36 |
| 110 | 0.22 |
| 111 | 0.68 |
| 112 | 1.9 |
| 113 | 0.42 |
| 114 | 0.56 |
| 115 | 0.43 |
| 116 | 0.87 |
| 117 | 3.7 |
| 118 | 0.67 |
| 119 | 8.6 |
| 120 | 5.9 |
| 121 | 4.9 |
| 122 | 3.9 |
| 123 | 0.88 |
| 124 | 2.6 |
| 125 | 1.2 |
| 126 | 1.0 |
| 127 | 2.3 |
| 128 | 0.56 |
| 129 | 0.86 |
| 130 | 2.5 |
| 131 | 2.3 |
| 132 | 2.9 |
| 133 | 2.9 |
| 134 | 3.1 |
| 135 | 5.4 |
| 136 | 6.0 |
| 137 | 2.5 |
| 138 | 1.7 |
| 139 | 3.0 |
| 140 | 0.57 |
| 141 | 2.7 |
| 142 | 2.5 |
| 143 | 1.8 |
| 144 | 2.3 |
| 145 | 1.3 |
| 146 | 3.4 |
| 147 | 12 |
| 148 | 7.9 |
| 149 | 0.47 |
| 150 | 3.4 |
| 151 | 6.1 |

The compounds of the invention are additionally tested in a human whole blood (HWB) assay to determine their ability to inhibit the synthesis of LTB4 in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB4 concentrations are then measured using an antibody-based homogenous time-resolved fluorescence method (CisBio, Bedford, Mass.). In general, the preferred potency range (IC50) of compounds in the HWB assay is between 10 nM to 10 μM, the more preferred potency range is 10 nM to 1 μM, and the most preferred potency range is 10 nM to 100 nM. The potencies of representative compounds of the invention in the WHB assays are shown in Table 4.

TABLE 4

IC50 values of LTB4 production inhibition assay in human whole blood.

| Ex. | hWB IC$_{50}$ (nM) |
|---|---|
| 1 | 140 |
| 2 | 210 |
| 3 | 200 |
| 4 | 160 |
| 5 | 130 |
| 6 | 130 |
| 7 | 120 |
| 8 | 230 |
| 9 | 170 |
| 10 | 150 |
| 11 | 110 |
| 12 | 120 |
| 13 | 290 |
| 14 | 190 |
| 15 | 190 |
| 16 | 160 |
| 17 | 160 |
| 18 | 160 |
| 19 | 140 |
| 20 | 150 |
| 21 | 100 |
| 22 | 130 |
| 23 | 170 |
| 24 | 290 |
| 25 | 520 |
| 26 | 240 |
| 27 | 200 |
| 28 | 270 |
| 29 | 220 |
| 30 | 230 |
| 31 | 270 |
| 32 | 180 |
| 33 | 150 |
| 34 | 430 |
| 35 | 950 |
| 36 | 220 |
| 37 | 120 |
| 38 | 180 |
| 39 | 320 |
| 40 | 340 |
| 41 | 430 |
| 42 | 190 |
| 43 | 680 |
| 44 | 870 |
| 45 | 310 |
| 46 | 230 |
| 47 | 210 |
| 48 | 610 |
| 49 | 210 |
| 50 | 170 |
| 51 | 210 |
| 52 | 150 |
| 53 | 110 |
| 54 | 190 |
| 55 | 280 |
| 56 | 150 |
| 57 | 98 |
| 58 | 120 |
| 59 | 110 |
| 60 | 110 |
| 61 | 220 |
| 62 | 340 |
| 63 | 190 |
| 64 | 150 |
| 65 | 560 |
| 66 | 430 |
| 67 | 550 |
| 68 | 270 |
| 69 | 210 |
| 70 | 290 |
| 71 | 490 |
| 72 | 160 |
| 73 | 220 |
| 74 | 350 |
| 75 | 250 |
| 76 | 360 |
| 77 | 170 |
| 78 | 190 |
| 79 | 280 |
| 80 | 200 |
| 81 | 580 |
| 82 | 410 |
| 83 | 240 |
| 84 | 450 |
| 85 | 310 |
| 86 | 240 |
| 87 | 260 |
| 88 | 410 |
| 89 | 470 |
| 90 | 640 |
| 91 | 930 |
| 92 | 470 |
| 93 | 530 |
| 94 | 350 |
| 95 | 280 |
| 96 | 990 |
| 97 | 210 |
| 98 | 120 |
| 99 | 140 |
| 100 | 170 |
| 101 | 230 |
| 102 | 150 |
| 103 | 170 |
| 104 | 150 |
| 105 | 210 |
| 106 | 120 |
| 107 | 210 |
| 108 | 180 |
| 109 | 140 |
| 110 | 130 |
| 111 | 170 |
| 112 | 350 |
| 113 | 160 |
| 114 | 150 |
| 115 | 120 |
| 116 | 240 |
| 117 | 670 |
| 118 | 170 |
| 119 | 1200 |
| 120 | 700 |
| 121 | 620 |
| 122 | 570 |
| 123 | 200 |
| 124 | 420 |
| 125 | 340 |
| 126 | 250 |
| 127 | 320 |
| 128 | 240 |
| 129 | 180 |
| 130 | 630 |
| 131 | 360 |
| 132 | 630 |
| 133 | 320 |
| 134 | 410 |
| 135 | 610 |
| 136 | 770 |
| 137 | 440 |
| 138 | 340 |
| 139 | 500 |

TABLE 4-continued

IC50 values of LTB4 production inhibition
assay in human whole blood.

| Ex. | hWB IC$_{50}$ (nM) |
|---|---|
| 140 | 150 |
| 141 | 400 |
| 142 | 930 |
| 143 | 580 |
| 144 | 660 |
| 145 | 510 |
| 146 | 750 |
| 148 | 1100 |
| 149 | 200 |
| 150 | 490 |
| 151 | 800 |

Methods of Use

The compounds of the invention are effective inhibitors of leukotriene A$_4$ hydrolase (LTA$_4$H) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

In one embodiment, the invention relates to the use of a compound of the invention for the preparation of a medicament for the treatment leukotriene-mediated disorders. In another embodiment, the invention relates to the use of a compound of the invention, for the preparation of a medicament for treating cardiovascular, inflammatory, allergic, pulmonary and fibrotic diseases, renal diseases and cancer.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

Without wishing to be bound by theory, by inhibiting the activity of LTA$_4$H, the compounds of the invention block the production of LTB$_4$ resulting from the oxidation of arachidonic acid by 5-LO and subsequent metabolism. Thus, the inhibition of LTA$_4$H activity is an attractive means for preventing and treating a variety of diseases mediated by LTB$_4$. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, inflammatory and allergic ocular diseases, atopic dermatitis, allergy, asthma, autoimmune diseases, Crohn's disease, cystic fibrosis, diabetic nephropathy, diabetic retinopathy, ulcerative colitis, and steatohepatitis;

Cancer including solid tumors, leukemias and lymphomas; and Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical*

*Dosage Forms and Drug Delivery Systems,* 5th ed., Lea and Febiger, 1990; each of which is incorporated herein by reference in their entireties to better describe the state of the art.

Combination Therapy

The compounds of the invention may be administered alone or in combination with at least one additional active agent. Thus, in one embodiment, the invention relates to a pharmaceutical composition comprising one or more compounds of the invention in combination with at least one additional agent. In another embodiment, the invention relates a method of treating diseases mediated by $LTB_4$, the method comprising administering a therapeutically effective amount of one or more compounds of the invention in combination with a pharmaceutically effective amount of at least one additional agent.

Nonlimiting examples of additional active agents include statins (or HMG-CoA reductase inhibitors); cholesterol ester transfer protein (CETP) inhibitors (or antagonists); fibrates, niacin derivatives, Lp-PLA2-inhibitors (e.g., darapladib, varespladib), antiplatelets and anticoagulants.

In one embodiment, the additional active agent is a statin. In another embodiment, the additional active agent is a statin selected from the group consisting of atorvastatin, fluvastatin, lovastatin, pitavastatin, pravastatin, rosuvastatin, and simvastatin.

In one embodiment, the additional active agent is a CETP inhibitor. In another embodiment, the additional active agent is a CETP inhibitor selected from the group consisting of anacetrapib, dalcetrapib, evacetrapib, TA-8995 (Mitsubishi Tanabe Pharma), ATH-03 (Affris), DRL-17822 (Dr. Reddy's). In yet another embodiment, the additional active is selected from the group consisting of dalcetrapib and anacetrapib.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound selected from the group consisting of:
1-{6-[5-(2H-Pyrazol-3-yl)-pyridin-2-yloxy]-naphthalen-2-ylmethyl}-azetidin-3-ol;
1-{6-[5-(2H-Pyrazol-3-yl)-pyridin-2-yloxy]-naphthalen-2-ylmethyl}-azetidine-3-carboxylic acid amide;
N-(1-{6-[5-(2H-Pyrazol-3-yl)-pyridin-2-yloxy]-naphthalen-2-ylmethyl}-azetidin-3-yl)-acetamide;
(1-{6-[5-(2H-Pyrazol-3-yl)-pyridin-2-yloxy]-naphthalen-2-ylmethyl}-azetidin-3-yl)-methanol;
(S)-1-{6-[5-(2H-Pyrazol-3-yl)-pyridin-2-yloxy]-naphthalen-2-ylmethyl}-pyrrolidin-3-ol;
(R)-1-{6-[5-(2H-Pyrazol-3-yl)-pyridin-2-yloxy]-naphthalen-2-ylmethyl}-pyrrolidin-3-ol;
2-Hydroxy-1-(4-{6-[5-(2H-pyrazol-3-yl)-pyridin-2-yloxy]-naphthalen-2-ylmethyl}-piperazin-1-yl)-ethanone;
(S)-3-Hydroxy-1-(1-{6-[5-(2H-pyrazol-3-yl)-pyridin-2-yloxy]-quinolin-2-ylmethyl}-piperidin-4-yl)-pyrrolidin-2-one;
2-Hydroxy-N-(1-{6-[5-(2H-pyrazol-3-yl)-pyridin-2-yloxy]-naphthalen-2-ylmethyl}-piperidin-4-yl)-acetamide;
2-{6-[5-(2H-Pyrazol-3-yl)-pyridin-2-yloxy]-naphthalen-2-ylmethyl}-2-aza-spiro[3.3]heptan-6-ol;
3-Methyl-1-{6-[5-(2H-pyrazol-3-yl)-pyridin-2-yloxy]-naphthalen-2-ylmethyl}-azetidin-3-ol;
N-((R)-1-{6-[5-(2H-Pyrazol-3-yl)-pyridin-2-yloxy]-naphthalen-2-ylmethyl}-pyrrolidin-3-yl)-acetamide;
N-((S)-1-{6-[5-(2H-Pyrazol-3-yl)-pyridin-2-yloxy]-naphthalen-2-ylmethyl}-pyrrolidin-3-yl)-acetamide;
(S)-1-{6-[5-(2H-Pyrazol-3-yl)-pyridin-2-yloxy]-naphthalen-2-ylmethyl}-piperidin-3-ol;
(R)-1-{6-[5-(2H-Pyrazol-3-yl)-pyridin-2-yloxy]-naphthalen-2-ylmethyl}-piperidin-3-ol;
2-(Methyl-{6-[5-(2H-pyrazol-3-yl)-pyridin-2-yloxy]-naphthalen-2-ylmethyl}-amino)-ethanol;
(1-{6-[5-(2H-Pyrazol-3-yl)-pyridin-2-yloxy]-naphthalen-2-ylmethyl}-piperidin-4-yl)-methanol;
((S)-1-{6-[5-(2H-Pyrazol-3-yl)-pyridin-2-yloxy]-naphthalen-2-ylmethyl}-pyrrolidin-3-yl)-methanol;
2-Hydroxy-1-[(R)-3-(methyl-{6-[5-(2H-pyrazol-3-yl)-pyridin-2-yloxy]-naphthalen-2-ylmethyl}-amino)-pyrrolidin-1-yl]-ethanone;
2-Hydroxy-N-methyl-N-((S)-1-{6-[5-(2H-pyrazol-3-yl)-pyridin-2-yloxy]-naphthalen-2-ylmethyl}-pyrrolidin-3-yl)-acetamide;
2-Hydroxy-N-methyl-N-((R)-1-{6-[5-(2H-pyrazol-3-yl)-pyridin-2-yloxy]-naphthalen-2-ylmethyl}-pyrrolidin-3-yl)-acetamide;
((R)-1-{6-[5-(2H-Pyrazol-3-yl)-pyridin-2-yloxy]-naphthalen-2-ylmethyl}-pyrrolidin-3-yl)-methanol;
2-Hydroxy-1-[(S)-3-(methyl-{6-[5-(2H-pyrazol-3-yl)-pyridin-2-yloxy]-naphthalen-2-ylmethyl}-amino)-pyrrolidin-1-yl]-ethanone;
2-Methoxy-1-(4-{6-[5-(2H-pyrazol-3-yl)-pyrimidin-2-yloxy]-naphthalen-2-ylmethyl}-piperazin-1-yl)-ethanone;
1-(4-{6-[5-(2H-Pyrazol-3-yl)-pyrimidin-2-yloxy]-naphthalen-2-ylmethyl}-piperazin-1-yl)-ethanone;
1-{6-[5-(2H-Pyrazol-3-yl)-pyrimidin-2-yloxy]-naphthalen-2-ylmethyl}-piperidin-4-ol;
1-{6-[5-(2H-Pyrazol-3-yl)-pyrimidin-2-yloxy]-naphthalen-2-ylmethyl}-piperidine-4-carboxylic acid amide;
N-(1-{6-[5-(2H-Pyrazol-3-yl)-pyrimidin-2-yloxy]-naphthalen-2-ylmethyl}-piperidin-4-yl)-acetamide;
(S)-3-Hydroxy-1-(1-{6-[5-(2H-pyrazol-3-yl)-pyrimidin-2-yloxy]-naphthalen-2-ylmethyl}-piperidin-4-yl)-pyrrolidin-2-one;
(S)-2-Hydroxy-1-(4-{6-[5-(2H-pyrazol-3-yl)-pyrimidin-2-yloxy]-naphthalen-2-ylmethyl}-piperazin-1-yl)-propan-1-one;
2-Hydroxy-N-methyl-N-(1-{6-[5-(2H-pyrazol-3-yl)-pyrimidin-2-yloxy]-naphthalen-2-ylmethyl}-piperidin-4-yl)-acetamide;
1-{3-[(Methyl-{6-[5-(2H-pyrazol-3-yl)-pyrimidin-2-yloxy]-naphthalen-2-ylmethyl}-amino)-methyl]-azetidin-1-yl}-ethanone;
3-(1-{6-[5-(2H-Pyrazol-3-yl)-pyrimidin-2-yloxy]-naphthalen-2-ylmethyl}-piperidin-4-yl)-oxazolidin-2-one;
4-{6-[5-(2H-Pyrazol-3-yl)-pyrimidin-2-yloxy]-naphthalen-2-ylmethyl}-piperazine-1-carboxylic acid dimethylamide;
2,2-Dimethyl-1-(4-{6-[5-(2H-pyrazol-3-yl)-pyrimidin-2-yloxy]-naphthalen-2-ylmethyl}-piperazin-1-yl)-propan-1-one;
1-(1-{6-[5-(2H-Pyrazol-3-yl)-pyrimidin-2-yloxy]-naphthalen-2-ylmethyl}-piperidin-4-yl)-pyrrolidin-2-one;
1-(4-{6-[5-(2H-Pyrazol-3-yl)-pyrimidin-2-yloxy]-naphthalen-2-ylmethyl}-piperazin-1-yl)-propan-1-one;

1-{6-[5-(2H-Pyrazol-3-yl)-pyrimidin-2-yloxy]-naphthalen-2-ylmethyl}-piperidine-4-carboxylic acid dimethylamide;
2-Hydroxy-2-methyl-1-(4-{6-[5-(2H-pyrazol-3-yl)-pyrimidin-2-yloxy]-naphthalen-2-ylmethyl}-piperazin-1-yl)-propan-1-one;
Cyclopropyl-(4-{6-[5-(2H-pyrazol-3-yl)-pyrimidin-2-yloxy]-naphthalen-2-ylmethyl}-piperazin-1-yl)-methanone;
2-Methyl-1-(4-{6-[5-(2H-pyrazol-3-yl)-pyrimidin-2-yloxy]-naphthalen-2-ylmethyl}-piperazin-1-yl)-propan-1-one;
1-{6-[5-(2H-Pyrazol-3-yl)-pyridin-2-yloxy]-quinolin-2-ylmethyl}-azetidin-3-ol;
3-({6-[5-(2H-Pyrazol-3-yl)-pyridin-2-yloxy]-quinolin-2-ylmethyl}-amino)-propionitrile;
(R)-3-({6-[5-(2H-Pyrazol-3-yl)-pyridin-2-yloxy]-quinolin-2-ylmethyl}-amino)-pentanenitrile;
(R)-1-{6-[5-(2H-Pyrazol-3-yl)-pyrimidin-2-yloxy]-naphthalen-2-ylmethyl}-pyrrolidin-3-ol;
(S)-1-{6-[5-(2H-Pyrazol-3-yl)-pyrimidin-2-yloxy]-naphthalen-2-ylmethyl}-pyrrolidin-3-ol;
3-Methyl-1-{6-[5-(2H-pyrazol-3-yl)-pyrimidin-2-yloxy]-naphthalen-2-ylmethyl}-azetidin-3-ol;
2-Hydroxy-1-(4-{6-[5-(2H-pyrazol-3-yl)-pyrimidin-2-yloxy]-naphthalen-2-ylmethyl}-piperazin-1-yl)-ethanone;
1-{6-[5-(2H-Pyrazol-3-yl)-pyrimidin-2-yloxy]-naphthalen-2-ylmethyl}-azetidin-3-ol;
3-Oxo-3-(8-{6-[5-(2H-pyrazol-3-yl)-pyridin-2-yloxy]-quinolin-2-ylmethyl}-3,8-diaza-bicyclo[3.2.1]oct-3-yl)-propionitrile;
2,2-Dimethyl-3-oxo-3-(8-{6-[5-(2H-pyrazol-3-yl)-pyridin-2-yloxy]-quinolin-2-ylmethyl}-3,8-diaza-bicyclo[3.2.1]oct-3-yl)-propionitrile;
(R)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(S)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(8-{6-[5-(2H-Pyrazol-3-yl)-pyridin-2-yloxy]-quinolin-2-ylmethyl}-3,8-diaza-bicyclo[3.2.1]oct-3-yl)-(R)-tetrahydro-furan-2-yl-methanone;
(8-{6-[5-(2H-Pyrazol-3-yl)-pyridin-2-yloxy]-quinolin-2-ylmethyl}-3,8-diaza-bicyclo[3.2.1]oct-3-yl)-(S)-tetrahydro-furan-2-yl-methanone;
(1-Hydroxy-cyclopropyl)-(8-{6-[5-(2H-pyrazol-3-yl)-pyridin-2-yloxy]-quinolin-2-ylmethyl}-3,8-diaza-bicyclo[3.2.1]oct-3-yl)-methanone;
(S)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
2-Hydroxy-2-methyl-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(R)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone;
(S)-3-Hydroxy-1-(1-{(S)-6-[5-(2H-pyrazol-3-yl)-pyridin-2-yloxy]-2,3-dihydro-benzofuran-2-ylmethyl}-piperidin-4-yl)-pyrrolidin-2-one;
(S)-3-Hydroxy-1-(1-{(R)-6-[5-(2H-pyrazol-3-yl)-pyridin-2-yloxy]-2,3-dihydro-benzofuran-2-ylmethyl}-piperidin-4-yl)-pyrrolidin-2-one;
1-(1-{(R)-6-[5-(2H-Pyrazol-3-yl)-pyridin-2-yloxy]-2,3-dihydro-benzofuran-2-ylmethyl}-piperidin-4-yl)-pyrrolidin-2-one;
1-(1-{(S)-6-[5-(2H-Pyrazol-3-yl)-pyridin-2-yloxy]-2,3-dihydro-benzofuran-2-ylmethyl}-piperidin-4-yl)-pyrrolidin-2-one;
2-Hydroxy-1-(4-{6-[5-(2H-pyrazol-3-yl)-pyridin-2-yloxy]-2,3-dihydro-benzofuran-2-ylmethyl}-piperazin-1-yl)-ethanone;
2-(4-Methanesulfonyl-piperazin-1-ylmethyl)-6-[5-(2H-pyrazol-3-yl)-pyridin-2-yloxy]-quinoline;
2-(4-Ethanesulfonyl-piperazin-1-ylmethyl)-6-[5-(2H-pyrazol-3-yl)-pyridin-2-yloxy]-quinoline;
1-[1-(2-{6-[5-(2H-Pyrazol-3-yl)-pyridin-2-yloxy]-2,3-dihydro-benzofuran-3-yl}-ethyl)-piperidin-4-yl]-pyrrolidin-2-one;
3-[1-(2-{6-[5-(2H-Pyrazol-3-yl)-pyridin-2-yloxy]-2,3-dihydro-benzofuran-3-yl}-ethyl)-piperidin-4-yl]-oxazolidin-2-one;
(S)-3-Hydroxy-1-[1-(2-{6-[5-(2H-pyrazol-3-yl)-pyridin-2-yloxy]-2,3-dihydro-benzofuran-3-yl}-ethyl)-piperidin-4-yl]-pyrrolidin-2-one;
1-Methanesulfonyl-4-(2-{6-[5-(2H-pyrazol-3-yl)-pyridin-2-yloxy]-2,3-dihydro-benzofuran-3-yl}-ethyl)-piperazine;
1-[1-(2-{6-[5-(2H-Pyrazol-3-yl)-pyridin-2-yloxy]-benzofuran-3-yl}-ethyl)-piperidin-4-yl]-pyrrolidin-2-one;
(S)-3-Hydroxy-1-[1-(2-{6-[5-(2H-pyrazol-3-yl)-pyridin-2-yloxy]-benzofuran-3-yl}-ethyl)-piperidin-4-yl]-pyrrolidin-2-one;
1-Methanesulfonyl-4-(2-{6-[5-(2H-pyrazol-3-yl)-pyridin-2-yloxy]-benzofuran-3-yl}-ethyl)-piperazine;
(S)-2-Methoxy-1-[4-(2-{6-[5-(2H-pyrazol-3-yl)-pyridin-2-yloxy]-benzofuran-3-yl}-ethyl)-piperazin-1-yl]-propan-1-one;
(R)-2-Methoxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one;
2-Methoxy-1-[4-(2-{6-[5-(2H-pyrazol-3-yl)-pyridin-2-yloxy]-benzofuran-3-yl}-ethyl)-piperazin-1-yl]-ethanone;
(R)-2-Methoxy-1-[4-(2-{6-[5-(2H-pyrazol-3-yl)-pyridin-2-yloxy]-benzofuran-3-yl}-ethyl)-piperazin-1-yl]-propan-1-one;
(S)-2-Methoxy-1-(4-{6-[4-(2H-pyrazol-3-yl)-phenoxy]-imidazo[1,2-a]pyridin-2-ylmethyl}-piperazin-1-yl)-propan-1-one;
(R)-2-Methoxy-1-(4-{6-[4-(2H-pyrazol-3-yl)-phenoxy]-imidazo[1,2-a]pyridin-2-ylmethyl}-piperazin-1-yl)-propan-1-one;
2-Hydroxy-2-methyl-1-[4-(2-{6-[5-(2H-pyrazol-3-yl)-pyridin-2-yloxy]-2,3-dihydro-benzofuran-3-yl}-ethyl)-piperazin-1-yl]-propan-1-one;
2-Hydroxy-1-[4-(2-{6-[5-(2H-pyrazol-3-yl)-pyridin-2-yloxy]-benzofuran-3-yl}-ethyl)-piperazin-1-yl]-ethanone;
(S)-2-Hydroxy-1-[4-(2-{6-[5-(2H-pyrazol-3-yl)-pyridin-2-yloxy]-benzofuran-3-yl}-ethyl)-piperazin-1-yl]-propan-1-one;
(S)-2-Hydroxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one;

2-Hydroxy-2-methyl-1-[4-(2-{6-[5-(2H-pyrazol-3-yl)-pyridin-2-yloxy]-benzofuran-3-yl}-ethyl)-piperazin-1-yl]-propan-1-one;
2-Hydroxy-1-(4-{6-[4-(2H-pyrazol-3-yl)-phenoxy]-imidazo[1,2-a]pyridin-2-ylmethyl}-piperazin-1-yl)-ethanone;
(S)-2-Hydroxy-1-(4-{6-[4-(2H-pyrazol-3-yl)-phenoxy]-imidazo[1,2-a]pyridin-2-ylmethyl}-piperazin-1-yl)-propan-1-one;
(S)-2-Methoxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one;
2-Methoxy-1-(4-{6-[4-(2H-pyrazol-3-yl)-phenoxy]-imidazo[1,2-a]pyridin-2-ylmethyl}-piperazin-1-yl)-ethanone;
(1-Hydroxy-cyclopropyl)-[4-(2-{6-[5-(2H-pyrazol-3-yl)-pyridin-2-yloxy]-2,3-dihydro-benzofuran-3-yl}-ethyl)-piperazin-1-yl]-methanone;
(R)-2-Hydroxy-1-[4-(2-{6-[5-(2H-pyrazol-3-yl)-pyridin-2-yloxy]-2,3-dihydro-benzofuran-3-yl}-ethyl)-piperazin-1-yl]-propan-1-one;
(R)-2-Hydroxy-1-[4-(2-{6-[5-(2H-pyrazol-3-yl)-pyridin-2-yloxy]-benzofuran-3-yl}-ethyl)-piperazin-1-yl]-propan-1-one;
(1-Hydroxy-cyclopropyl)-[4-(2-{6-[5-(2H-pyrazol-3-yl)-pyridin-2-yloxy]-benzofuran-3-yl}-ethyl)-piperazin-1-yl]-methanone;
(R)-2-Hydroxy-1-(4-{6-[4-(2H-pyrazol-3-yl)-phenoxy]-imidazo[1,2-a]pyridin-2-ylmethyl}-piperazin-1-yl)-propan-1-one;
1-(4-{6-[4-(2H-Pyrazol-3-yl)-phenoxy]-imidazo[1,2-a]pyridin-2-ylmethyl}-piperazin-1-yl)-ethanone;
(1-Hydroxy-cyclopropyl)-(4-{6-[4-(2H-pyrazol-3-yl)-phenoxy]-imidazo[1,2-a]pyridin-2-ylmethyl}-piperazin-1-yl)-methanone;
1-(4-{6-[5-(2H-Pyrazol-3-yl)-pyridin-2-yloxy]-benzofuran-3-ylmethyl}-[1,4]diazepan-1-yl)-ethanone;
2-Hydroxy-N-methyl-N-((R)-1-{6-[5-(2H-pyrazol-3-yl)-pyridin-2-yloxy]-quinolin-2-ylmethyl}-pyrrolidin-3-yl)-acetamide;
2-Hydroxy-N-methyl-N-((S)-1-{6-[5-(2H-pyrazol-3-yl)-pyridin-2-yloxy]-quinolin-2-ylmethyl}-pyrrolidin-3-yl)-acetamide;
2-Hydroxy-1-[(R)-3-(methyl-{6-[5-(2H-pyrazol-3-yl)-pyridin-2-yloxy]-quinolin-2-ylmethyl}-amino)-pyrrolidin-1-yl]-ethanone;
2-Hydroxy-1-[(S)-3-(methyl-{6-[5-(2H-pyrazol-3-yl)-pyridin-2-yloxy]-quinolin-2-ylmethyl}-amino)-pyrrolidin-1-yl]-ethanone;
2-Hydroxy-1-(7-{6-[5-(2H-pyrazol-3-yl)-pyridin-2-yloxy]-quinolin-2-ylmethyl}-2,7-diaza-spiro[4.4]non-2-yl)-ethanone;
1-{6-[5-(2H-Pyrazol-3-yl)-pyridin-2-yloxy]-benzofuran-3-ylmethyl}-piperidine-4-carboxylic acid methylamide;
N-(1-{6-[5-(2H-Pyrazol-3-yl)-pyridin-2-yloxy]-benzofuran-3-ylmethyl}-piperidin-4-yl)-acetamide;
N-(1-{6-[5-(2H-Pyrazol-3-yl)-pyridin-2-yloxy]-benzofuran-3-ylmethyl}-piperidin-4-yl)-methanesulfonamide;
N-(1-{6-[5-(2H-Pyrazol-3-yl)-pyridin-2-yloxy]-benzofuran-3-ylmethyl}-piperidin-4-ylmethyl)-acetamide;
1-{4-[({6-[5-(2H-Pyrazol-3-yl)-pyridin-2-yloxy]-benzofuran-3-ylmethyl}-amino)-methyl]-piperidin-1-yl}-ethanone;
1-[4-({6-[5-(2H-Pyrazol-3-yl)-pyridin-2-yloxy]-benzofuran-3-ylmethyl}-amino)-piperidin-1-yl]-ethanone;
(S)-3-Hydroxy-1-(1-{6-[5-(2H-pyrazol-3-yl)-pyridin-2-yloxy]-benzofuran-3-ylmethyl}-piperidin-4-yl)-pyrrolidin-2-one;
2-Methyl-8-{6-[5-(2H-pyrazol-3-yl)-pyridin-2-yloxy]-benzofuran-3-ylmethyl}-2,8-diaza-spiro[4.5]decan-1-one;
2-(4-{6-[5-(2H-Pyrazol-3-yl)-pyridin-2-yloxy]-benzofuran-3-ylmethyl}-piperazin-1-yl)-1-pyrrolidin-1-yl-ethanone;
1-(4-{6-[5-(2H-Pyrazol-3-yl)-pyridin-2-yloxy]-benzofuran-3-carbonyl}-piperazin-1-yl)-ethanone;
2-Hydroxy-N-methyl-N-((R)-1-{6-[5-(2H-pyrazol-3-yl)-pyridin-2-yloxy]-benzofuran-3-ylmethyl}-pyrrolidin-3-yl)-acetamide;
2-Hydroxy-N-methyl-N-((S)-1-{6-[5-(2H-pyrazol-3-yl)-pyridin-2-yloxy]-benzofuran-3-ylmethyl}-pyrrolidin-3-yl)-acetamide;
2-Hydroxy-1-(7-{6-[5-(2H-pyrazol-3-yl)-pyridin-2-yloxy]-benzofuran-3-ylmethyl}-2,7-diaza-spiro[4.4]non-2-yl)-ethanone;
1-(4-{6-[5-(2H-Pyrazol-3-yl)-pyridin-2-yloxy]-quinolin-2-ylmethyl}-piperazine-1-carbonyl)-cyclopropanecarbonitrile;
(S)-3-Hydroxy-1-(4-{6-[5-(2H-pyrazol-3-yl)-pyridin-2-yloxy]-quinolin-2-ylmethyl}-piperazin-1-yl)-butan-1-one;
(S)-2-Methoxy-1-(4-{6-[5-(2H-pyrazol-3-yl)-pyridin-2-yloxy]-quinolin-2-ylmethyl}-piperazin-1-yl)-propan-1-one;
(1-Hydroxy-cyclopentyl)-(4-{6-[5-(2H-pyrazol-3-yl)-pyridin-2-yloxy]-quinolin-2-ylmethyl}-piperazin-1-yl)-methanone;
(R)-2-Hydroxy-3-methyl-1-(4-{6-[5-(2H-pyrazol-3-yl)-pyridin-2-yloxy]-quinolin-2-ylmethyl}-piperazin-1-yl)-butan-1-one;
(R)-3-Hydroxy-1-(4-{6-[5-(2H-pyrazol-3-yl)-pyridin-2-yloxy]-quinolin-2-ylmethyl}-piperazin-1-yl)-butan-1-one;
3-Hydroxy-3-methyl-1-(4-{6-[5-(2H-pyrazol-3-yl)-pyridin-2-yloxy]-quinolin-2-ylmethyl}-piperazin-1-yl)-butan-1-one;
(R)-2-Hydroxy-1-(4-{6-[5-(2H-pyrazol-3-yl)-pyridin-2-yloxy]-quinolin-2-ylmethyl}-piperazin-1-yl)-propan-1-one;
2-Ethoxy-1-(4-{6-[5-(2H-pyrazol-3-yl)-pyridin-2-yloxy]-quinolin-2-ylmethyl}-piperazin-1-yl)-ethanone;
2-Hydroxy-2-methyl-1-(4-{6-[5-(2H-pyrazol-3-yl)-pyridin-2-yloxy]-quinolin-2-ylmethyl}-piperazin-1-yl)-propan-1-one;
(1-Hydroxy-cyclopropyl)-(4-{6-[5-(2H-pyrazol-3-yl)-pyridin-2-yloxy]-quinolin-2-ylmethyl}-piperazin-1-yl)-methanone;
(S)-2-Hydroxy-1-(4-{6-[5-(2H-pyrazol-3-yl)-pyridin-2-yloxy]-quinolin-2-ylmethyl}-piperazin-1-yl)-butan-1-one;
2-Methoxy-2-methyl-1-(4-{6-[5-(2H-pyrazol-3-yl)-pyridin-2-yloxy]-quinolin-2-ylmethyl}-piperazin-1-yl)-propan-1-one;
(S)-2-Hydroxy-1-(4-{6-[5-(2H-pyrazol-3-yl)-pyridin-2-yloxy]-quinolin-2-ylmethyl}-piperazin-1-yl)-propan-1-one;
2-Isopropoxy-1-(4-{6-[5-(2H-pyrazol-3-yl)-pyridin-2-yloxy]-quinolin-2-ylmethyl}-piperazin-1-yl)-ethanone;

(4-{6-[5-(2H-Pyrazol-3-yl)-pyridin-2-yloxy]-quinolin-2-ylmethyl}-piperazin-1-yl)-(tetrahydro-pyran-4-yl)-methanone;
(4-{6-[5-(2H-Pyrazol-3-yl)-pyridin-2-yloxy]-quinolin-2-ylmethyl}-piperazin-1-yl)-(S)-tetrahydro-furan-2-yl-methanone;
(4-{6-[5-(2H-Pyrazol-3-yl)-pyridin-2-yloxy]-quinolin-2-ylmethyl}-piperazin-1-yl)-(R)-tetrahydro-furan-2-yl-methanone;
(R)-2-Hydroxy-1-(4-{6-[5-(2H-pyrazol-3-yl)-pyridin-2-yloxy]-quinolin-2-ylmethyl}-piperazin-1-yl)-butan-1-one;
3-Hydroxy-2,2-dimethyl-1-(4-{6-[5-(2H-pyrazol-3-yl)-pyridin-2-yloxy]-quinolin-2-ylmethyl}-piperazin-1-yl)-propan-1-one;
(3-Oxa-bicyclo[3.1.0]hex-6-yl)-(4-{6-[5-(2H-pyrazol-3-yl)-pyridin-2-yloxy]-quinolin-2-ylmethyl}-piperazin-1-yl)-methanone;
(S)-2-Hydroxy-3-methyl-1-(4-{6-[5-(2H-pyrazol-3-yl)-pyridin-2-yloxy]-quinolin-2-ylmethyl}-piperazin-1-yl)-butan-1-one;
(1-Hydroxymethyl-cyclopropyl)-(4-{6-[5-(2H-pyrazol-3-yl)-pyridin-2-yloxy]-quinolin-2-ylmethyl}-piperazin-1-yl)-methanone;
(3-Hydroxy-cyclobutyl)-(4-{6-[5-(2H-pyrazol-3-yl)-pyridin-2-yloxy]-quinolin-2-ylmethyl}-piperazin-1-yl)-methanone;
(R)-2-Methoxy-1-(4-{6-[5-(2H-pyrazol-3-yl)-pyridin-2-yloxy]-quinolin-2-ylmethyl}-piperazin-1-yl)-propan-1-one;
(4-{6-[5-(2H-Pyrazol-3-yl)-pyridin-2-yloxy]-quinolin-2-ylmethyl}-piperazin-1-yl)-(R)-tetrahydro-furan-3-yl-methanone;
4-Methoxy-1-(4-{6-[5-(2H-pyrazol-3-yl)-pyridin-2-yloxy]-quinolin-2-ylmethyl}-piperazin-1-yl)-butan-1-one;
(1-Hydroxy-cyclobutyl)-(4-{6-[5-(2H-pyrazol-3-yl)-pyridin-2-yloxy]-quinolin-2-ylmethyl}-piperazin-1-yl)-methanone;
2-Propoxy-1-(4-{6-[5-(2H-pyrazol-3-yl)-pyridin-2-yloxy]-quinolin-2-ylmethyl}-piperazin-1-yl)-ethanone;
2,2-Dimethyl-3-oxo-3-(4-{6-[5-(2H-pyrazol-3-yl)-pyridin-2-yloxy]-quinolin-2-ylmethyl}-piperazin-1-yl)-propionitrile;
1-(4-{6-[5-(2H-Pyrazol-3-yl)-pyridin-2-yloxy]-quinolin-2-ylmethyl}-piperazine-1-carbonyl)-cyclobutanecarbonitrile;
1-(4-{6-[5-(2H-Pyrazol-3-yl)-pyridin-2-yloxy]-quinolin-2-ylmethyl}-piperazine-1-carbonyl)-cyclopentanecarbonitrile;
4-(4-{6-[5-(2H-Pyrazol-3-yl)-pyridin-2-yloxy]-quinolin-2-ylmethyl}-piperazine-1-carbonyl)-tetrahydro-pyran-4-carbonitrile;
2-Methyl-3-oxo-3-(4-{6-[5-(2H-pyrazol-3-yl)-pyridin-2-yloxy]-quinolin-2-ylmethyl}-piperazin-1-yl)-propionitrile;
(3-Hydroxy-3-methyl-cyclobutyl)-(4-{6-[5-(2H-pyrazol-3-yl)-pyridin-2-yloxy]-quinolin-2-ylmethyl}-piperazin-1-yl)-methanone; and
((1R,2S)-2-Hydroxy-cyclopentyl)-(4-{6-[5-(2H-pyrazol-3-yl)-pyridin-2-yloxy]-quinolin-2-ylmethyl}-piperazin-1-yl)-methanone;
2-Methoxy-1-(4-{6-[5-(2H-pyrazol-3-yl)-pyrimidin-2-yloxy]-naphthalen-2-ylmethyl}-piperazin-1-yl)-ethanone;
1-(4-{6-[5-(2H-Pyrazol-3-yl)-pyrimidin-2-yloxy]-naphthalen-2-ylmethyl}-piperazin-1-yl)-ethanone;
1-{6-[5-(2H-Pyrazol-3-yl)-pyrimidin-2-yloxy]-naphthalen-2-ylmethyl}-piperidin-4-ol;
1-{6-[5-(2H-Pyrazol-3-yl)-pyrimidin-2-yloxy]-naphthalen-2-ylmethyl}-piperidine-4-carboxylic acid amide;
N-(1-{6-[5-(2H-Pyrazol-3-yl)-pyrimidin-2-yloxy]-naphthalen-2-ylmethyl}-piperidin-4-yl)-acetamide;
(S)-3-Hydroxy-1-(1-{6-[5-(2H-pyrazol-3-yl)-pyrimidin-2-yloxy]-naphthalen-2-ylmethyl}-piperidin-4-yl)-pyrrolidin-2-one;
(S)-2-Hydroxy-1-(4-{6-[5-(2H-pyrazol-3-yl)-pyrimidin-2-yloxy]-naphthalen-2-ylmethyl}-piperazin-1-yl)-propan-1-one;
2-Hydroxy-N-methyl-N-(1-{6-[5-(2H-pyrazol-3-yl)-pyrimidin-2-yloxy]-naphthalen-2-ylmethyl}-piperidin-4-yl)-acetamide;
1-{3-[(Methyl-{6-[5-(2H-pyrazol-3-yl)-pyrimidin-2-yloxy]-naphthalen-2-ylmethyl}-amino)-methyl]-azetidin-1-yl}-ethanone;
3-(1-{6-[5-(2H-Pyrazol-3-yl)-pyrimidin-2-yloxy]-naphthalen-2-ylmethyl}-piperidin-4-yl)-oxazolidin-2-one;
4-{6-[5-(2H-Pyrazol-3-yl)-pyrimidin-2-yloxy]-naphthalen-2-ylmethyl}-piperazine-1-carboxylic acid dimethylamide;
2,2-Dimethyl-1-(4-{6-[5-(2H-pyrazol-3-yl)-pyrimidin-2-yloxy]-naphthalen-2-ylmethyl}-piperazin-1-yl)-propan-1-one;
1-(1-{6-[5-(2H-Pyrazol-3-yl)-pyrimidin-2-yloxy]-naphthalen-2-ylmethyl}-piperidin-4-yl)-pyrrolidin-2-one;
1-(4-{6-[5-(2H-Pyrazol-3-yl)-pyrimidin-2-yloxy]-naphthalen-2-ylmethyl}-piperazin-1-yl)-propan-1-one;
1-{6-[5-(2H-Pyrazol-3-yl)-pyrimidin-2-yloxy]-naphthalen-2-ylmethyl}-piperidine-4-carboxylic acid dimethylamide;
2-Hydroxy-2-methyl-1-(4-{6-[5-(2H-pyrazol-3-yl)-pyrimidin-2-yloxy]-naphthalen-2-ylmethyl}-piperazin-1-yl)-propan-1-one;
Cyclopropyl-(4-{6-[5-(2H-pyrazol-3-yl)-pyrimidin-2-yloxy]-naphthalen-2-ylmethyl}-piperazin-1-yl)-methanone;
2-Methyl-1-(4-{6-[5-(2H-pyrazol-3-yl)-pyrimidin-2-yloxy]-naphthalen-2-ylmethyl}-piperazin-1-yl)-propan-1-one;
(R)-1-{6-[5-(2H-Pyrazol-3-yl)-pyrimidin-2-yloxy]-naphthalen-2-ylmethyl}-pyrrolidin-3-ol;
(S)-1-{6-[5-(2H-Pyrazol-3-yl)-pyrimidin-2-yloxy]-naphthalen-2-ylmethyl}-pyrrolidin-3-ol;
3-Methyl-1-{6-[5-(2H-pyrazol-3-yl)-pyrimidin-2-yloxy]-naphthalen-2-ylmethyl}-azetidin-3-ol;
2-Hydroxy-1-(4-{6-[5-(2H-pyrazol-3-yl)-pyrimidin-2-yloxy]-naphthalen-2-ylmethyl}-piperazin-1-yl)-ethanone; and
1-{6-[5-(2H-Pyrazol-3-yl)-pyrimidin-2-yloxy]-naphthalen-2-ylmethyl}-azetidin-3-ol;
(S)-3-Hydroxy-1-(1-{6-[5-(2H-pyrazol-3-yl)-pyridin-2-yloxy]-quinolin-2-ylmethyl}-piperidin-4-yl)-pyrrolidin-2-one;
(R)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(S)-2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(S)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;

2-Hydroxy-2-methyl-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
(R)-2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-propan-1-one;
2-Methoxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone;
2-Hydroxy-N-methyl-N-((R)-1-{6-[5-(2H-pyrazol-3-yl)-pyridin-2-yloxy]-quinolin-2-ylmethyl}-pyrrolidin-3-yl)-acetamide;
2-Hydroxy-N-methyl-N-((S)-1-{6-[5-(2H-pyrazol-3-yl)-pyridin-2-yloxy]-quinolin-2-ylmethyl}-pyrrolidin-3-yl)-acetamide;
2-Hydroxy-1-[(R)-3-(methyl-{6-[5-(2H-pyrazol-3-yl)-pyridin-2-yloxy]-quinolin-2-ylmethyl}-amino)-pyrrolidin-1-yl]-ethanone;
2-Hydroxy-1-[(S)-3-(methyl-{6-[5-(2H-pyrazol-3-yl)-pyridin-2-yloxy]-quinolin-2-ylmethyl}-amino)-pyrrolidin-1-yl]-ethanone;
2-Hydroxy-1-(7-{6-[5-(2H-pyrazol-3-yl)-pyridin-2-yloxy]-quinolin-2-ylmethyl}-2,7-diaza-spiro[4.4]non-2-yl)-ethanone;
(S)-2-Methoxy-1-(4-{6-[5-(2H-pyrazol-3-yl)-pyridin-2-yloxy]-quinolin-2-ylmethyl}-piperazin-1-yl)-propan-1-one;
(R)-2-Hydroxy-1-(4-{6-[5-(2H-pyrazol-3-yl)-pyridin-2-yloxy]-quinolin-2-ylmethyl}-piperazin-1-yl)-propan-1-one;
(1-Hydroxy-cyclopropyl)-(4-{6-[5-(2H-pyrazol-3-yl)-pyridin-2-yloxy]-quinolin-2-ylmethyl}-piperazin-1-yl)-methanone;
2-Methoxy-2-methyl-1-(4-{6-[5-(2H-pyrazol-3-yl)-pyridin-2-yloxy]-quinolin-2-ylmethyl}-piperazin-1-yl)-propan-1-one;
(S)-2-Hydroxy-1-(4-{6-[5-(2H-pyrazol-3-yl)-pyridin-2-yloxy]-quinolin-2-ylmethyl}-piperazin-1-yl)-propan-1-one;
(R)-2-Methoxy-1-(4-{6-[5-(2H-pyrazol-3-yl)-pyridin-2-yloxy]-quinolin-2-ylmethyl}-piperazin-1-yl)-propan-1-one; and
2-Methyl-3-oxo-3-(4-{6-[5-(2H-pyrazol-3-yl)-pyridin-2-yloxy]-quinolin-2-ylmethyl}-piperazin-1-yl)-propionitrile;
1-{6-[5-(2H-Pyrazol-3-yl)-pyridin-2-yloxy]-naphthalen-2-ylmethyl}-azetidin-3-ol;
1-{6-[5-(2H-Pyrazol-3-yl)-pyridin-2-yloxy]-naphthalen-2-ylmethyl}-azetidine-3-carboxylic acid amide;
N-(1-{6-[5-(2H-Pyrazol-3-yl)-pyridin-2-yloxy]-naphthalen-2-ylmethyl}-azetidin-3-yl)-acetamide;
(1-{6-[5-(2H-Pyrazol-3-yl)-pyridin-2-yloxy]-naphthalen-2-ylmethyl}-azetidin-3-yl)-methanol;
(S)-1-{6-[5-(2H-Pyrazol-3-yl)-pyridin-2-yloxy]-naphthalen-2-ylmethyl}-pyrrolidin-3-ol;
(R)-1-{6-[5-(2H-Pyrazol-3-yl)-pyridin-2-yloxy]-naphthalen-2-ylmethyl}-pyrrolidin-3-ol;
2-Hydroxy-1-(4-{6-[5-(2H-pyrazol-3-yl)-pyridin-2-yloxy]-naphthalen-2-ylmethyl}-piperazin-1-yl)-ethanone;
2-Hydroxy-N-(1-{6-[5-(2H-pyrazol-3-yl)-pyridin-2-yloxy]-naphthalen-2-ylmethyl}-piperidin-4-yl)-acetamide;
2-{6-[5-(2H-Pyrazol-3-yl)-pyridin-2-yloxy]-naphthalen-2-ylmethyl}-2-aza-spiro[3.3]heptan-6-ol;
3-Methyl-1-{6-[5-(2H-pyrazol-3-yl)-pyridin-2-yloxy]-naphthalen-2-ylmethyl}-azetidin-3-ol;
N-((R)-1-{6-[5-(2H-Pyrazol-3-yl)-pyridin-2-yloxy]-naphthalen-2-ylmethyl}-pyrrolidin-3-yl)-acetamide;
N-((S)-1-{6-[5-(2H-Pyrazol-3-yl)-pyridin-2-yloxy]-naphthalen-2-ylmethyl}-pyrrolidin-3-yl)-acetamide;
(S)-1-{6-[5-(2H-Pyrazol-3-yl)-pyridin-2-yloxy]-naphthalen-2-ylmethyl}-piperidin-3-ol;
(R)-1-{6-[5-(2H-Pyrazol-3-yl)-pyridin-2-yloxy]-naphthalen-2-ylmethyl}-piperidin-3-ol;
2-(Methyl-{6-[5-(2H-pyrazol-3-yl)-pyridin-2-yloxy]-naphthalen-2-ylmethyl}-amino)-ethanol;
(1-{6-[5-(2H-Pyrazol-3-yl)-pyridin-2-yloxy]-naphthalen-2-ylmethyl}-piperidin-4-yl)-methanol;
((S)-1-{6-[5-(2H-Pyrazol-3-yl)-pyridin-2-yloxy]-naphthalen-2-ylmethyl}-pyrrolidin-3-yl)-methanol;
2-Hydroxy-1-[(R)-3-(methyl-{6-[5-(2H-pyrazol-3-yl)-pyridin-2-yloxy]-naphthalen-2-ylmethyl}-amino)-pyrrolidin-1-yl]-ethanone;
2-Hydroxy-N-methyl-N-((S)-1-{6-[5-(2H-pyrazol-3-yl)-pyridin-2-yloxy]-naphthalen-2-ylmethyl}-pyrrolidin-3-yl)-acetamide;
2-Hydroxy-N-methyl-N-((R)-1-{6-[5-(2H-pyrazol-3-yl)-pyridin-2-yloxy]-naphthalen-2-ylmethyl}-pyrrolidin-3-yl)-acetamide;
((R)-1-{6-[5-(2H-Pyrazol-3-yl)-pyridin-2-yloxy]-naphthalen-2-ylmethyl}-pyrrolidin-3-yl)-methanol; and
2-Hydroxy-1-[(S)-3-(methyl-{6-[5-(2H-pyrazol-3-yl)-pyridin-2-yloxy]-naphthalen-2-ylmethyl}-amino)-pyrrolidin-1-yl]-ethanone;
1-(1-{(R)-6-[5-(2H-Pyrazol-3-yl)-pyridin-2-yloxy]-2,3-dihydro-benzofuran-2-ylmethyl}-piperidin-4-yl)-pyrrolidin-2-one;
1-(1-{(S)-6-[5-(2H-Pyrazol-3-yl)-pyridin-2-yloxy]-2,3-dihydro-benzofuran-2-ylmethyl}-piperidin-4-yl)-pyrrolidin-2-one;
1-[1-(2-{6-[5-(2H-Pyrazol-3-yl)-pyridin-2-yloxy]-benzofuran-3-yl}-ethyl)-piperidin-4-yl]-pyrrolidin-2-one;
(S)-3-Hydroxy-1-[1-(2-{6-[5-(2H-pyrazol-3-yl)-pyridin-2-yloxy]-benzofuran-3-yl}-ethyl)-piperidin-4-yl]-pyrrolidin-2-one;
2-Methoxy-1-[4-(2-{6-[5-(2H-pyrazol-3-yl)-pyridin-2-yloxy]-benzofuran-3-yl}-ethyl)-piperazin-1-yl]-ethanone;
(R)-2-Methoxy-1-[4-(2-{6-[5-(2H-pyrazol-3-yl)-pyridin-2-yloxy]-benzofuran-3-yl}-ethyl)-piperazin-1-yl]-propan-1-one;
1-(4-{6-[5-(2H-Pyrazol-3-yl)-pyridin-2-yloxy]-benzofuran-3-ylmethyl}-[1,4]diazepan-1-yl)-ethanone;
1-{6-[5-(2H-Pyrazol-3-yl)-pyridin-2-yloxy]-benzofuran-3-ylmethyl}-piperidine-4-carboxylic acid methylamide;
N-(1-{6-[5-(2H-Pyrazol-3-yl)-pyridin-2-yloxy]-benzofuran-3-ylmethyl}-piperidin-4-yl)-acetamide;
N-(1-{6-[5-(2H-Pyrazol-3-yl)-pyridin-2-yloxy]-benzofuran-3-ylmethyl}-piperidin-4-yl)-methanesulfonamide;
N-(1-{6-[5-(2H-Pyrazol-3-yl)-pyridin-2-yloxy]-benzofuran-3-ylmethyl}-piperidin-4-ylmethyl)-acetamide;
1-{4-[({6-[5-(2H-Pyrazol-3-yl)-pyridin-2-yloxy]-benzofuran-3-ylmethyl}-amino)-methyl]-piperidin-1-yl}-ethanone;
1-[4-({6-[5-(2H-Pyrazol-3-yl)-pyridin-2-yloxy]-benzofuran-3-ylmethyl}-amino)-piperidin-1-yl]-ethanone;
(S)-3-Hydroxy-1-(1-{6-[5-(2H-pyrazol-3-yl)-pyridin-2-yloxy]-benzofuran-3-ylmethyl}-piperidin-4-yl)-pyrrolidin-2-one;

2-Methyl-8-{6-[5-(2H-pyrazol-3-yl)-pyridin-2-yloxy]-benzofuran-3-ylmethyl}-2,8-diaza-spiro[4.5]decan-1-one;

2-(4-{6-[5-(2H-Pyrazol-3-yl)-pyridin-2-yloxy]-benzofuran-3-ylmethyl}-piperazin-1-yl)-1-pyrrolidin-1-yl-ethanone;

2-Hydroxy-N-methyl-N-((R)-1-{6-[5-(2H-pyrazol-3-yl)-pyridin-2-yloxy]-benzofuran-3-ylmethyl}-pyrrolidin-3-yl)-acetamide;

2-Hydroxy-N-methyl-N-((S)-1-{6-[5-(2H-pyrazol-3-yl)-pyridin-2-yloxy]-benzofuran-3-ylmethyl}-pyrrolidin-3-yl)-acetamide; and 2-Hydroxy-1-(7-{6-[5-(2H-pyrazol-3-yl)-pyridin-2-yloxy]-benzofuran-3-ylmethyl}-2,7-diaza-spiro[4.4]non-2-yl)-ethanone;

or a pharmaceutically acceptable salt thereof.

2. A pharmaceutical composition comprising one or more compounds of claim 1, or a pharmaceutically acceptable salt thereof, and a pharmaceutically acceptable carrier or excipient.

3. The pharmaceutical composition of claim 2, further comprising at least one additional pharmacologically active substance.

* * * * *